US011716974B2

(12) United States Patent
Bissig et al.

(10) Patent No.: US 11,716,974 B2
(45) Date of Patent: Aug. 8, 2023

(54) HUMAN LIVER CHIMERIC MOUSE WITH DEFICIENT P450 OXIDOREDUCTASE

(71) Applicant: Baylor College of Medicine, Houston, TX (US)

(72) Inventors: Karl-Dimiter Bissig, Houston, TX (US); Maria de las Mercedes Barzi Dieguez, Houston, TX (US); Peter Francis Pankowicz, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/309,871

(22) PCT Filed: Jun. 27, 2017

(86) PCT No.: PCT/US2017/039474
§ 371 (c)(1),
(2) Date: Dec. 13, 2018

(87) PCT Pub. No.: WO2018/005471
PCT Pub. Date: Jan. 4, 2018

(65) Prior Publication Data
US 2019/0166810 A1    Jun. 6, 2019

Related U.S. Application Data

(60) Provisional application No. 62/509,942, filed on May 23, 2017, provisional application No. 62/355,102, filed on Jun. 27, 2016.

(51) Int. Cl.
*A01K 67/027* (2006.01)
*A61K 49/00* (2006.01)

(52) U.S. Cl.
CPC ...... *A01K 67/0271* (2013.01); *A01K 67/0276* (2013.01); *A61K 49/0008* (2013.01); *A01K 2207/15* (2013.01); *A01K 2217/075* (2013.01); *A01K 2217/206* (2013.01)

(58) Field of Classification Search
CPC . A01K 67/271; A01K 67/276; A01K 2207/15
See application file for complete search history.

(56) References Cited

U.S. PATENT DOCUMENTS

| 6,509,514 | B1 | 1/2003 | Kneteman et al. | |
|---|---|---|---|---|
| 7,700,822 | B2 * | 4/2010 | Wolf | C12N 9/0042 800/18 |
| 7,759,541 | B2 | 7/2010 | Wolf et al. | |
| 8,569,573 | B2 | 10/2013 | Grompe et al. | |
| 8,809,619 | B2 | 8/2014 | Scheer et al. | |
| 9,167,805 | B2 | 10/2015 | Araki et al. | |
| 2006/0242723 | A1 | 10/2006 | Tanaka et al. | |
| 2009/0013417 | A1 | 1/2009 | Wolf et al. | |
| 2010/0281554 | A1 | 11/2010 | Scheer | |
| 2010/0325747 | A1 * | 12/2010 | Grompe | A01K 67/0276 800/18 |
| 2012/0045764 | A1 | 2/2012 | Grompe et al. | |
| 2014/0241991 | A1 | 8/2014 | Oshimura et al. | |
| 2015/0128298 | A1 | 5/2015 | Kohara et al. | |

FOREIGN PATENT DOCUMENTS

| CN | 104540382 A | 4/2015 | |
|---|---|---|---|
| WO | WO 2004/007708 | 1/2004 | |
| WO | WO 2005/074677 A1 | 8/2005 | |
| WO | WO-2005074677 A1 * | 8/2005 | ......... A01K 67/0278 |

OTHER PUBLICATIONS

Munoz et al. Stem Cell Rev. and Rep., vol. 5, 6-9 (Year: 2009).*
Brevini et al., Theriogenology, vol. 74, pp. 544-550 (Year: 2010).*
Patil et al., Indian Journal of Public Health research & Development, vol. 2, No. 1, 106-109 (Year: 2011).*
Khodarovich et al., Applied Biochemistry and Microbiology,vol. 49, No. 9, 711-722 (Year: 2013).*
Maksimenko et al Acta Naturae, vol. 5, No. 1, 33-46 (Year: 2013).*
Ivics et al. Nature Protocols, , vol. 9(4), pp. 810-827 (Year: 2014).*
Meng et al., J. Animal Sci. and Biotech., pp. 1-7 (Year: 2015).*
Selsby et al., (ILAR Journal, vol. 56, No. 1, p. 116-126 (Year: 2015).*
Ezashi et al Annu. Rev. Anim. Biosci. 4:223-53 (Year: 2016).*
West et al., J. Equine Vet. Sci., vol. 41, pp. 1-6 (Year: 2016).*
Yang et al., (PNAS, 113(41), E6209-E6218, 1-10 (Year: 2016).*
Lee et al., Drug Discovery Today: Disease Models, vol. 20, 13-20 (Year: 2016).*
Bissig et al PNAS 104, 51, 20507-20511 (Year: 2007).*
Wang et al Biochemical Pharmacology 105 80-90 (Year: 2016).*
Shen et al. Journal of Biological Chemistry, , 277(8), 6536-6541 (Year: 2002).*
Kato et al Drug Metab Dispos 43:1208-1217 (Year: 2015).*
Azuma et al Nat Biotechnol. August; 25(8): 903-910 (Year: 2007).*
Nakada et al Biopharm Drug Dispos . Jan. 2016;37(1):3-14, absract p. 1 (Year: 2013).*
Garciia-Garcia et al Cell, vol. 114, 727-737 (Year: 2003).*
Handerson et al Journal of Biologcal Chemistry vol. 278, No. 15, 13480-13486 (Year: 2003).*
Barzi et al Nature communication, 8: 39. 1-9 (Year: 2017).*
Barzi et al Nature Comm, 8: 39, 1-9 (Year: 2017).*
Guo et al., Cell Research, vol. 25, 767-768 (Year: 2015).*
Hsu et al Nat Biotechnology. Sep.;31(9):827-32 (Year: 2013).*
Anderson S. et al. "Predicting circulating human metabolites: how good are we?", Chemical research in toxicology, vol. 22, p. 243-256 (2009).

(Continued)

*Primary Examiner* — Anoop K Singh
(74) *Attorney, Agent, or Firm* — Cooley LLP; Matthew Pavao

(57) ABSTRACT

The present disclosure provides a chimeric non-human animal comprising human hepatocytes, methods for preparing the chimeric non-human animal comprising human hepatocytes and methods of utilizing the chimeric non-human animal comprising human hepatocytes to screening and identifying metabolites for any type of drugs, typically small molecule drugs, which might affect human liver functions and any other bodily function.

1 Claim, 31 Drawing Sheets
Specification includes a Sequence Listing.

(56) References Cited

OTHER PUBLICATIONS

Azuma H. et al. "Robust expansion of human hepatocytes in Fah-/-/Rag2-/-/Il2rg-/-mice", Nature Biotechnology, vol. 25, No. 8, p. 903-910 (2007).
Baillie T.A. "Future of toxicology-metabolic activation and drug design: challenges and opportunities in chemical toxicology", Chemical research in toxicology, vol. 19, p. 889-893 (2006).
Barker A.J. et al. "Studies leading to the identification of ZD1839 (IRESSA): an orally active, selective epidermal growth factor receptor tyrosine kinase inhibitor targeted to the treatment of cancer", Bioorganic & medicinal chemistry letters, vol. 11, p. 1911-1914 (2001).
Barzi M. et al "Human liver chimeric mice with deficient murine P450 oxidoreductase: a novel model for predicting human drug metabolism", manuscript, 8 pages, 2016.
Bateman TJ et al. "Application of chimeric mice with humanized liver for study of human-specific drug metabolism", Drug Metab Dispos, vol. 42, p. 1055-1065 (2014).
Bissig, K.D. et al. "Human liver chimeric mice provide a model for hepatitis B and C virus infection and treatment" The Journal of clinical investigation, vol. 120, p. 924-930 (2010).
Bissig-Choisat, B. et al. "Development and rescue of human familial hypercholesterolaemia in a xenograft mouse model" Nature communications, vol. 6, p. 7339 (2015).
Bissig, K.D. et al. "Repopulation of adult and neonatal mice with human hepatocytes: a chimeric animal model", Proc Natl Acad Sci USA, vol. 104, 20507-20511 (2007).
Bissig, K.D. et al. "P450-Humanized and Human Liver Chimeric Mouse Models for Studying Xenobiotic Metabolism and Toxicity", Drug Metabolism and Disposition, p. 1734-1744, (2018).
Capecchi et al. "Altering the Genome by Homologous Recombination", Science, vol. 244, p. 1288-1292, (1989).
Cong L. et al. "Multiplex genome engineering using CRISPR/Cas systems" Science, vol. 339, p. 819-823 (2013).
Cradick T. J. et al. "COSMID: A Web-based Tool for Identifying and Validating CRISPR/Cas Off-target Sites" Molecular Therapy Nucleic Acids, vol. 3, e214, 10 pages (2014).
Dalvie D. et al. "Assessment of three human in vitro systems in the generation of major human excretory and circulating metabolites", Chemical research in toxicology, vol. 22, p. 357-368 (2009).
Dandri M. et al. "Repopulation of mouse liver with human hepatocytes and in vivo infection with hepatitis B virus", Hepatology, vol. 33, p. 981-988 (2001).
Eisenberg E. et al. "Human housekeeping genes, revisited", Trends in genetics: TIG, vol. 29, p. 569-574 (2013).
Farley F.W. et al. "Widespread recombinase expression using FLPeR (flipper) mice" Genesis, vol. 28, p. 106-110, (2000).
Foster Jr, et al. "Differential effect of troglitazone on the human bile acid transporters, MRP2 and BSEP, in the PXB hepatic chimeric mouse", Toxicologic pathology, vol. 40, p. 1106-1116 (2012).
Genbank Accession No. NM_000941.2.
Genbank Accession No. NP 000932.3.
Genbank Accession No. NM_ 008898.2.
Genbank Accession No. NP_ 032924.1.
Genbank Accession No. NM_ 000206.2.
Genbank Accession No. NP_ 000197 .1.
Genbank Accession No. NM_013563.4.
Genbank Accession No. NP 038591.1.
Genbank Accession No. NM_000536.3.
Genbank Accession No. NP_ 000527.2.
Genbank Accession No. NM_ 009020.3.
Genbank Accession No. NP_ 033046.1.
Genbank Accession No. NM_000137.2.
Genbank Accession No. NP 000128.1.
Genbank Accession No. NP_ 034306.2.
Gu J. et al. "Liver-specific deletion of the NADPH-cytochrome P450 reductase gene: impact on plasma cholesterol homeostasis and the function and regulation of microsomal cytochrome P450 and heme oxygenase", J Biol Chem., vol. 278, p. 25895-25901 (2003).
Guengerich F. P. et al. "Orphans in the human cytochrome P450 superfamily: approaches to discovering functions and relevance in pharmacology" Pharmacological reviews, vol. 63, p. 684-699 (2011).
Guengerich F. P. et al. "Applying mechanisms of chemical toxicity to predict drug safety", Chemical research in toxicology, vol. 20, p. 344-369 (2007).
Haft D.H. et al. "A guild of 45 CRISPR-associated (Cas) protein families and multiple CRISPR/Cas subtypes exist in prokaryotic genomes", PLoS computational biology, vol. 1, e60 (2005).
Hasegawa M. et al. "The reconstituted 'humanized liver' in TK-NOG mice is mature and Functional", Biochemical and biophysical research communications, vol. 405, p. 405-410 (2011).
Heckel J.L. et al. "Neonatal bleeding in transgenic mice expressing urokinase-type plasminogen activator", Cell, vol. 62, p. 447-456 (1990).
Henderson CJ, et al. Inactivation of the hepatic cytochrome P450 system by conditional deletion of hepatic cytochrome P450 reductase. J Biol Chem 278, 13480-13486 (2003).
Herbst R.S. et al. "Gefitinib—a novel targeted approach to treating cancer", Nat Rev Cancer vol. 4, p. 956-965 (2004).
Hwang, W.Y. et al. "Efficient genome editing in zebrafish using a CRISPR-Cas system." Nat Biotechnol, vol. 3 I, p. 227-229 (2013).
Jansen R, et al. "Identification of genes that are associated with DNA repeats in prokaryotes", Molecular microbiology, vol. 43, p. 1565-1575 (2002).
Jinek M, et al. "A programmable dual-RNA-guided DNA endonuclease in adaptive bacterial immunity", Science, vol. 337, p. 816-821 (2012).
Kato K, et al. "Development of Murine Cyp3a Knockout Chimeric Mice with Humanized Liver", Drug Metab Dispos, vol. 43, p. 1208-1217 (2015).
Langmead B, et al. "Fast gapped-read alignment with Bowtie 2" Nat Methods, vol. 9, p. 357-359 (2012).
Li B, et al. "RSENI: accurate transcript quantification from RNA-Seq data with or without a reference genome", BMC Bioinformatics, vol. 12, p. 323 (2011).
Li, F et al., "CYP3A-mediated generation of aldehyde and hydrazine in atazanavir metabolism," Drug Metabolism and Disposition, vol. 39, No. 3, p. 394-401 (2011).
Liu X, et al. "Metabolomics reveals the formation of aldehydes and iminium in gefitinib Metabolism", Biochem Pharmacol, vol. 97, p. 111-121 (2015).
Lootens L, et al. "Steroid metabolism in chimeric mice with humanized liver", Drug testing and analysis, vol. 1, p. 531-537 (2009).
McKillop D, et al. "Metabolic disposition of gefitinib, an epidermal growth factor receptor tyrosine kinase inhibitor, in rat, dog and man", Xenobiotica; the fate of foreign compounds in biological systems, vol. 34, p. 917-934 (2004).
Mercer DF, et al. "Hepatitis C virus replication in mice with chimeric human livers", Nat Med, vol. 7, p. 927-933 (2001).
Meuleman P, et al. "Morphological and biochemical characterization of a human liver in a uPA-SCID mouse chimera", Hepatology, vol. 41, p. 847-856 (2005).
Nakada N, et al. "Murine Cyp3a knockout chimeric mice with humanized liver: prediction of the metabolic profile of nefazodone in humans", Biopharmaceutics & drug disposition, (2015).
Nelson Dr, et al. "Comparison of cytochrome P450 (CYP) genes from the mouse and human genomes, including nomenclature recommendations for genes, pseudogenes and alternative-splice variants", Pharmacogenetics, vol. 14, p. 1-18 (2004).
Nishimura T, et al. "Using chimeric mice with humanized livers to predict human drug metabolism and a drug-drug interaction" J Pharmacol Exp Ther, vol. 344, p. 388-396 (2013).
Olson H, et al. "Concordance of the toxicity of pharmaceuticals in humans and in animals", Regulatory toxicology and pharmacology: RTP, vol. 32, p. 56-67 (2000).
Pettitt, S.J. et al. "Agouti C57BL/6N embryonic stem cells for mouse genetic resources" Nat Methods, vol. 6, p. 493-495, (2009).
Ponder, K.P. et al. "Mouse hepatocytes migrate to liver parenchyma and function indefinitely after intrasplenic transplantation." Proc Natl Acad Sci USA, vol. 88, p. 1217-1221 (1991).

(56) References Cited

OTHER PUBLICATIONS

Rhim J.A. et al. "Replacement of diseased mouse liver by hepatic cell Transplantation", Science, vol. 263, p. 1149-1152 (1994).
Samuelsson K. et al. "Troglitazone metabolism and transporter effects in chimeric mice: a comparison between chimeric humanized and chimeric murinized FRG mice", Xenobiotica; the fate offoreign compounds in biological systems, vol. 44, p. 186-195 (2014).
Scheffler M. et al. "Clinical pharmacokinetics of tyrosine kinase inhibitors: focus on 4-anilinoquinazolines" Clinical pharmacokinetics, vol. 50, p. 371-403 (2011).
Scheer and Wilson "A comparison between genetically humanized and chimeric liver humanized mouse models for studies in drug metabolism and toxicity" Drug Discovery Today, vol. 21, No. 2, p. 250-263 (2016).
Shen Al, et al. "Association of multiple developmental defects and embryonic lethality with loss of microsomal NADPH-cytochrome P450 oxidoreductase" J Biol Chem, vol. 277, p. 6536-6541 (2002).
Skarnes W.C., et al. "A conditional knockout resource for the genome-wide study of mouse gene function", Nature, vol. 474, p. 337-342 (2011).
Suemizu H. et al. "Establishment of a humanized model of liver using NOD/Shi-scid IL2RgAnAuA1A1 mice", Biochemical and Biophysical Research Communications, vol. 377 No. 1, pp. 248-252 (2008).
Tateno C. et al. "Near completely humanized liver in mice shows human-type metabolic responses to drugs", American Journal of Pathology, vol. 165, No. 3, pp. 901-912 (2004).
Tanoue C, et al. "Prediction of human metabolism of the sedative-hypnotic zaleplon using chimeric mice transplanted with human hepatocytes", Xenobiotica; the fate of foreign compounds in biological systems, vol. 43, p. 956-962 (2013).
Thomas K.R. et al. "Site-directed mutagenesis by gene targeting in mouse embryo-derived stem cells", Cell, vol. 51, p. 503-512 (1987).
Washburn M.L. et al. "A humanized mouse model to study hepatitis C virus infection, immune response, and liver disease", Gastroenterology, vol. 140, p. 1334-1344 (2011).
Weng Y. et al. "Hepatic gene expression changes in mouse models with liver-specific deletion or global suppression of the NADPHcytochrome P450 reductase gene. Mechanistic implications for the regulation of microsomal cytochrome P450 and the fatty liver phenotype", J Biol Chem, vol. 280, p. 31686-31698 (2005).
Williams J.A. et al. "Drug-drug interactions for UDP-glucuronosyltransferase substrates: a pharmacokinetic explanation for typically observed low exposure (AUCi/ AUC) ratios", Drug Metab Dispos vol. 32, p. 1201-1208 (2004).
Wu L. et al. "Conditional Knockout of the Mouse NADPH-Cytochrome P450 Reductase Gene", Genesis: The Journal of Genetics and Development, vol. 36, No. 4, p. 177-181 (2003).
Xu D, et al. "Fialuridine induces acute liver failure in chimeric TK-NOG mice: a model for detecting hepatic drug toxicity prior to human testing", PLoS medicine, vol. 11, e1001628 (2014).
Zhang, R. R. et al. "Human hepatic stem cells transplanted into a fulminant hepatic failure Alb-TRECK/SCID mouse model exhibit liver reconstitution and drug metabolism capabilities", Stem Cell Res. Ther., vol. 6, p. 49, (2015).
Exhibit A: Whary, M. T. et al. "Biology and Diseases of Mice", Laboratory Animal Medicine, 2015, Chapter 3, p. 43-149.
Exhibit B: Shultz, L. D. et al. "NOD/LtSz-Rag1$^{null}$Pfp$^{null}$ Mice: A New Model System with Increased Levels of Human Peripheral Leukocyte and Hematopoietic Stem-Cell Engrafment", Transplantation, 2003, vol. 76, No. 7, p. 1036-1042.
Exhibit C: Christianson, S. W. et al. "Enhanced Human CD4 + T Cell Engraftment in p2-Microglobulin-Deficient NOD-scid Mice", The Journal of Immunology, 1997, vol. 158, p. 3578-3586.
Exhibit D: Vanwolleghem, T. et al. "Factors determining successful engraftment of hepatocytes and susceptibility of hepatitis B and C virus infection in uPA-SCID mice", Journal of Hepatology, 2010, vol. 53, p. 468-476.
Exhibit E: Gu, J. et al. "Liver-specific Deletion ofthe NADPH-Cytochrome P450 Reductase Gene", The Journal of Biological Chemistry, 2003, vol. 278, p. 25895-25901.
Exhibit F: Hasler, J. A. et al. "Human cytochromes P450", Molecular Aspects of Medicine, 1999, vol. 20, p. 32-47.
Exhibit G: Wang, X. J. et al. "Relationship between hepatic phenotype and changes in gene expression in cytochrome P450 reductase (POR) null mice", Biochem. Journal, 2005, vol. 388, p. 857-867.
Exhibit H: Russell D. W. et al. "Bile Acid Biosynthesis", Biochemistry, 1992, vol. 31, No. 20, p. 4737-4749.
Exhibit I: Weng, Y. et al. "Hepatic Gene Expression Changes in Mouse Models with Liver-specific Deletion or Global Suppression of the NADPH-Cytochrome P450 Reductase Gene", The Journal of Biological Chemistry, 2005, vol. 280, p. 31686-31698.
Exhibit J: Gu J. et al. "In Vivo Mechanisms of Tissue-Selective Drug Toxicity: Effects of Liver-Specific Knockout of the NADPH-Cytochrome P450 Reductase Gene on Acetaminophen Toxicity in Kidney, Lung, and Nasal Mucosa", Molecular Pharmacology, 2005, vol. 67, No. 3, p. 623-630.
Grompe et al. "Loss of fumarylacetoacetate hydrolase is responsible for the neonatal hepatic dysfunction phenotype of lethal albino mice", Genes & Development, 1993, vol. 7, p. 2298-2307.
Sandgren et al. "DNA rearrangement causes hepatocarcinogenesis in albumin-plasminogen activator transgenic mice", Proc. Natl. Acad. Sci. USA, 1992, vol. 89, p. 11523-11527.
Danilov et al. "Conditional genetic deletion of PTEN after a spinal cord injury enhances regenerative growth of CST axons and motor function recovery in mice" Experiemental Neurology, 2015, vol. 266, p. 147-160.

\* cited by examiner

Figure 1A
PIRF mouse strain
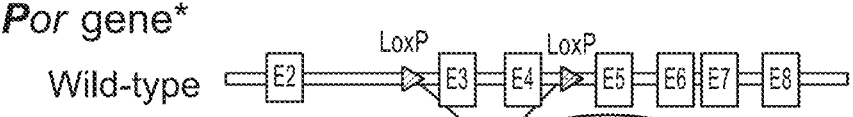
Por gene*
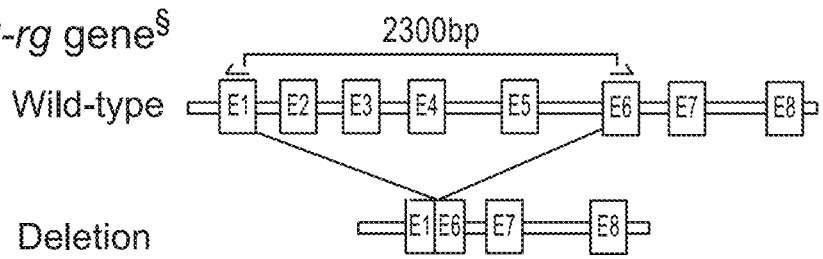
Il2-rg gene§
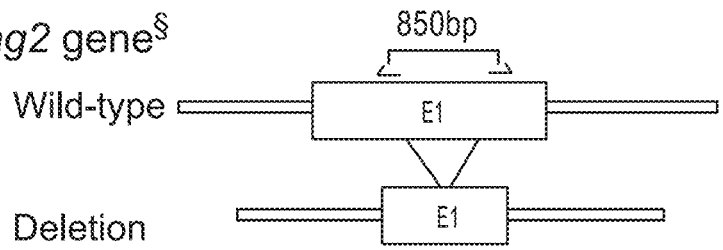
Rag2 gene§
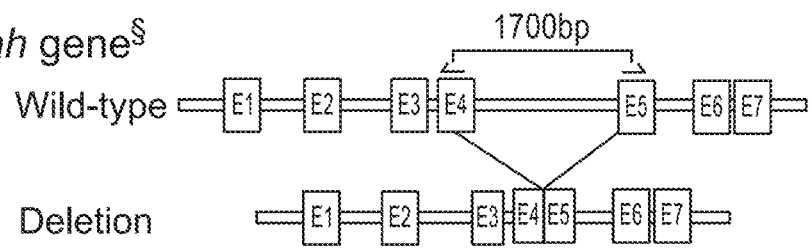
Fah gene§
*Embryonic stem cell targeting (See, Figure 4)
§ Zygote injection with Cas9 and gRNA (See, Figure 5)

Adeno-Cre [pfu/mouse]

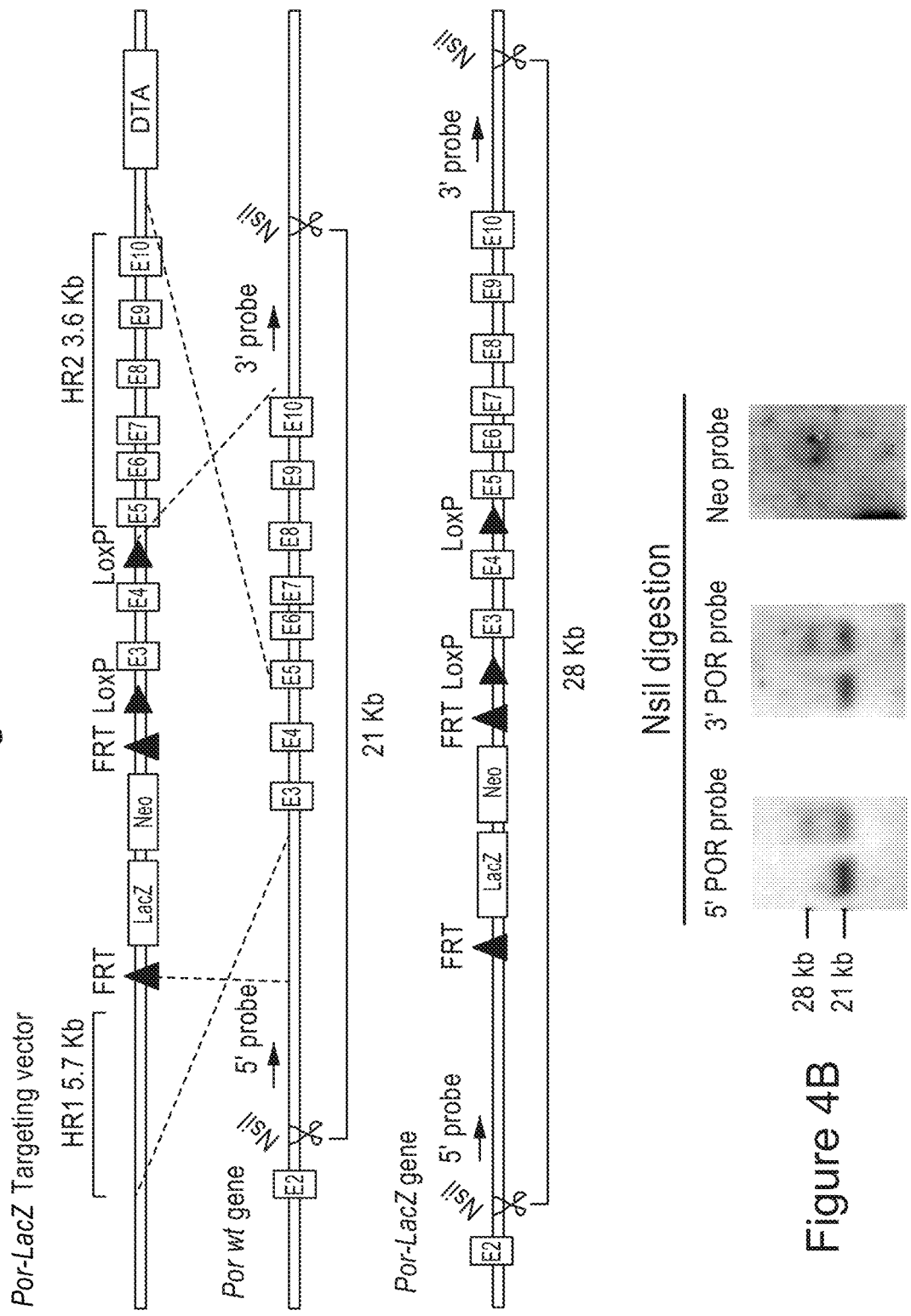

Figure 6A
*Il2 rg gene*
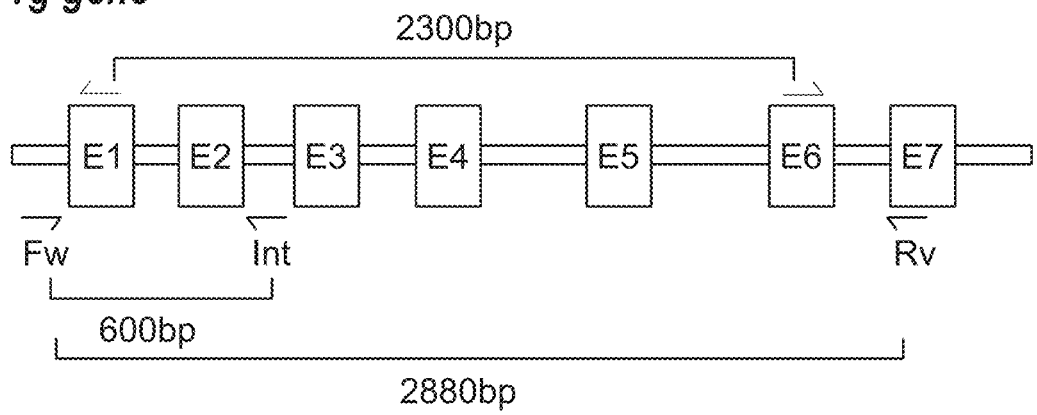
*Rag2 gene*
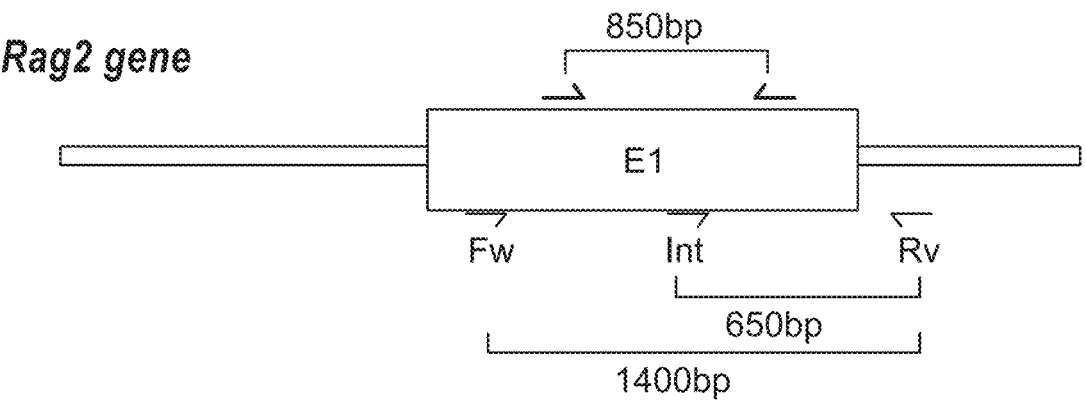
*Fah gene*
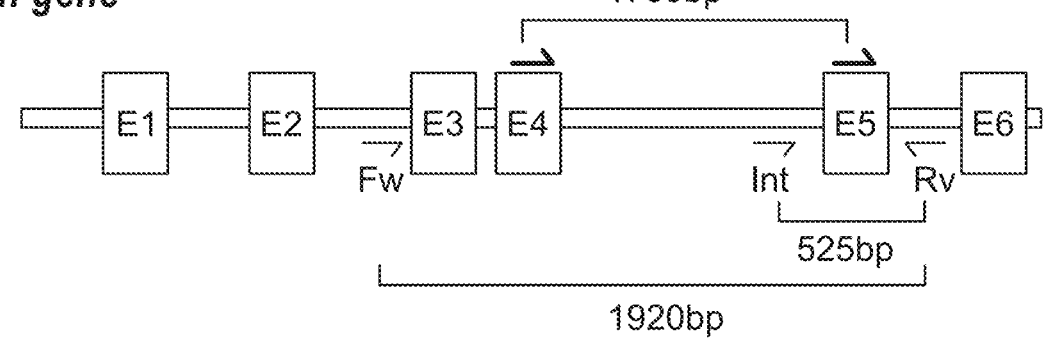

Figure 7B

| Gene KO | Deletion size (bp) | Protein modification |
|---|---|---|
| Il2 KO Del-1 | 2422bp | Frame shift from aminoacid 28: (SEQ ID NO: 50) LCWHYVQRQGECAVAKLAPLTCGIPWPSFLHCGIWNPDSKTHGADET+STOP |
| Rag2 KO Del-1 | 871bp | Frame shift from aminoacid 143: ILFNGAQ+STOP (SEQ ID NO: 51) |
| Rag2 KO Del-2 | 877bp | Frame shift from aminoacid 141: IQRSSINPP+STOP (SEQ ID NO: 52) |
| Rag2 KO Del-3 | 936bp | Frame shift from aminoacid 122: IQRSSINPP+STOP (SEQ ID NO: 53) |
| Rag2 KO Del-4 | 1088bp | Frame shift from aminoacid 142: TKKALGKS+STOP (SEQ ID NO: 54) |
| Fah KO Del-1 | 1717bp | Frame shift from aminoacid 107: (SEQ ID NO: 55) LCWHYVQRQGECAVAKLAPLTCGIPWPSFLHCGIWNPDSKTHGADET+STOP |
| Fah KO Del-2 | 1720bp | Frame shift from aminoacid 107: (SEQ ID NO: 56) LCSEARRMRCCQIGSTYLWDTMAELPPLWLEPRFEDPWGR+STOP |

Alb-CRE$^{+/-}$/POR$^{c/+}$

Alb-CRE$^{+/-}$/POR$^{c/c}$

Figure 20
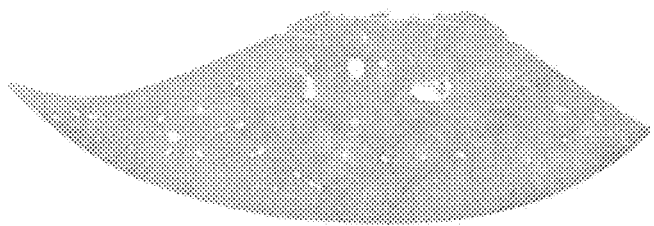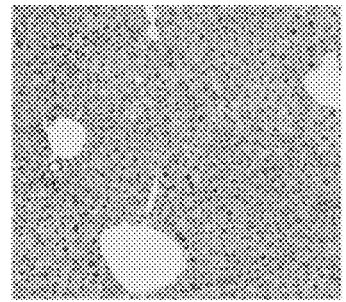

Humanized mice

POR deleted
UGDH deleted

Non-humanized

```
                         SEQUENCE LISTING

<160> NUMBER OF SEQ ID NOS: 56

<210> SEQ ID NO 1
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 1
ggcctcagag aggacatagt gccc                                            24

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
gccctctggt gtcaggtccc                                                 20

<210> SEQ ID NO 3
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 3
cctcacgcag cttaatgtgg cc                                              22

<210> SEQ ID NO 4
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 4
ggaagttaag gacgtgatta cagggagc                                        28
```

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
ctgggttgca tactggtggg                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
aaacagggtc tttgctgctg                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
acaaaggtgt ggcaagggtt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
ccaccggaag ctacgacaaa                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
gggggaattg gaggcattct                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
cttcttcccg tgctaccctc                                               20

<210> SEQ ID NO 11
<211> LENGTH: 21
<212> TYPE: DNA
<213> ORGANISM: Artificial Sequence
<220> FEATURE:
<223> OTHER INFORMATION: Synthetic Polynucleotide

```
<400> SEQUENCE: 11
cctcccacct cttcgttatc c                                            21

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 12
agtctgaggg gcttttgcta                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
agtctgaggg gcttttgcta                                              20

<210> SEQ ID NO 14
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 14 ggcccccacct gtcaaagaga gcagc                                       25

<210> SEQ ID NO 15
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 15
caaacttgac acccgtgagg tcc                                          23

<210> SEQ ID NO 16
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 16
tctatggctc ccagacggga acc                                          23

<210> SEQ ID NO 17
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 17
ccaatcatag aagtcctgcg cg                                           22

<210> SEQ ID NO 18
```

```
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 18
ccaatcatag aagtcctgcg cg                                              22

<210> SEQ ID NO 19
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 19
accttggccg catctatgtc gg                                              22

<210> SEQ ID NO 20
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 20
agaacatcat ccctgcatcc a                                               21

<210> SEQ ID NO 21
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 21
cagatccacg acggacacat t                                               21

<210> SEQ ID NO 22
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 22
cagaacatca tccctgcctc tac                                             23

<210> SEQ ID NO 23
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 23
ttgaagtcag aggagaccac ctg                                             23

<210> SEQ ID NO 24
<211> LENGTH: 2509
<212> TYPE: DNA
<213> ORGANISM: Homo sapiens

<400> SEQUENCE: 24
gaaggcggtg gtagcgcctc agtggtgtgg gcctgagccc tgcccaggtg cccgcagaga    60
```

```
gcagccgggc tgccagcgtt tcatgatcaa catgggagac tcccacgtgg acaccagctc      120
caccgtgtcc gaggcggtgg ccgaagaagt atctcttttc agcatgacgg acatgattct      180
gttttcgctc atcgtgggtc tcctaaccta ctggttcctc ttcagaaaga aaaagaaga       240 agtccccgag ttcaccaaaa ttcagacatt gacctcctct gtcagagaga gcagctttgt      300
ggaaaagatg aagaaaacgg ggaggaacat catcgtgttc tacggctccc agacggggac      360
tgcagaggag tttgccaacc gcctgtccaa ggacgcccac cgctacggga tgcgaggcat      420
gtcagcggac cctgaggagt atgacctggc cgacctgagc agcctgccag agatcgacaa      480
cgccctggtg gttttctgca tggccaccta cggtgaggga cccccaccg acaatgccca       540 ggacttctac gactggctgc aggagacaga cgtggatctc tctggggtca agttcgcggt      600
gtttggtctt gggaacaaga cctacgagca cttcaatgcc atgggcaagt acgtggacaa      660
gcggctggag cagctcggcg cccagcgcat ctttgagctg ggttgggcg acgacgatgg       720 gaacttggag gaggacttca tcacctggcg agagcagttc tggccggccg tgtgtgaaca      780
ctttggggtg aagccactg gcgaggagtc cagcattcgc cagtacgagc ttgtggtcca       840
caccgacata gatgcggcca aggtgtacat ggggagatg ggccggctga agagctacga       900
gaaccagaag ccccccttg atgccaagaa tccgttcctg gctgcagtca ccaccaaccg       960
gaagctgaac cagggaaccg agcgccacct catgcacctg gaattggaca tctcggactc     1020
caaaatcagg tatgaatctg ggaccacgt ggctgtgtac ccagccaacg actctgctct      1080
cgtcaaccag ctgggcaaaa tcctgggtgc cgacctggac gtcgtcatgt ccctgaacaa     1140
cctggatgag gagtccaaca agaagcaccc attcccgtgc cctacgtcct accgcacggc     1200
cctcacctac tacctggaca tcaccaaccc gccgcgtacc aacgtgctgt acagagctggc    1260 gcagtacgcc tcggagccct cggagcagga gctgctgcgc aagatggcct cctcctccgg    1320
cgagggcaag gagctgtacc tgagctgggt ggtggaggcc cggaggcaca tcctggccat    1380
cctgcaggac tgcccgtccc tgcggccccc catcgaccac ctgtgtgagc tgctgccgcg    1440
cctgcaggcc cgctactact ccatcgcctc atcctccaag gtccacccca actctgtgca    1500
catctgtgcg gtggttgtgg agtacgagac caaggctggc cgcatcaaca agggcgtggc    1560
caccaactgg ctgcgggcca aggagcctgc cggggagaac ggcggccgtg cgctggtgcc    1620
catgttcgtg cgcaagtccc agttccgcct gccccttcaag gccaccacgc tgtcatcat     1680 ggtgggcccc ggcaccgggg tggcaccctt cataggcttc atccaggagc gggcctggct    1740
gcgacagcag ggcaaggagg tggggagac gctgctgtac tacggctgcc gccgctcgga    1800
tgaggactac ctgtaccggg aggagctggc gcagttccac agggacggtg cgctcaccca    1860
gctcaacgtg gccttctccc gggagcagtc ccacaaggtc tacgtccagc acctgctaaa    1920
gcaagaccga gagcacctgt ggaagttgat cgaaggcggt gcccacatct acgtctgtgg    1980
ggatgcacgg aacatggcca gggatgtgca gaacaccttc tacgacatcg tggctgagct    2040
cggggccatg gagcacgcgc aggcggtgga ctacatcaag aaactgatga ccaagggccg    2100
ctactccctg gacgtgtgga gctaggggcc tgcctgcccc acccaccca cagactccgg    2160 cctgtaatca gctctcctgg ctccctcccg tagtctcctg ggtgtgtttg gcttggcctt    2220
ggcatgggcg caggcccagt gacaaagact cctctgggcc tggggtgcat cctcctcagc    2280 cccccaggcca ggtgaggtcc accggcccct ggcagcacag cccagggcct gcatgggggc   2340
accgggctcc atgcctctgg aggcctctgg ccctcggtgg ctgcacagaa gggctctttc    2400
```

```
tctctgctga gctgggccca gccccctccac gtgatttcca gtgagtgtaa ataattttaa      2460
ataacctctg gcccttggaa taaagttctg ttttctgtaa aaaaaaaaa                   2509
```

<210> SEQ ID NO 25
<211> LENGTH: 680
<212> TYPE: PRT
<213> ORGANISM: Homo sapiens

<400> SEQUENCE: 25

```
Met Ile Asn Met Gly Asp Ser His Val Asp Thr Ser Thr Val Ser
1               5                   10                  15

Glu Ala Val Ala Glu Glu Val Ser Leu Phe Ser Met Thr Asp Met Ile
                20                  25                  30

Leu Phe Ser Leu Ile Val Gly Leu Leu Thr Tyr Trp Phe Leu Phe Arg
            35                  40                  45

Lys Lys Lys Glu Glu Val Pro Glu Phe Thr Lys Ile Gln Thr Leu Thr
        50                  55                  60

Ser Ser Val Arg Glu Ser Ser Phe Val Glu Lys Met Lys Lys Thr Gly
65                  70                  75                  80

Arg Asn Ile Ile Val Phe Tyr Gly Ser Gln Thr Gly Thr Ala Glu Glu
                85                  90                  95

Phe Ala Asn Arg Leu Ser Lys Asp Ala His Arg Tyr Gly Met Arg Gly
                100                 105                 110

Met Ser Ala Asp Pro Glu Glu Tyr Asp Leu Ala Asp Leu Ser Ser Leu
            115                 120                 125

Pro Glu Ile Asp Asn Ala Leu Val Val Phe Cys Met Ala Thr Tyr Gly
        130                 135                 140

Glu Gly Asp Pro Thr Asp Asn Ala Gln Asp Phe Tyr Asp Trp Leu Gln
145                 150                 155                 160

Glu Thr Asp Val Asp Leu Ser Gly Val Lys Phe Ala Val Phe Gly Leu
                165                 170                 175

Gly Asn Lys Thr Tyr Glu His Phe Asn Ala Met Gly Lys Tyr Val Asp
                180                 185                 190

Lys Arg Leu Glu Gln Leu Gly Ala Gln Arg Ile Phe Glu Leu Gly Leu
            195                 200                 205

Gly Asp Asp Asp Gly Asn Leu Glu Glu Asp Phe Ile Thr Trp Arg Glu
        210                 215                 220

Gln Phe Trp Pro Ala Val Cys Glu His Phe Gly Val Glu Ala Thr Gly
225                 230                 235                 240

Glu Glu Ser Ser Ile Arg Gln Tyr Glu Leu Val Val His Thr Asp Ile
                245                 250                 255

Asp Ala Ala Lys Val Tyr Met Gly Glu Met Gly Arg Leu Lys Ser Tyr
                260                 265                 270

Glu Asn Gln Lys Pro Pro Phe Asp Ala Lys Asn Pro Phe Leu Ala Ala
            275                 280                 285

Val Thr Thr Asn Arg Lys Leu Asn Gln Gly Thr Glu Arg His Leu Met
        290                 295                 300

His Leu Glu Leu Asp Ile Ser Asp Ser Lys Ile Arg Tyr Glu Ser Gly
305                 310                 315                 320

Asp His Val Ala Val Tyr Pro Ala Asn Asp Ser Ala Leu Val Asn Gln
                325                 330                 335

Leu Gly Lys Ile Leu Gly Ala Asp Leu Asp Val Val Met Ser Leu Asn
                340                 345                 350

Asn Leu Asp Glu Glu Ser Asn Lys Lys His Pro Phe Pro Cys Pro Thr
```

```
                    355                 360                 365
Ser Tyr Arg Thr Ala Leu Thr Tyr Tyr Leu Asp Ile Thr Asn Pro Pro
    370                 375                 380

Arg Thr Asn Val Leu Tyr Glu Leu Ala Gln Tyr Ala Ser Glu Pro Ser
385                 390                 395                 400

Glu Gln Glu Leu Leu Arg Lys Met Ala Ser Ser Gly Glu Gly Lys
                405                 410                 415

Glu Leu Tyr Leu Ser Trp Val Val Glu Ala Arg Arg His Ile Leu Ala
            420                 425                 430

Ile Leu Gln Asp Cys Pro Ser Leu Arg Pro Pro Ile Asp His Leu Cys
        435                 440                 445

Glu Leu Leu Pro Arg Leu Gln Ala Arg Tyr Tyr Ser Ile Ala Ser Ser
    450                 455                 460

Ser Lys Val His Pro Asn Ser Val His Ile Cys Ala Val Val Val Glu
465                 470                 475                 480

Tyr Glu Thr Lys Ala Gly Arg Ile Asn Lys Gly Val Ala Thr Asn Trp
                485                 490                 495

Leu Arg Ala Lys Glu Pro Ala Gly Glu Asn Gly Gly Arg Ala Leu Val
            500                 505                 510

Pro Met Phe Val Arg Lys Ser Gln Phe Arg Leu Pro Phe Lys Ala Thr
        515                 520                 525

Thr Pro Val Ile Met Val Gly Pro Gly Thr Gly Val Ala Pro Phe Ile
    530                 535                 540

Gly Phe Ile Gln Glu Arg Ala Trp Leu Arg Gln Gln Gly Lys Glu Val
545                 550                 555                 560

Gly Glu Thr Leu Leu Tyr Tyr Gly Cys Arg Arg Ser Asp Glu Asp Tyr
                565                 570                 575

Leu Tyr Arg Glu Glu Leu Ala Gln Phe His Arg Asp Gly Ala Leu Thr
            580                 585                 590

Gln Leu Asn Val Ala Phe Ser Arg Glu Gln Ser His Lys Val Tyr Val
        595                 600                 605

Gln His Leu Leu Lys Gln Asp Arg Glu His Leu Trp Lys Leu Ile Glu
    610                 615                 620

Gly Gly Ala His Ile Tyr Val Cys Gly Asp Ala Arg Asn Met Ala Arg
625                 630                 635                 640

Asp Val Gln Asn Thr Phe Tyr Asp Ile Val Ala Glu Leu Gly Ala Met
                645                 650                 655

Glu His Ala Gln Ala Val Asp Tyr Ile Lys Lys Leu Met Thr Lys Gly
            660                 665                 670

Arg Tyr Ser Leu Asp Val Trp Ser
        675                 680

<210> SEQ ID NO 26
<211> LENGTH: 2527
<212> TYPE: DNA
<213> ORGANISM: Mus musculus

<400> SEQUENCE: 26
gggccgtggt agcgcctcag tgtgcgggc ttgcgtccgg ccccagtgcc tcagagacct      60
acaggaccgc gcgcggtgtg tgatctggtc ggtaccgagg agcgcaggtt gtgtcaccaa    120
catgggggac tctcacgaag acaccagtgc cacagtgcct gaggcagtgg ctgaagaagt    180
gtctctattc agcacaacgg acattgttct gttttctctc atcgtggggg tcctgaccta    240
ctggttcatc tttaaaaaga agaaagaaga gataccggag ttcagcaaga tccagacaac    300
```

```
ggccccacct gtcaaagaga gcagcttcgt ggaaaagatg aagaaaacgg aaggaacat      360
tattgtattc tatggctccc agacgggaac cgcggaggag tttgccaacc ggctgtccaa      420
ggatgcccac cgctatggga tgcggggcat gtctgcagac cctgaagagt atgacttggc      480
cgacctgagc agcctgcctg agatcgacaa gtccctggta gtcttctgca tggccacata      540
cggagaaggc gaccccaccg acaacgcgca ggacttctat gattggctgc aggagactga      600
cgtggacctc acgggtgtca gtttgctgt gtttggtctc gggaacaaga cctatgagca      660
cttcaacgcc atgggcaagt atgtggacca gcggctggag cagcttggcg cccagcgaat      720
ctttgagttg ggccttggtg atgacgacgg aacttggaa gaggatttca tcacatggag      780
ggagcagttc tggccagctg tgtgcgagtt cttcggggtg gaagccactg ggaggagtc      840
gagcatccgc cagtacgagc tcgtggtcca cgaagacatg gacacagcca aggtgtacac      900
gggtgagatg ggccgtctga agagctacga gaaccagaaa ccccccttcg atgccaagaa      960
tccattcctg gctgctgtca ccacgaaccg gaagctgaac caaggcactg agaggcatct     1020
aatgcacctg gaattggaca tctcagactc caagatcagg tatgaatctg agatcacgt     1080
ggctgtgtac ccagccaacg actccaccct ggtcaaccag attggggaga tcctgggggc     1140
tgacctggat gtcatcatgt ctctaaacaa tctcgatgag gagtcgaata agaagcatcc     1200
gttcccctgc ccaccacct accgcacggc cctcacctac tacctggaca tcactaaccc     1260
gccacgaacc aacgtgctct acgagctggc ccagtacgcc tcagagccct cggagcagga     1320
acacctgcac aagatggcgt cctcctccgg cgagggcaag gagctgtacc tgagctgggt     1380
ggtggaggcc cggaggcaca tcctagccat tctccaagac tacccgtccc tgcggccacc     1440
catcgaccac ctgtgcgagc tcctcccgag gctgcaggcc cgctactatt ccattgcctc     1500
gtcgtctaag gtccacccca actccgtgca catctgcgcc gtggctgtgg agtatgaagc     1560
gaagtctgga cgagtgaaca aggggtggc caccagctgg cttcggacca aggaaccagc     1620
aggagagaat ggccgccggg ccctggtccc catgttcgtc cgcaagtccc agttccgctt     1680
gcctttcaag cccaccacac ctgttatcat ggtgggcccc ggcactgggg ttgccccttt     1740
catgggcttc atccaggagc gggcttggct tcgagagcaa ggcaaggagg tcggagagac     1800
gctgctctac tacggctgcc ggcgctcgga tgaggactat ctgtaccgcg aggagctggc     1860
gcgcttccac aaggacggcg ccctcacgca gcttaatgtg gccttttccc gtgagcaggc     1920
ccacaaggtc tatgttcagc acctgctcaa gagggacaaa gagcacctgt ggaagctgat     1980
ccacgaaggt ggtgcccaca tctatgtctg cggggatgct cgaaatatgg ccaaagatgt     2040
gcagaacaca ttctatgaca tcgtggccga gtttgggccc atggagcaca cccaggctgt     2100
ggactatgtt aagaagctca tgaccaaggg ccgctactcg ctggatgtat ggagctagga     2160
gctgccgccc cccaccccct gctccctgta atcacgtcct taacttcctt ctgccgacct     2220
ccacctctgg tggttcctgc cctgcctgga cacaggagg cccagggact gactcctggc     2280
ctgagtgatg cccctcctggg cccttaggca gagcctggtc cattgtacca ggcagcctag     2340
cccagcccag ggcacatggc aagagggact ggacccacct ttgggtgatg ggtgccttag     2400
gtccccagca gctgtacaga aggggctctt ctctccacag agctggggtg cagccccaac     2460
atgtgatttt gaatgagtgt aaataatttt aaataaccctg gcccttggaa taaagttgtt     2520
ttctgta                                                             2527
```

<210> SEQ ID NO 27

<211> LENGTH: 678
<212> TYPE: PRT
<213> ORGANISM: Mus musculus

<400> SEQUENCE: 27

```
Met Gly Asp Ser His Glu Asp Thr Ser Ala Thr Val Pro Glu Ala Val
1               5                   10                  15

Ala Glu Glu Val Ser Leu Phe Ser Thr Thr Asp Ile Val Leu Phe Ser
            20                  25                  30

Leu Ile Val Gly Val Leu Thr Tyr Trp Phe Ile Phe Lys Lys Lys Lys
        35                  40                  45

Glu Glu Ile Pro Glu Phe Ser Lys Ile Gln Thr Thr Ala Pro Pro Val
50                  55                  60

Lys Glu Ser Ser Phe Val Glu Lys Met Lys Lys Thr Gly Arg Asn Ile
65                  70                  75                  80

Ile Val Phe Tyr Gly Ser Gln Thr Gly Thr Ala Glu Phe Ala Asn
                85                  90                  95

Arg Leu Ser Lys Asp Ala His Arg Tyr Gly Met Arg Gly Met Ser Ala
            100                 105                 110

Asp Pro Glu Glu Tyr Asp Leu Ala Asp Leu Ser Ser Leu Pro Glu Ile
        115                 120                 125

Asp Lys Ser Leu Val Val Phe Cys Met Ala Thr Tyr Gly Glu Gly Asp
130                 135                 140

Pro Thr Asp Asn Ala Gln Asp Phe Tyr Asp Trp Leu Gln Glu Thr Asp
145                 150                 155                 160

Val Asp Leu Thr Gly Val Lys Phe Ala Val Phe Gly Leu Gly Asn Lys
                165                 170                 175

Thr Tyr Glu His Phe Asn Ala Met Gly Lys Tyr Val Asp Gln Arg Leu
            180                 185                 190

Glu Gln Leu Gly Ala Gln Arg Ile Phe Glu Leu Gly Leu Gly Asp Asp
        195                 200                 205

Asp Gly Asn Leu Glu Glu Asp Phe Ile Thr Trp Arg Glu Gln Phe Trp
210                 215                 220

Pro Ala Val Cys Glu Phe Phe Gly Val Glu Ala Thr Gly Glu Glu Ser
225                 230                 235                 240

Ser Ile Arg Gln Tyr Glu Leu Val Val His Glu Asp Met Asp Thr Ala
                245                 250                 255

Lys Val Tyr Thr Gly Glu Met Gly Arg Leu Lys Ser Tyr Glu Asn Gln
            260                 265                 270

Lys Pro Pro Phe Asp Ala Lys Asn Pro Phe Leu Ala Ala Val Thr Thr
        275                 280                 285

Asn Arg Lys Leu Asn Gln Gly Thr Glu Arg His Leu Met His Leu Glu
290                 295                 300

Leu Asp Ile Ser Asp Ser Lys Ile Arg Tyr Glu Ser Gly Asp His Val
305                 310                 315                 320

Ala Val Tyr Pro Ala Asn Asp Ser Thr Leu Val Asn Gln Ile Gly Glu
                325                 330                 335

Ile Leu Gly Ala Asp Leu Asp Val Ile Met Ser Leu Asn Asn Leu Asp
            340                 345                 350

Glu Glu Ser Asn Lys Lys His Pro Phe Pro Cys Pro Thr Thr Tyr Arg
        355                 360                 365

Thr Ala Leu Thr Tyr Tyr Leu Asp Ile Thr Asn Pro Pro Arg Thr Asn
370                 375                 380

Val Leu Tyr Glu Leu Ala Gln Tyr Ala Ser Glu Pro Ser Glu Gln Glu
```

385         390              395              400
His Leu His Lys Met Ala Ser Ser Gly Glu Gly Lys Leu Tyr
                405             410             415

Leu Ser Trp Val Val Glu Ala Arg Arg His Ile Leu Ala Ile Leu Gln
            420             425             430

Asp Tyr Pro Ser Leu Arg Pro Pro Ile Asp His Leu Cys Glu Leu Leu
                435             440             445

Pro Arg Leu Gln Ala Arg Tyr Tyr Ser Ile Ala Ser Ser Ser Lys Val
450             455             460

His Pro Asn Ser Val His Ile Cys Ala Val Ala Val Glu Tyr Glu Ala
465             470             475             480

Lys Ser Gly Arg Val Asn Lys Gly Val Ala Thr Ser Trp Leu Arg Thr
                485             490             495

Lys Glu Pro Ala Gly Glu Asn Gly Arg Arg Ala Leu Val Pro Met Phe
            500             505             510

Val Arg Lys Ser Gln Phe Arg Leu Pro Phe Lys Pro Thr Thr Pro Val
        515             520             525

Ile Met Val Gly Pro Gly Thr Gly Val Ala Pro Phe Met Gly Phe Ile
530             535             540

Gln Glu Arg Ala Trp Leu Arg Glu Gln Gly Lys Glu Val Gly Glu Thr
545             550             555             560

Leu Leu Tyr Tyr Gly Cys Arg Arg Ser Asp Glu Asp Tyr Leu Tyr Arg
            565             570             575

Glu Glu Leu Ala Arg Phe His Lys Asp Gly Ala Leu Thr Gln Leu Asn
                580             585             590

Val Ala Phe Ser Arg Glu Gln Ala His Lys Val Tyr Val Gln His Leu
            595             600             605

Leu Lys Arg Asp Lys Glu His Leu Trp Lys Leu Ile His Glu Gly Gly
        610             615             620

Ala His Ile Tyr Val Cys Gly Asp Ala Arg Asn Met Ala Lys Asp Val
625             630             635             640

Gln Asn Thr Phe Tyr Asp Ile Val Ala Glu Phe Gly Pro Met Glu His
                645             650             655

Thr Gln Ala Val Asp Tyr Val Lys Lys Leu Met Thr Lys Gly Arg Tyr
            660             665             670

Ser Leu Asp Val Trp Ser
        675

<210> SEQ ID NO 28
<211> LENGTH: 1560
<212> TYPE: DNA
<213> ORGANISM: Homo sapiens

<400> SEQUENCE: 28
agaggaaacg tgtgggtggg gaggggtagt gggtgaggga cccaggttcc tgacacagac    60
agactacacc cagggaatga agagcaagcg ccatgttgaa gccatcatta ccattcacat   120
ccctcttatt cctgcagctg cccctgctgg gagtggggct gaacacgaca attctgacgc   180
ccaatgggaa tgaagacacc acagctgatt tcttcctgac cactatgccc actgactccc   240
tcagtgtttc cactctgccc ctcccagagg ttcagtgttt tgtgttcaat gtcgagtaca   300
tgaattgcac ttggaacagc agctctgagc ccagcctac caacctcact ctgcattatt   360
ggtacaagaa ctcggataat gataaagtcc agaagtgcag ccactatcta ttctctgaag   420
aaatcacttc tggctgtcag ttgcaaaaaa aggagatcca cctctaccaa acatttgttg   480

```
ttcagctcca ggacccacgg gaacccagga gacaggccac acagatgcta aaactgcaga    540
atctggtgat ccctgggct ccagagaacc taacacttca caaactgagt gaatcccagc    600
tagaactgaa ctggaacaac agattcttga ccactgtttt ggagcacttg gtgcagtacc    660
ggactgactg ggaccacagc tggactgaac aatcagtgga ttatagacat aagttctcct    720
tgcctagtgt ggatgggcag aaacgctaca cgtttcgtgt tcggagccgc tttaacccac    780
tctgtggaag tgctcagcat tggagtgaat ggagccaccc aatccactgg gggagcaata    840
cttcaaaaga gaatccttc ctgtttgcat tggaagccgt ggttatctct gttggctcca    900
tgggattgat tatcagcctt ctctgtgtgt atttctggct ggaacggacg atgccccgaa    960
ttcccaccct gaagaaccta gaggatcttg ttactgaata ccacgggaac ttttcggcct   1020
ggagtggtgt gtctaaggga ctggctgaga gtctgcagcc agactacagt gaacgactct   1080
gcctcgtcag tgagattccc ccaaaaggag gggcccttgg ggaggggcct ggggcctccc   1140
catgcaacca gcatagcccc tactgggccc cccatgtta cacccctaaag cctgaaacct   1200
gaaccccaat cctctgacag aagaacccca gggtcctgta gccctaagtg gtactaactt   1260
tccttcattc aacccacctg cgtctcatac tcacctcacc ccactgtggc tgatttggaa   1320
ttttgtgccc ccatgtaagc accccttcat ttggcattcc ccacttgaga attacccttt   1380
tgccccgaac atgtttttct tctccctcag tctggcccctt cctttttcgca ggattcttcc   1440
tccctccctc tttccctccc ttcctctttc catctaccct ccgattgttc ctgaaccgat   1500
gagaaataaa gtttctgttg ataatcatca aaaaaaaaa aaaaaaaaa aaaaaaaaa     1560
```

<210> SEQ ID NO 29
<211> LENGTH: 369
<212> TYPE: PRT
<213> ORGANISM: Homo sapiens

<400> SEQUENCE: 29

```
Met Leu Lys Pro Ser Leu Pro Phe Thr Ser Leu Phe Leu Gln Leu
1               5                   10                  15

Pro Leu Gly Val Gly Leu Asn Thr Thr Ile Leu Thr Pro Asn Gly
                20                  25                  30

Asn Glu Asp Thr Thr Ala Asp Phe Phe Leu Thr Thr Met Pro Thr Asp
            35                  40                  45

Ser Leu Ser Val Ser Thr Leu Pro Leu Pro Glu Val Gln Cys Phe Val
        50                  55                  60

Phe Asn Val Glu Tyr Met Asn Cys Thr Trp Asn Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
```

|   |   | 180 |   |   |   | 185 |   |   |   | 190 |   |
|---|---|---|---|---|---|---|---|---|---|---|---|

Trp Asp His Ser Trp Thr Glu Gln Ser Val Asp Tyr Arg His Lys Phe
    195        200        205

Ser Leu Pro Ser Val Asp Gly Gln Lys Arg Tyr Thr Phe Arg Val Arg
210        215        220

Ser Arg Phe Asn Pro Leu Cys Gly Ser Ala Gln His Trp Ser Glu Trp
225        230        235        240

Ser His Pro Ile His Trp Gly Ser Asn Thr Ser Lys Glu Asn Pro Phe
    245        250        255

Leu Phe Ala Leu Glu Ala Val Val Ile Ser Val Gly Ser Met Gly Leu
    260        265        270

Ile Ile Ser Leu Leu Cys Val Tyr Phe Trp Leu Glu Arg Thr Met Pro
    275        280        285

Arg Ile Pro Thr Leu Lys Asn Leu Glu Asp Leu Val Thr Glu Tyr His
    290        295        300

Gly Asn Phe Ser Ala Trp Ser Gly Val Ser Lys Gly Leu Ala Glu Ser
305        310        315        320

Leu Gln Pro Asp Tyr Ser Glu Arg Leu Cys Leu Val Ser Glu Ile Pro
    325        330        335

Pro Lys Gly Gly Ala Leu Gly Glu Gly Pro Gly Ala Ser Pro Cys Asn
    340        345        350

Gln His Ser Pro Tyr Trp Ala Pro Pro Cys Tyr Thr Leu Lys Pro Glu
    355        360        365

Thr

<210> SEQ ID NO 30
<211> LENGTH: 1663
<212> TYPE: DNA
<213> ORGANISM: Mus musculus

<400> SEQUENCE: 30

| | | | | | |
|---|---|---|---|---|---|
| aggaaatgta | tgggtgggga | gggcttgtgg | gagagtggtt | cagggttctg acacagacta | 60 |
| cacccagaga | aagaagagca | agcaccatgt | tgaaactatt | attgtcacct agatccttct | 120 |
| tagtccttca | gctgctcctg | ctgagggcag | ggtggagctc | caaggtcctc atgtccagtg | 180 |
| cgaatgaaga | catcaaagct | gatttgatcc | tgacttctac | agcccctgaa cacctcagtg | 240 |
| ctcctactct | gcccttcca | gaggttcagt | gctttgtgtt | caacatagag tacatgaatt | 300 |
| gcacttggaa | tagcagttct | gagcctcagg | caaccaacct | cacgctgcac tataggtaca | 360 |
| aggtatctga | taataataca | ttccaggagt | gcagtcacta | tttgttctcc aaagagatta | 420 |
| cttctggctg | tcagatacaa | aaagaagata | ccagctctca | ccagacattt gttgtccagc | 480 |
| tccaggaccc | ccagaaaccc | cagaggcgag | ctgtacagaa | gctaaaccta cagaatcttg | 540 |
| tgatcccacg | ggctccagaa | aatctaacac | tcagcaatct | gagtgaatcc cagctagagc | 600 |
| tgagatggaa | aagcagacat | attaaagaac | gctgtttaca | atacttggtg cagtaccgga | 660 |
| gcaacagaga | tcgaagctgg | acggaactaa | tagtgaatca | tgaacctaga ttctccctgc | 720 |
| ctagtgtgga | tgagctgaaa | cggtacacat | ttcgggttcg | gagccgctat aacccaatct | 780 |
| gtggaagttc | tcaacagtgg | agtaaatgga | gccagcctgt | ccactggggg agtcatactg | 840 |
| tagaggagaa | tccttccttg | tttgcactgg | aagctgtgct | tatccctgtt ggcaccatgg | 900 |
| ggttgattat | taccctgatc | tttgtgtact | gttggttgga | acgaatgcct ccaattcccc | 960 |
| ccatcaagaa | tctagaggat | ctggttactg | aataccaagg | gaacttttcg gcctggagtg | 1020 |

-continued

```
gtgtgtctaa agggctgact gagagtctgc agccagacta cagtgaacgg ttctgccacg    1080
tcagcgagat tccccccaaa ggaggggccc taggagaggg gcctggaggt tctccttgca    1140
gcctgcatag cccttactgg cctcccccat gttattctct gaagccggaa gcctgaacat    1200
caatcctttg atggaacctc aaagtcctat agtcctaagt gacgctaacc tcccctactc    1260
accttggcaa tctggatcca atgctcactg ccttcccttg gggctaagtt tcgatttcct    1320 gtccatgta actgcttttc tgttccatat gccctacttg agagtgtccc ttgccctctt    1380
tccctgcaca agccctccca tgcccagcct aacacctttc cactttcttt gaagagagtc    1440
ttaccctgta gcccagggtg gctgggagct cactatgtag gccaggttgg cctccaactc    1500
acaggctatc ctcccacctc tgcctcataa gagttggggt tactggcatg caccaccaca    1560
cccagcatgg tccttctctt ttataggatt ctccctccct ttttctacct atgattcaac    1620
tgtttccaaa tcaacaagaa ataaagtttt taaccaatga tca                      1663
```

<210> SEQ ID NO 31
<211> LENGTH: 369
<212> TYPE: PRT
<213> ORGANISM: Mus musculus

<400> SEQUENCE: 31

```
Met Leu Lys Leu Leu Ser Pro Arg Ser Phe Leu Val Leu Gln Leu
1               5                   10                  15

Leu Leu Leu Arg Ala Gly Trp Ser Ser Lys Val Leu Met Ser Ser Ala
            20                  25                  30

Asn Glu Asp Ile Lys Ala Asp Leu Ile Leu Thr Ser Thr Ala Pro Glu
        35                  40                  45

His Leu Ser Ala Pro Thr Leu Pro Leu Pro Glu Val Gln Cys Phe Val
    50                  55                  60

Phe Asn Ile Glu Tyr Met Asn Cys Thr Trp Asn Ser Ser Ser Glu Pro
65                  70                  75                  80

Gln Ala Thr Asn Leu Thr Leu His Tyr Arg Tyr Lys Val Ser Asp Asn
                85                  90                  95

Asn Thr Phe Gln Glu Cys Ser His Tyr Leu Phe Ser Lys Glu Ile Thr
            100                 105                 110

Ser Gly Cys Gln Ile Gln Lys Glu Asp Ile Gln Leu Tyr Gln Thr Phe
        115                 120                 125

Val Val Gln Leu Gln Asp Pro Gln Lys Pro Gln Arg Arg Ala Val Gln
    130                 135                 140

Lys Leu Asn Leu Gln Asn Leu Val Ile Pro Arg Ala Pro Glu Asn Leu
145                 150                 155                 160

Thr Leu Ser Asn Leu Ser Glu Ser Gln Leu Glu Leu Arg Trp Lys Ser
                165                 170                 175

Arg His Ile Lys Glu Arg Cys Leu Gln Tyr Leu Val Gln Tyr Arg Ser
            180                 185                 190

Asn Arg Asp Arg Ser Trp Thr Glu Leu Ile Val Asn His Glu Pro Arg
        195                 200                 205

Phe Ser Leu Pro Ser Val Asp Glu Leu Lys Arg Tyr Thr Phe Arg Val
    210                 215                 220

Arg Ser Arg Tyr Asn Pro Ile Cys Gly Ser Gln Gln Trp Ser Lys
225                 230                 235                 240

Trp Ser Gln Pro Val His Trp Gly Ser His Thr Val Glu Glu Asn Pro
                245                 250                 255

Ser Leu Phe Ala Leu Glu Ala Val Leu Ile Pro Val Gly Thr Met Gly
```

```
                260              265                 270
Leu Ile Ile Thr Leu Ile Phe Val Tyr Cys Trp Leu Glu Arg Met Pro
            275                 280                 285

Pro Ile Pro Ile Lys Asn Leu Glu Asp Leu Val Thr Glu Tyr Gln
        290                 295                 300

Gly Asn Phe Ser Ala Trp Ser Gly Val Ser Lys Gly Leu Thr Glu Ser
305                 310                 315                 320

Leu Gln Pro Asp Tyr Ser Glu Arg Phe Cys His Val Ser Glu Ile Pro
                325                 330                 335

Pro Lys Gly Gly Ala Leu Gly Glu Gly Pro Gly Ser Pro Cys Ser
        340                 345                 350

Leu His Ser Pro Tyr Trp Pro Pro Cys Tyr Ser Leu Lys Pro Glu
        355                 360                 365

Ala

<210> SEQ ID NO 32
<211> LENGTH: 2457
<212> TYPE: DNA
<213> ORGANISM: Homo sapiens

<400> SEQUENCE: 32
```

| | | | | | |
|---|---|---|---|---|---|
| attagatcag | tgttcataag | aacatctgta | ggcacacata | cacactctct | ttacagtcag | 60 |
| ccttctgctt | gccacagtca | tagtgggcag | tcagtgaatc | ttccccaagt | gctgacaatt | 120 |
| aatacctggt | ttagcggcaa | agattcagag | aggcgtgagc | agcccctctg | gccttcagac | 180 |
| aaaaatctac | gtaccatcag | aaactatgtc | tctgcagatg | gtaacagtca | gtaataacat | 240 |
| agccttaatt | cagccaggct | tctcactgat | gaattttgat | ggacaagttt | tcttctttgg | 300 |
| acaaaaaggc | tggcccaaaa | gatcctgccc | cactggagtt | ttccatctgg | atgtaaagca | 360 |
| taaccatgtc | aaactgaagc | ctacaatttt | ctctaaggat | tcctgctacc | tcctcctct | 420 |
| tcgctaccca | gccacttgca | cattcaaagg | cagcttggag | tctgaaaagc | atcaatacat | 480 |
| catccatgga | gggaaaacac | caaacaatga | ggtttcagat | aagatttatg | tcatgtctat | 540 |
| tgtttgcaag | aacaacaaaa | aggttacttt | tcgctgcaca | gagaaagact | tggtaggaga | 600 |
| tgttcctgaa | gccagatatg | gtcattccat | taatgtggtg | tacagccgag | ggaaaagtat | 660 |
| gggtgttctc | tttggaggac | gctcatacat | gccttctacc | cacagaacca | cagaaaaatg | 720 |
| gaatagtgta | gctgactgcc | tgccctgtgt | tttcctggtg | gattttgaat | tgggtgtgc | 780 |
| tacatcatac | attcttccag | aacttcagga | tgggctatct | tttcatgtct | ctattgccaa | 840 |
| aaatgacacc | atctatattt | taggaggaca | ttcacttgcc | aataatatcc | ggcctgccaa | 900 |
| cctgtacaga | ataaggggttg | atcttcccct | gggtagccca | gctgtgaatt | gcacagtctt | 960 |
| gccaggagga | atctctgtct | ccagtgcaat | cctgactcaa | actaacaatg | atgaatttgt | 1020 |
| tattgttggt | ggctatcagc | ttgaaaatca | aaaagaatg | atctgcaaca | tcatctcttt | 1080 |
| agaggacaac | aagatagaaa | ttcgtgagat | ggagaccccca | gattggaccc | cagacattaa | 1140 |
| gcacagcaag | atatggtttg | gaagcaacat | gggaaatgga | actgtttttc | ttggcatacc | 1200 |
| aggagacaat | aaacaagttg | tttcagaagg | attctatttc | tatatgttga | aatgtgctga | 1260 |
| agatgatact | aatgaagagc | agacaacatt | cacaaacagt | caaacatcaa | cagaagatcc | 1320 |
| agggggattcc | actccctttg | aagactctga | agaattttgt | ttcagtgcag | aagcaaatag | 1380 |
| ttttgatggt | gatgatgaat | tgacaccta | taatgaagat | gatgaagaag | atgagtctga | 1440 |
| gacaggctac | tggattacat | gctgccctac | ttgtgatgtg | gatatcaaca | cttgggtacc | 1500 |

```
attctattca actgagctca acaaacccgc catgatctac tgctctcatg gggatgggca    1560
ctgggtccat gctcagtgca tggatctggc agaacgcaca ctcatccatc tgtcagcagg    1620
aagcaacaag tattactgca atgagcatgt ggagatagca agagctctac acactcccca    1680
aagagtccta cccttaaaaa agcctccaat gaaatccctc cgtaaaaaag gttctggaaa    1740
aatcttgact cctgccaaga aatcctttct tagaaggttg tttgattagt tttgcaaaag    1800
cctttcagat tcaggtgtat ggaattttg aatctatttt taaaatcata acattgattt     1860
taaaaataca ttttgttta tttaaaatgc ctatgttttc ttttagttac atgaattaag     1920
ggccagaaaa aagtgtttat aatgcaatga taaataaagt cattctagac cctatacatt    1980
ttgaaaatat tttacccaaa tactcaattt actaatttat tcttcactga ggatttctga    2040
tctgattttt tattcaacaa accttaaaca cccagaagca gtaataatca tcgaggtatg    2100
tttatattta ttatataagt cttggtaaca aataacctat aaagtgttta tgacaaattt    2160
agccaataaa gaaattaaca cccaaaagaa ttaaattgat tattttgtgc aacataacaa    2220
ttcggcagtt ggccaaaact taaaagcaag atctactaca tcccacatta gtgttcttta    2280
tataccttca agcaacccett tggattatgc ccatgaacaa gttagtttct catagcttta    2340
cagatgtaga tataaatata aatatatgta tacatataga tagataatgt tctccactga    2400
cacaaaagaa gaaataaata atctacatca aaaaaaaaaa aaaaaaaaaa aaaaaaa       2457

<210> SEQ ID NO 33
<211> LENGTH: 527
<212> TYPE: PRT
<213> ORGANISM: Homo sapiens

<400> SEQUENCE: 33

Met Ser Leu Gln Met Val Thr Val Ser Asn Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Leu
        35                  40                  45

Asp Val Lys His Asn His Val Lys Leu Lys Pro Thr Ile Phe Ser Lys
    50                  55                  60

Asp Ser Cys Tyr Leu Pro Pro Leu Arg Tyr Pro Ala Thr Cys Thr Phe
65                  70                  75                  80

Lys Gly Ser Leu Glu Ser Glu Lys His Gln Tyr Ile Ile His Gly Gly
                85                  90                  95

Lys Thr Pro Asn Asn Glu Val Ser Asp Lys Ile Tyr Val Met Ser Ile
            100                 105                 110

Val Cys Lys Asn Asn Lys Lys Val Thr Phe Arg Cys Thr Glu Lys Asp
        115                 120                 125

Leu Val Gly Asp Val Pro Glu Ala Arg Tyr Gly His Ser Ile Asn Val
    130                 135                 140

Val Tyr Ser Arg Gly Lys Ser Met Gly Val Leu Phe Gly Gly Arg Ser
145                 150                 155                 160

Tyr Met Pro Ser Thr His Arg Thr Thr Glu Lys Trp Asn Ser Val Ala
                165                 170                 175

Asp Cys Leu Pro Cys Val Phe Leu Val Asp Phe Glu Phe Gly Cys Ala
            180                 185                 190

Thr Ser Tyr Ile Leu Pro Glu Leu Gln Asp Gly Leu Ser Phe His Val
        195                 200                 205
```

| | | | | | | | | | | | | |
|---|---|---|---|---|---|---|---|---|---|---|---|---|
|Ser|Ile|Ala|Lys|Asn|Asp|Thr|Ile|Tyr|Ile|Leu|Gly|Gly|His|Ser|Leu|

Ser Ile Ala Lys Asn Asp Thr Ile Tyr Ile Leu Gly Gly His Ser Leu
    210                 215                 220

Ala Asn Asn Ile Arg Pro Ala Asn Leu Tyr Arg Ile Arg Val Asp Leu
225                 230                 235                 240

Pro Leu Gly Ser Pro Ala Val Asn Cys Thr Val Leu Pro Gly Gly Ile
                245                 250                 255

Ser Val Ser Ser Ala Ile Leu Thr Gln Thr Asn Asn Asp Glu Phe Val
            260                 265                 270

Ile Val Gly Gly Tyr Gln Leu Glu Asn Gln Lys Arg Met Ile Cys Asn
        275                 280                 285

Ile Ile Ser Leu Glu Asp Asn Lys Ile Glu Ile Arg Glu Met Glu Thr
    290                 295                 300

Pro Asp Trp Thr Pro Asp Ile Lys His Ser Lys Ile Trp Phe Gly Ser
305                 310                 315                 320

Asn Met Gly Asn Gly Thr Val Phe Leu Gly Ile Pro Gly Asp Asn Lys
                325                 330                 335

Gln Val Val Ser Glu Gly Phe Tyr Phe Tyr Met Leu Lys Cys Ala Glu
            340                 345                 350

Asp Asp Thr Asn Glu Glu Gln Thr Thr Phe Thr Asn Ser Gln Thr Ser
        355                 360                 365

Thr Glu Asp Pro Gly Asp Ser Thr Pro Phe Glu Asp Ser Glu Phe
    370                 375                 380

Cys Phe Ser Ala Glu Ala Asn Ser Phe Asp Gly Asp Glu Phe Asp
385                 390                 395                 400

Thr Tyr Asn Glu Asp Asp Glu Asp Glu Ser Glu Thr Gly Tyr Trp
                405                 410                 415

Ile Thr Cys Cys Pro Thr Cys Asp Val Asp Ile Asn Thr Trp Val Pro
            420                 425                 430

Phe Tyr Ser Thr Glu Leu Asn Lys Pro Ala Met Ile Tyr Cys Ser His
        435                 440                 445

Gly Asp Gly His Trp Val His Ala Gln Cys Met Asp Leu Ala Glu Arg
    450                 455                 460

Thr Leu Ile His Leu Ser Ala Gly Ser Asn Lys Tyr Tyr Cys Asn Glu
465                 470                 475                 480

His Val Glu Ile Ala Arg Ala Leu His Thr Pro Gln Arg Val Leu Pro
                485                 490                 495

Leu Lys Lys Pro Pro Met Lys Ser Leu Arg Lys Lys Gly Ser Gly Lys
            500                 505                 510

Ile Leu Thr Pro Ala Lys Lys Ser Phe Leu Arg Arg Leu Phe Asp
        515                 520                 525

<210> SEQ ID NO 34
<211> LENGTH: 3393
<212> TYPE: DNA
<213> ORGANISM: Mus musculus

<400> SEQUENCE: 34
actctaccct gcagccttca gcttggcaca aactaaacag tgactcttcc ccaagtgccg     60
agtttaattc ctggcttggc cgaaaggatt cagagaggga taagcagccc ctctggcctt    120
cagtgccaaa ataagaaaga gtatttcaca tccacaagca ggaagtacac ttcatacctc    180
tctaagataa aagaccctatt cacaatcaaa aatgtccctg cagatggtaa cagtgggtca    240
taacatagcc ttaattcaac caggcttctc acttatgaat tttgatggcc aagttttctt    300

-continued

| | |
|---|---|
| ctttggccag aaaggctggc ctaagagatc ctgtcctact ggagtctttc attttgatat | 360 |
| aaaacaaaat catctcaaac tgaagcctgc aatcttctct aaagattcct gctacctccc | 420 |
| acctcttcgt tatccagcta cttgctcata caaaggcagc atagactctg acaagcatca | 480 |
| atatatcatt cacggaggga aaacaccaaa caatgagctt ccgataaga tttatatcat | 540 |
| gtctgtcgct tgcaagaata acaaaaaagt tactttccgt tgcacagaga aagacttagt | 600 |
| aggagatgtc cctgaaccca gatacggcca ttccattgac gtggtgtata gtcgagggaa | 660 |
| aagcatgggt gttctctttg gaggacgttc atacatgcct tctacccaga gaaccacaga | 720 |
| aaaatggaat agtgtagctg actgcctacc ccatgttttc ttgatagatt ttgaatttgg | 780 |
| gtgtgctaca tcatatattc tcccagaact tcaggatggg ctgtcttttc atgtttctat | 840 |
| tgccagaaac gataccgttt atattttggg aggacactca cttgccagta atatacgccc | 900 |
| tgctaacttg tatagaataa gagtggacct tcccctgggt accccagcag tgaattgcac | 960 |
| agtcttgcca ggaggaatct ctgtctccag tgcaatcctc actcaaacaa acaatgatga | 1020 |
| atttgttatt gtgggtggtt atcagctgga aaatcagaaa aggatggtct gcagccttgt | 1080 |
| ctctctaggg gacaacacga ttgaaatcag tgagatggag actcctgact ggacctcaga | 1140 |
| tattaagcat agcaaaatat ggtttggaag caacatggga aacgggacta ttttccttgg | 1200 |
| cataccagga gacaataagc aggctatgtc agaagcattc tatttctata ctttgagatg | 1260 |
| ctctgaagag gatttgagtg aagatcagaa aattgtctcc aacagtcaga catcaacaga | 1320 |
| agatcctggg gactccactc cctttgaaga ctcagaggaa ttttgtttca gtgctgaagc | 1380 |
| aaccagtttt gatggtgacg atgaatttga cacctacaat gaagatgatg aagatgacga | 1440 |
| gtctgtaacc ggctactgga taacatgttg ccctacttgt gatgttgaca tcaatacctg | 1500 |
| ggttccgttc tattcaacgg agctcaataa acccgccatg atctattgtt ctcatgggga | 1560 |
| tgggcactgg gtacatgccc agtgcatgga tttggaagaa cgcacactca tccacttgtc | 1620 |
| agaaggaagc aacaagtatt attgcaatga acatgtacag atagcaagag cattgcaaac | 1680 |
| tcccaaaaga aaccccccct tacaaaaacc tccaatgaaa tccctccaca aaaaggctc | 1740 |
| tgggaaagtc ttgactcctg ccaagaaatc cttccttaga agactgtttg attaatttag | 1800 |
| caaaagcccc tcagactcag gtatattgct ctctgaatct actttcaatc ataaacatta | 1860 |
| ttttgatttt tgtttactga aatctctatg ttatgtttta gttatgtgaa ttaagtgctg | 1920 |
| ttgtgattta ttgttaagta taactattct aatgtgtgtt tttaacatc ttatccagga | 1980 |
| atgtcttaaa tgagaaatgt tatacagttt tccattaagg atatcagtga taaagtatag | 2040 |
| aactcttaca ttatttgta acaatctaca tattgaatag taactaaata ccaataaata | 2100 |
| aactaatgca caaaaagtta agttcttttg tgtaataagt agcctatagt tggtttaaac | 2160 |
| agttaaaacc aacagctata tcccacacta ctgctgttta taaattttaa ggtggcctct | 2220 |
| ggtttatact tatgagcaga attatatata ttggtcaata ccatgaagaa aaattaatt | 2280 |
| ctatatcaag ccaggcatgg tgatggtgat acatgcctgt aatcctggca cttaggaagt | 2340 |
| ggaagaagga agttgtgag tttgatgctt gttgaggtat gaccttttgc tatgtattgt | 2400 |
| agtgtatgag ccccaagacc tgcttgaccc agagacaaga gagtccacac atagatccaa | 2460 |
| gtaatgctat gtgaccttgc ccccggtta cttgtgatta ggtgaataaa gatgtcaaca | 2520 |
| gccaatagct gggcagaaga gccaaaagtg gggattgagg gtaccctggc ttgatgtagg | 2580 |
| aggagaccat gaggaaaggg gagaaaaaag tgatggagga ggaaaagat gccatgagct | 2640 |
| aggagttaag aaagcatggc catgagtgct ggccaattgg agttaagagc agcccagatg | 2700 |

```
aaacatagta agtaataact cagggttatc gatagaaaat agattttagt gccgtactct    2760 cccccagccct agagctgact atggcttact gtaaatataa agtttgtatg tgtctttat     2820 ccaggaacta aatggtcaaa ggtggagtag aaactctgga ttgggattaa attttctac     2880 aacaaatgct ggcctgggct agattttatc tcatatccga aggctgacag aacacagagc    2940
actggtaaca ttgccacctg ccatgcacaa agacctgagt ctaatactgt ggacattttc    3000
ttgaagtatc tacatgtact tctggagtga aacatattc caacaatatg cctttgttta    3060
aatcactcac tcactttggg ccctcacatt atatcctttc aaaatcaatg gttcacccct    3120
ttgaaaatgc ttagccatag tccctcatct tccttaaaga cagttgtcat ctctggaaat    3180
agtcacatgt cattcaaggt ccaatactgt gcagctctga agtatggcat taccactta    3240 agtgaaaagt gaaatatgaa catgagctca gacaaaggtt tgggactatc actctcaagg    3300
aggctctact gctaagtcct gaactgcttt cacatgaata cagaaattat aacaaaaat    3360 atgtaatcaa taaaaagaaa actttcatat tcc                                  3393
```

<210> SEQ ID NO 35
<211> LENGTH: 527
<212> TYPE: PRT
<213> ORGANISM: Mus musculus

<400> SEQUENCE: 35

```
Met Ser Leu Gln Met Val Thr Val Gly His Asn Ile Ala Leu Ile Gln
1               5                   10                  15

Pro Gly Phe Ser Leu Met Asn Phe Asp Gly Gln Val Phe Phe Phe Gly
            20                  25                  30

Gln Lys Gly Trp Pro Lys Arg Ser Cys Pro Thr Gly Val Phe His Phe
        35                  40                  45

Asp Ile Lys Gln Asn His Leu Lys Leu Lys Pro Ala Ile Phe Ser Lys
    50                  55                  60

Asp Ser Cys Tyr Leu Pro Pro Leu Arg Tyr Pro Ala Thr Cys Ser Tyr
65                  70                  75                  80

Lys Gly Ser Ile Asp Ser Asp Lys His Gln Tyr Ile Ile His Gly Gly
                85                  90                  95

Lys Thr Pro Asn Asn Glu Leu Ser Asp Lys Ile Tyr Ile Met Ser Val
            100                 105                 110

Ala Cys Lys Asn Asn Lys Lys Val Thr Phe Arg Cys Thr Glu Lys Asp
        115                 120                 125

Leu Val Gly Asp Val Pro Glu Pro Arg Tyr Gly His Ser Ile Asp Val
    130                 135                 140

Val Tyr Ser Arg Gly Lys Ser Met Gly Val Leu Phe Gly Gly Arg Ser
145                 150                 155                 160

Tyr Met Pro Ser Thr Gln Arg Thr Thr Glu Lys Trp Asn Ser Val Ala
                165                 170                 175

Asp Cys Leu Pro His Val Phe Leu Ile Asp Phe Glu Phe Gly Cys Ala
            180                 185                 190

Thr Ser Tyr Ile Leu Pro Glu Leu Gln Asp Gly Leu Ser Phe His Val
        195                 200                 205

Ser Ile Ala Arg Asn Asp Thr Val Tyr Ile Leu Gly Gly His Ser Leu
    210                 215                 220

Ala Ser Asn Ile Arg Pro Ala Asn Leu Tyr Arg Ile Arg Val Asp Leu
225                 230                 235                 240

Pro Leu Gly Thr Pro Ala Val Asn Cys Thr Val Leu Pro Gly Gly Ile
```

```
                    245                 250                 255
        Ser Val Ser Ser Ala Ile Leu Thr Gln Thr Asn Asn Asp Glu Phe Val
                260                 265                 270

Ile Val Gly Gly Tyr Gln Leu Glu Asn Gln Lys Arg Met Val Cys Ser
                275                 280                 285

Leu Val Ser Leu Gly Asp Asn Thr Ile Glu Ile Ser Glu Met Glu Thr
                290                 295                 300

Pro Asp Trp Thr Ser Asp Ile Lys His Ser Lys Ile Trp Phe Gly Ser
        305                 310                 315                 320

Asn Met Gly Asn Gly Thr Ile Phe Leu Gly Ile Pro Gly Asp Asn Lys
                        325                 330                 335

Gln Ala Met Ser Glu Ala Phe Tyr Phe Tyr Thr Leu Arg Cys Ser Glu
                        340                 345                 350

Glu Asp Leu Ser Glu Asp Gln Lys Ile Val Ser Asn Ser Gln Thr Ser
                        355                 360                 365

Thr Glu Asp Pro Gly Asp Ser Thr Pro Phe Glu Asp Ser Glu Glu Phe
                370                 375                 380

Cys Phe Ser Ala Glu Ala Thr Ser Phe Asp Gly Asp Asp Glu Phe Asp
        385                 390                 395                 400

Thr Tyr Asn Glu Asp Asp Glu Asp Glu Ser Val Thr Gly Tyr Trp
                        405                 410                 415

Ile Thr Cys Cys Pro Thr Cys Asp Val Asp Ile Asn Thr Trp Val Pro
                        420                 425                 430

Phe Tyr Ser Thr Glu Leu Asn Lys Pro Ala Met Ile Tyr Cys Ser His
                        435                 440                 445

Gly Asp Gly His Trp Val His Ala Gln Cys Met Asp Leu Glu Glu Arg
                450                 455                 460

Thr Leu Ile His Leu Ser Glu Gly Ser Asn Lys Tyr Tyr Cys Asn Glu
        465                 470                 475                 480

His Val Gln Ile Ala Arg Ala Leu Gln Thr Pro Lys Arg Asn Pro Pro
                        485                 490                 495

Leu Gln Lys Pro Pro Met Lys Ser Leu His Lys Lys Gly Ser Gly Lys
                        500                 505                 510

Val Leu Thr Pro Ala Lys Lys Ser Phe Leu Arg Arg Leu Phe Asp
                515                 520                 525

<210> SEQ ID NO 36
<211> LENGTH: 1810
<212> TYPE: DNA
<213> ORGANISM: Homo sapiens

<400> SEQUENCE: 36
gagaccaaaa gtcaggtagg agcctccggg gtccctgctg tgtcacccgg acaggccgtg      60
ggggcgggca ggggggcggg gccgggcctg accacagcgg ccgagttcag tcctgctctc    120
cgcacgccac cttaggcccg cagccgtgcc gggtgctctt cagcatgtcc ttcatcccgg    180
tggccgagga ttccgacttc cccatccaca acctgcccta cggcgtcttc tcgaccagag    240
gcgacccaag accgaggata ggtgtggcca ttggcgacca gatcctggac ctcagcatca    300
tcaagcacct ctttactggt cctgtcctct ccaaacacca ggatgtcttc aatcagccta    360
cactcaacag cttcatgggc ctgggtcagg ctgcctggaa ggaggcgaga gtgttcttgc    420
agaacttgct gtctgtgagc caagccaggc tcagagatga caccgaactt cggaagtgtg    480
cattcatctc ccaggcttct gccacgatgc accttccagc caccatagga gactacacag    540
```

```
acttctattc ctctcggcag catgctacca acgtcggaat catgttcagg gacaaggaga    600
atgcgttgat gccaaattgg ctgcacttac cagtgggcta ccatggccgt gcctcctctg    660
tcgtggtgtc tggcacccca atccgaaggc ccatgggaca tgaaacct gatgactcta      720
agcctcccgt atatggtgcc tgcaagctct tggacatgga gctggaaatg gctttttttg    780
taggccctgg aaacagattg ggagagccga tccccatttc aaggcccat gagcacattt     840
ttggaatggt ccttatgaac gactggagtg cacgagacat tcagaagtgg gagtatgtcc    900
ctctcgggcc attccttggg aagagttttg ggaccactgt ctctccgtgg gtggtgccca    960
tggatgctct catgcccttt gctgtgccca cccgaagca ggaccccagg ccctgccgt     1020
atctgtgcca tgacgagccc tacacatttg acatcaacct ctctgttaac ctgaaaggag   1080
aaggaatgag ccaggcggct accatatgca agtccaattt taagtacatg tactggacga   1140
tgctgcagca gctcactcac cactctgtca acggctgcaa cctgcggccg ggggacctcc   1200
tggcttctgg gaccatcagc gggccggagc cagaaaactt cggctccatg ttggaactgt   1260
cgtggaaggg aacgaagccc atagacctgg ggaatggtca gaccaggaag tttctgctgg   1320
acggggatga agtcatcata acagggtact gccaggggga tggttaccgc atcggctttg   1380
gccagtgtgc tggaaaagtg ctgcctgctc tcctgccatc atgagatttt ctctgctctt   1440
ctggaaacaa agggctcaag caccccttc aaccctgtga ctggggtcct ccctcgggct   1500
gtaggcctgg tccgccattc agtgacaaat aaagccattg tgctctgagg cctgcactgc   1560
cgcagatgca gctgtgtcca cttatgatcg tgatttgatc cagtgggtca aggtgtgtaa   1620
agcctccctg ccagatattc attaatatgt tttctcactc ttattagtga ggtcaggggt   1680
ctttgtggga ttttcttatt agacatccca ggcctcctgg tattccatgg aatttgaaaa   1740
gagactggca cctgtagtag tcagggctct ccagagaaat agaaccaagg agaaagaaaa   1800
aaaaaaaaaa                                                          1810
```

<210> SEQ ID NO 37
<211> LENGTH: 419
<212> TYPE: PRT
<213> ORGANISM: Homo sapiens

<400> SEQUENCE: 37

```
Met Ser Phe Ile Pro Val Ala Glu Asp Ser Asp Phe Pro Ile His Asn
1               5                   10                  15

Leu Pro Tyr Gly Val Phe Ser Thr Arg Gly Asp Pro Arg Pro Arg Ile
            20                  25                  30

Gly Val Ala Ile Gly Asp Gln Ile Leu Asp Leu Ser Ile Lys His
        35                  40                  45

Leu Phe Thr Gly Pro Val Leu Ser Lys His Gln Asp Val Phe Asn Gln
    50                  55                  60

Pro Thr Leu Asn Ser Phe Met Gly Leu Gly Gln Ala Ala Trp Lys Glu
65                  70                  75                  80

Ala Arg Val Phe Leu Gln Asn Leu Leu Ser Val Ser Gln Ala Arg Leu
                85                  90                  95

Arg Asp Asp Thr Glu Leu Arg Lys Cys Ala Phe Ile Ser Gln Ala Ser
            100                 105                 110

Ala Thr Met His Leu Pro Ala Thr Ile Gly Asp Tyr Thr Asp Phe Tyr
        115                 120                 125

Ser Ser Arg Gln His Ala Thr Asn Val Gly Ile Met Phe Arg Asp Lys
    130                 135                 140
```

Glu Asn Ala Leu Met Pro Asn Trp Leu His Leu Pro Val Gly Tyr His
145                 150                 155                 160

Gly Arg Ala Ser Ser Val Val Val Ser Gly Thr Pro Ile Arg Arg Pro
            165                 170                 175

Met Gly Gln Met Lys Pro Asp Asp Ser Lys Pro Val Tyr Gly Ala
            180                 185                 190

Cys Lys Leu Leu Asp Met Glu Leu Glu Met Ala Phe Phe Val Gly Pro
            195                 200                 205

Gly Asn Arg Leu Gly Glu Pro Ile Pro Ile Ser Lys Ala His Glu His
            210                 215                 220

Ile Phe Gly Met Val Leu Met Asn Asp Trp Ser Ala Arg Asp Ile Gln
225                 230                 235                 240

Lys Trp Glu Tyr Val Pro Leu Gly Pro Phe Leu Gly Lys Ser Phe Gly
                245                 250                 255

Thr Thr Val Ser Pro Trp Val Pro Met Asp Ala Leu Met Pro Phe
            260                 265                 270

Ala Val Pro Asn Pro Lys Gln Asp Pro Arg Pro Leu Pro Tyr Leu Cys
            275                 280                 285

His Asp Glu Pro Tyr Thr Phe Asp Ile Asn Leu Ser Val Asn Leu Lys
290                 295                 300

Gly Glu Gly Met Ser Gln Ala Ala Thr Ile Cys Lys Ser Asn Phe Lys
305                 310                 315                 320

Tyr Met Tyr Trp Thr Met Leu Gln Gln Leu Thr His His Ser Val Asn
                325                 330                 335

Gly Cys Asn Leu Arg Pro Gly Asp Leu Leu Ala Ser Gly Thr Ile Ser
            340                 345                 350

Gly Pro Glu Pro Glu Asn Phe Gly Ser Met Leu Glu Leu Ser Trp Lys
            355                 360                 365

Gly Thr Lys Pro Ile Asp Leu Gly Asn Gly Gln Thr Arg Lys Phe Leu
            370                 375                 380

Leu Asp Gly Asp Glu Val Ile Ile Thr Gly Tyr Cys Gln Gly Asp Gly
385                 390                 395                 400

Tyr Arg Ile Gly Phe Gly Gln Cys Ala Gly Lys Val Leu Pro Ala Leu
                405                 410                 415

Leu Pro Ser

<210> SEQ ID NO 38
<211> LENGTH: 1597
<212> TYPE: DNA
<213> ORGANISM: Mus musculus

<400> SEQUENCE: 38
gggtgctaaa agaatcacta gggtggggag gcggtcccag tggggcgggt aggggtgtgt     60
gccaggtggt accgggtatt ggctggagga aagggcagccc ggggttcggg gcggtccctg    120
aatctaaagg ccctcggcta gtctgatcct tgccctaagc atagtcccgt tagccaaccc    180
cctacccgcc gtgggctctg ctgccggtg ctcgtcagca tgtcctttat tccagtggcc     240
gaggactccg actttcccat ccaaaacctg ccctatggtg ttttctccac tcaaagcaac    300
ccaaagccac ggattggtgt agccatcggt gaccagatct tggacctgag tgtcattaaa    360
cacctcttta ccggacctgc cctttccaaa catcaacatg tcttcgatga caactctc      420 aataacttca tgggtctggg tcaagctgca tggaaggagg caagagcatc cttacagaac    480
ttactgtctg ccagccaagc ccggctcaga gatgacaagg agcttcggca gcgtgcattc    540

```
acctcccagg cttctgcgac aatgcacctt cctgctacca taggagacta cacggacttc    600
tactcttctc ggcagcatgc caccaatgtt ggcattatgt tcagaggcaa ggagaatgcg    660
ctgttgccaa attggctcca cttacctgtg ggataccatg gccgagcttc ctccattgtg    720
gtatctggaa ccccgattcg aagacccatg gggcagatga gacctgataa ctcaaagcct    780
cctgtgtatg gtgcctgcag actcttagac atggagttgg aaatggcttt cttcgtaggc    840
cctgggaaca gattcggaga gccaatcccc atttccaaag cccatgaaca cattttcggg    900
atggtcctca tgaacgactg gagcgcacga gacatccagc aatgggagta cgtcccactt    960
gggccattcc tggggaaaag ctttggaacc acaatctccc cgtgggtggt gcctatggat   1020
gccctcatgc cctttgtggt gccaaaccca agcaggaccc caagcccttg ccatatctc    1080
tgccacagcc agcccctacac atttgatatc aacctgtctg tctctttgaa aggagaagga   1140
atgagccagg cggctaccat ctgcaggtct aactttaagc acatgtactg gaccatgctg   1200
cagcaactca cacaccactc tgttaatgga tgcaacctga gacctgggga cctcttggct   1260
tctggaacca tcagtggatc agaccctgaa agctttggct ccatgctgga actgtcctgg   1320
aagggaacaa aggccatcga tgtggagcag gggcagacca ggaccttcct gctggacggc   1380
gatgaagtca tcataacagg tcactgccag ggggacggct accgtgttgg ctttggccag   1440
tgtgctggga agtgctgcc tgcccttttca ccagcctgaa gctccggaag tcacaagaca   1500
cacccttgcc ttatgaggat catgctacca ctgcatcagt caggaatgaa taaagctact   1560
ttgattgtgg gaaatgccac agaaaaaaaa aaaaaaa                             1597
```

<210> SEQ ID NO 39
<211> LENGTH: 419
<212> TYPE: PRT
<213> ORGANISM: Mus musculus

<400> SEQUENCE: 39

Met Ser Phe Ile Pro Val Ala Glu Asp Ser Asp Phe Pro Ile Gln Asn
1               5                   10                  15

Leu Pro Tyr Gly Val Phe Ser Thr Gln Ser Asn Pro Lys Pro Arg Ile
            20                  25                  30

Gly Val Ala Ile Gly Asp Gln Ile Leu Asp Leu Ser Val Ile Lys His
        35                  40                  45

Leu Phe Thr Gly Pro Ala Leu Ser Lys His Gln His Val Phe Asp Glu
    50                  55                  60

Thr Thr Leu Asn Asn Phe Met Gly Leu Gly Gln Ala Ala Trp Lys Glu
65                  70                  75                  80

Ala Arg Ala Ser Leu Gln Asn Leu Leu Ser Ala Ser Gln Ala Arg Leu
                85                  90                  95

Arg Asp Asp Lys Glu Leu Arg Gln Arg Ala Phe Thr Ser Gln Ala Ser
            100                 105                 110

Ala Thr Met His Leu Pro Ala Thr Ile Gly Asp Tyr Thr Asp Phe Tyr
        115                 120                 125

Ser Ser Arg Gln His Ala Thr Asn Val Gly Ile Met Phe Arg Gly Lys
    130                 135                 140

Glu Asn Ala Leu Leu Pro Asn Trp Leu His Leu Pro Val Gly Tyr His
145                 150                 155                 160

Gly Arg Ala Ser Ser Ile Val Val Ser Gly Thr Pro Ile Arg Arg Pro
                165                 170                 175

Met Gly Gln Met Arg Pro Asp Asn Ser Lys Pro Val Tyr Gly Ala
            180                 185                 190

Cys Arg Leu Leu Asp Met Glu Leu Glu Met Ala Phe Phe Val Gly Pro
        195                 200                 205

Gly Asn Arg Phe Gly Glu Pro Ile Pro Ile Ser Lys Ala His Glu His
    210                 215                 220

Ile Phe Gly Met Val Leu Met Asn Asp Trp Ser Ala Arg Asp Ile Gln
225                 230                 235                 240

Gln Trp Glu Tyr Val Pro Leu Gly Pro Phe Leu Gly Lys Ser Phe Gly
                245                 250                 255

Thr Thr Ile Ser Pro Trp Val Val Pro Met Asp Ala Leu Met Pro Phe
            260                 265                 270

Val Val Pro Asn Pro Lys Gln Asp Pro Lys Pro Leu Pro Tyr Leu Cys
        275                 280                 285

His Ser Gln Pro Tyr Thr Phe Asp Ile Asn Leu Ser Val Ser Leu Lys
    290                 295                 300

Gly Glu Gly Met Ser Gln Ala Ala Thr Ile Cys Arg Ser Asn Phe Lys
305                 310                 315                 320

His Met Tyr Trp Thr Met Leu Gln Gln Leu Thr His His Ser Val Asn
                325                 330                 335

Gly Cys Asn Leu Arg Pro Gly Asp Leu Leu Ala Ser Gly Thr Ile Ser
            340                 345                 350

Gly Ser Asp Pro Glu Ser Phe Gly Ser Met Leu Glu Leu Ser Trp Lys
        355                 360                 365

Gly Thr Lys Ala Ile Asp Val Glu Gln Gly Gln Thr Arg Thr Phe Leu
    370                 375                 380

Leu Asp Gly Asp Glu Val Ile Ile Thr Gly His Cys Gln Gly Asp Gly
385                 390                 395                 400

Tyr Arg Val Gly Phe Gly Gln Cys Ala Gly Lys Val Leu Pro Ala Leu
                405                 410                 415

Ser Pro Ala

<210> SEQ ID NO 40
<211> LENGTH: 72
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Il2-rg WT-guide RNA

<400> SEQUENCE: 40
tccaaggtcc tcatgtccag tgcgaatgaa gacatcaagc ttatccctgt tggcacatgg      60
ggttgattat ta                                                         72

<210> SEQ ID NO 41
<211> LENGTH: 17
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Il2-rg genomic deletion

<400> SEQUENCE: 41
tccaaggttg attatta                                                    17

<210> SEQ ID NO 42

```
<211> LENGTH: 54
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rag2 WT- guide RNA

<400> SEQUENCE: 42
ccagatacgg ccattccatt gacgtggcct gggttccgtt ctattcaacg gagc        54

<210> SEQ ID NO 43
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rag2 gene Deletion-1 guide RNA

<400> SEQUENCE: 43
ccagatacgg ccattccatt ctattcaacg gagc        34

<210> SEQ ID NO 44
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rag2 genomic Deletion-2 guide RNA

<400> SEQUENCE: 44
ccagatacgg ccattcaacg gagc        24

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rag2 genomic Deletion-3 guide RNA

<400> SEQUENCE: 45
aagttactat tcaacggagc        20

<210> SEQ ID NO 46
<211> LENGTH: 26
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rag2 genomic Deletion-4 guide RNA

<400> SEQUENCE: 46
ccagatacgg ccatattcaa cggagc        26

<210> SEQ ID NO 47
<211> LENGTH: 52
<212> TYPE: DNA
<213> ORGANISM: Artificial Sequence
<220> FEATURE:
```

<223> OTHER INFORMATION: Synthetic polynucleotide

<400> SEQUENCE: 47
gtgcccctga ttctgtttca gtgcattatg ttgggcatta tgttcagagg ca            52

<210> SEQ ID NO 48
<211> LENGTH: 52
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Fah genomic Deletion-1 guide RNA

<400> SEQUENCE: 48
gtgcccctga ttctgtttca gtgcattatg ttgggcatta tgttcagagg ca            52

<210> SEQ ID NO 49
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Fah genomic Deletion-2 guide RNA

<400> SEQUENCE: 49
gtgcccctga ttctgtttca gtgcattatg ttcagaggca                          40

<210> SEQ ID NO 50
<211> LENGTH: 47
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: Il2rg-/- Del-1, Frame shift mutation from
      aminoacid 28

<400> SEQUENCE: 50

Leu Cys Trp His Tyr Val Gln Arg Gln Gly Glu Cys Ala Val Ala Lys
1               5                   10                  15

Leu Ala Pro Leu Thr Cys Gly Ile Pro Trp Pro Ser Phe Leu His Cys
            20                  25                  30

Gly Ile Trp Asn Pro Asp Ser Lys Thr His Gly Ala Asp Glu Thr
        35                  40                  45

<210> SEQ ID NO 51
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rag2-/- Del-1; Frame shift from aminoacid 143

<400> SEQUENCE: 51

Ile Leu Phe Asn Gly Ala Gln
1               5

<210> SEQ ID NO 52
<211> LENGTH: 9
<212> TYPE: PRT

```
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rag2-/- Del-2; Frame shift from aminoacid 141

<400> SEQUENCE: 52

Ile Gln Arg Ser Ser Ile Asn Pro Pro
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rag2-/- Del-3; Frame shift from aminoacid 122

<400> SEQUENCE: 53

Ile Gln Arg Ser Ser Ile Asn Pro Pro
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Rag2-/- Del-4; Frame shift from aminoacid 142

<400> SEQUENCE: 54

Thr Lys Lys Ala Leu Gly Lys Ser
1               5

<210> SEQ ID NO 55
<211> LENGTH: 47
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Fah-/- Del-1; Frame shift from aminoacid 107

<400> SEQUENCE: 55

Leu Cys Trp His Tyr Val Gln Arg Gln Gly Glu Cys Ala Val Ala Lys
1               5                   10                  15

Leu Ala Pro Leu Thr Cys Gly Ile Pro Trp Pro Ser Phe Leu His Cys
            20                  25                  30

Gly Ile Trp Asn Pro Asp Ser Lys Thr His Gly Ala Asp Glu Thr
        35                  40                  45

<210> SEQ ID NO 56
<211> LENGTH: 40
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Fah-/- Del-2; Frame shift from aminoacid 107

<400> SEQUENCE: 56
```

-continued

```
Leu Cys Ser Glu Ala Arg Arg Met Arg Cys Cys Gln Ile Gly Ser Thr
1               5                   10                  15

Tyr Leu Trp Asp Thr Met Ala Glu Leu Pro Pro Leu Trp Leu Glu Pro
            20              25                  30

Arg Phe Glu Asp Pro Trp Gly Arg
        35              40
```

HUMAN LIVER CHIMERIC MOUSE WITH DEFICIENT P450 OXIDOREDUCTASE

CROSS-REFERENCE TO RELATED APPLICATIONS

This application is a National Stage Application, filed under 35 U.S.C. 371, of International Application No. PCT/US2017/039474, filed on Jun. 27, 2017, which claims priority to, and the benefit of, U.S. Provisional Application No. 62/355,102, filed on Jun. 27, 2016 and U.S. Provisional Application No. 62/509,942, filed on May 23, 2017. The entire content of each of these applications is incorporated herein by reference in their entireties.

INCORPORATION BY REFERENCE OF SEQUENCE LISTING

The contents of the text file named AVCR-001N01US_Sequence_Listing which was created on Dec. 13, 2018 and is 68 KB in size are hereby incorporated by reference in their entirety.

BACKGROUND OF THE INVENTION

Only one out often drugs in development gets approved for clinical use. The majority fails during clinical trials due to inefficacy or toxicity in humans. The lack of experimental animal models to accurately predict human xenobiotic metabolism is a significant limitation, which jeopardizes human lives and drives drug development costs. Hence, there is a compelling need to develop better preclinical tools. The present disclosure solves these needs in the art by providing a human liver chimeric non-human animal model and methods of using the human liver chimeric non-human animal model to predict human specific drug metabolism.

SUMMARY OF THE INVENTION

The present disclosure provides a method for preparing a chimeric non-human animal comprising human hepatocytes, the method comprising: (a) providing a non-human animal comprising a reduction or deletion of NADPH-P450 oxidoreductase (Por) gene resulting in reduced or absent expression of Por protein; and (b) transplanting human hepatocytes into the non-human animal.

The non-human animal can comprise reducing or deleting the Por gene resulting in reduced or absent expression of Por protein. The reduced or deleted Por gene can be a conditional knockdown or knockout of the Por gene. The reduced or deleted Por gene can be the result of a mutation, a transgene, treatment with an exogenous substance or somatic genome engineering, including a CRISPR (Clustered regularly interspaced short palindromic repeats) system. The somatic genome engineering comprises Guide RNA (gRNA) and Caspase 9 (Cas9).

The non-human animal can comprise a floxed allele of the Por gene, and wherein the non-human animal is provided with a Cre recombinase sufficient to produce a conditional knockout of the Por gene. The non-human animal comprising the floxed allele of the Por gene can be provided with at least a first dose of a virus that encodes Cre recombinase. The non-human animal can be provided with at least a second dose of a virus that encodes Cre recombinase. The non-human animal can comprise the floxed allele of the Por gene is crossed with a transgenic non-human animal strain expressing Cre recombinase.

In a one aspect, the method of the present disclosure comprises (a) providing a non-human animal comprising a floxed allele of the Por gene with a first does of a virus that encodes Cre recombinase; (b) transplanting human hepatocytes into the non-human animal; and (c) providing the non-human animal with a second dose of a virus that encodes Cre recombinase. Steps (a) and (b) can occur sequentially or simultaneously.

The non-human animal can further comprise a reduction or deletion of at least one additional gene encoding an enzyme involved in drug metabolism. The at least one additional enzyme can be a phase II drug enzyme. In one aspect, the non-human animal can further comprise a reduction or deletion of UDP-glucose 6-dehydrogenase (UGDH) gene, a reduction or deletion of Glutathione synthetase (GSS) gene, or a combination thereof.

The reduction or deletion the UGDH gene can result in reduced or absent expression of UGDH protein. The reduction or deletion the GSS gene can result in reduced or absent expression of GSS protein. The reduced or deleted UGDH gene can be a conditional knockdown or knockout of the UGDH gene. The reduced or deleted GSS gene can be a conditional knockdown or knockout of the GSS gene. The reduced or deleted UGDH or GSS gene can be the result of a mutation, a transgene, treatment with an exogenous substance or somatic genome engineering, including a CRISPR (Clustered regularly interspaced short palindromic repeats) system. The somatic genome engineering comprises Guide RNA (gRNA) and Caspase 9 (Cas9).

The non-human animal can be selected from the group consisting of primate, bird, mouse, rat, fowl, dog, cat, cow, horse, goat, camel, sheep and pig. In a preferred aspect, the non-human animal is a mouse.

The non-human animal comprising a reducing or deleting the Por gene can be selected from the group consisting of (i) the FRG (Fah$^{-/-}$/Rag2$^{-/-}$/Il2rg$^{-/-}$) non-human animal, (ii) a transgenic urokinase type plasminogen activator (uPA) non-human animal, which overexpress uPA under an inducible promoter, preferably a liver-restricted albumin promoter, (iii) the thymidine kinase-NOD/Shi-scid/IL-2R$\gamma^{null}$ (TK-NOG) non-human animal, which is a immunodeficient NOG non-human animal with transgenic expression of thymidine kinase under control of liver-restricted promoter, (iv) a non-human animal expressing an inducible Caspase 8 in the liver, and (v) a non-human animal expressing an inducible Caspase 9 in the liver.

The present disclosure also provides a chimeric non-human animal, offspring thereof, or a portion thereof, which has a chimeric liver comprising human hepatocytes, prepared by any method disclosed herein.

The chimeric non-human animal can be immunodeficient. The chimeric non-human animal substantially lacks autogenous hepatocytes. Human hepatocytes can account for any percentage of human chimerism greater than about 1%, for example at least 5%, at least 10%, at least 20%, at least 30%, at least 40%, at least 50%, at least 60%, at least 70%, at least 80%, at least 90%, at least 95% or at least 99% of all hepatocytes in the chimeric liver of the chimeric non-human animal. A "non-human animal" can be amphibian, reptile, avian, or a non-human mammal. The non-human animal can be e.g., any non-human mammal, e.g., primate, bird, mouse, rat, fowl, dog, cat, cow, horse, goat, camel, sheep or pig. In a preferred aspect, the non-human animal is a mouse.

In one aspect, the present disclosure provides a method for preparing a chimeric non-human animal comprising human hepatocytes, the method comprising steps of: (a) providing a non-human animal that allows its liver to be repopulated with human hepatocytes and comprising a non-functional NADPH-P450 oxidoreductase generated either by genome engineering or knockdown with exogenous agents such as genome engineering tools like CRISPR/Cas9 or floxed allele of the NADPH-P450 oxidoreductase (Por) gene with a first dose of a virus that encodes Cre recombinase or a Cre transgenic animal, thereby producing a conditional knockout of the Por gene; (b) transplanting human hepatocytes into the non-human animal; and (c) providing the non-human animal with a second dose of the virus that encodes Cre recombinase. The chimeric non-human animal can substantially lack autogenous or endogenous hepatocytes and instead comprising human hepatocytes. Steps (a) and (b) can occur sequentially or simultaneously. Any non-human animal comprising mutations and/or transgenes that allow its liver to be repopulated with human hepatocytes may be used in combination with the floxed or deleted allele of the NADPH-P450 oxidoreductase (Por) gene or functional inactivation of the Por protein. In aspects, the non-human animal comprising mutations and/or transgenes that allow its liver to be repopulated with human hepatocytes is (i) the FRG (Fah$^{-/-}$/Rag2$^{-/-}$/Il2rg$^{-/-}$) non-human animal, (ii) a transgenic uPA non-human animal, which overexpress urokinase type plasminogen activator (uPA) in the liver under an inducible promoter and/or preferably a liver-restricted albumin promoter, (iii) the TK-NOG non-human animal, which is a immunodeficient NOG non-human animal with transgenic expression of thymidine kinase under control of liver-restricted albumin promoter, (iv) a non-human animal expressing an inducible Caspase 8 in the liver, or (v) a non-human animal expressing an inducible Caspase 9 in the liver (vi) a non-human animal expressing human heparin-binding epidermal growth factor-like receptor (HB-EGF)-like receptors under the control of a liver cell-specific albumin promoter (alb-TRECK). A "non-human animal" can be amphibian, reptile, avian, or a non-human mammal.

In one aspect, the present disclosure provides a method for preparing a chimeric mouse substantially lacking murine hepatocytes and instead comprising human hepatocytes, comprising steps of: (a) providing a mouse that allows its liver to be repopulated with human hepatocytes and comprising a non-functional NADPH-P450 oxidoreductase generated either by genome engineering by CRISPR/Cas9 mediated deletion or knockdown with exogenous agents or floxed allele of the NADPH-P450 oxidoreductase (Por) gene with a first dose of a virus that encodes Cre recombinase or a Cre transgenic mouse, thereby producing a conditional knockout of the Por gene; (b) transplanting human hepatocytes into the mouse; and (c) providing the mouse with a second dose of the virus that encodes Cre recombinase. Steps (a) and (b) can occur sequentially or simultaneously. Any mouse that allow its liver to be repopulated with human hepatocytes may be used in combination with the floxed allele of the NADPH-P450 oxidoreductase (Por) gene or somatic gene deletion or reduction or inactivation of the Por gene, respectively protein. In aspects, the mouse that allow its liver to be repopulated with human hepatocytes is (i) the FRG (Fah$^{-/-}$/Rag2$^{-/-}$/Il2rg$^{-/-}$) mouse, (ii) a transgenic uPA mouse, which overexpress urokinase type plasminogen activator (uPA) under an inducible promoter, preferably a liver-restricted albumin promoter, (iii) the TK-NOG mouse, which is a super immunodeficient NOG mouse with transgenic expression of thymidine kinase under control of liver-restricted albumin promoter, (iv) a mouse expressing an inducible Caspase 8 in the liver, (v) a mouse expressing an inducible Caspase 9 in the liver or (vi) a mouse expressing human heparin-binding epidermal growth factor-like receptor (HB-EGF)-like receptors under the control of a liver cell-specific albumin promoter (alb-TRECK).

The present disclosure also provides a method for screening and identifying metabolites for any type of drugs, typically small molecule drugs, that might affect human liver functions but also any other function of the body, comprising: (a) administering a test substance to the chimeric non-human animal of the present disclosure; (b) measuring one or more values in the chimeric non-human animal to which the test substance is administered in (a); and (c) selecting a test substance that causes an increase or an decrease in one or more values measured in (b), compared with the one or more values measured in a chimeric non-human animal to which no test substance is administered or a chimeric non-human animal without deletion of the Por gene or a non-human animals without human chimerism. Preferably, the one or more values are selected from but not limited to the group consisting of a metabolite of the test substance, human albumin concentration, body weight curve, liver-weight-to-body-weight ratio, total albumin level, total protein level, Alanine Aminotransferase (ALT) level, Aspartate Aminotransferase (AST) level, and total bilirubin level, creatinine, Blood Urea Nitrogen (BUN), troponine, blood count, TSH and histological assessment for pathologies in the human and non-human organs. A "non-human animal" can be amphibian, reptile, avian, or a non-human mammal. The non-human animal can be e.g., any non-human mammal, e.g., primate, bird, mouse, rat, fowl, dog, cat, cow, horse, goat, camel, sheep or pig. Preferably, the non-human animal is a mouse.

The present disclosure further provides a method for screening for a substance that affects human liver functions, comprising: (a) administering a test substance to the chimeric mouse of the present disclosure; (b) measuring one or more values in the chimeric mouse to which the test substance is administered in (a); and (c) selecting a test substance that causes an increase or an decrease in one or more values measured in (b), compared with the one or more values measured in a chimeric mouse to which no test substance is administered. Preferably, the one or more values is selected from the group consisting of a metabolite of the test substance, human albumin concentration, body weight curve, liver-weight-to-body-weight ratio, total albumin level, total protein level, ALT level, AST level, and total bilirubin level, histological assessment for pathologies in the human and non-human organs.

The present disclosure also provides a method for evaluating the toxicity of a test substance against human hepatocytes, comprising: (a) administering a test substance to the chimeric non-human animal of the present disclosure; (b) measuring one or more indicators in the chimeric non-human animal to which the test substance is administered in (a); and (c) evaluating the effect of the test substance on human hepatocytes using, one or more indicators measured in (b), compared with the one or more indicators measured in a chimeric non-human animal to which no test substance is administered. Preferably, the one or more indicators is selected from the group consisting of an increase or a decrease in any one or more of a metabolite of the test substance, human albumin concentration, body weight curve, liver-weight-to-body-weight ratio, total albumin level, total protein level, ALT level, AST level, and total bilirubin level, histological assessment for toxicity in the human and non-human organs. A "non-human animal" can be amphibian, reptile, avian, or a non-human mammal. The non-human animal can be e.g., any non-human mammal, e.g., primate, bird, mouse, rat, fowl, dog, cat, cow, horse, goat, camel, sheep or pig. Preferably, the non-human animal is a mouse.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and further features will be more clearly appreciated from the following detailed description when taken in conjunction with the accompanying drawings.

FIG. 1A-D shows the generation of the PIRF strain and deletion of the murine P450 (Por) oxidoreductase. FIG. 1A is a schematic representation of deleted and transgenic loci in the PIRF strain. FIG. 1B is a graph showing qPCR of Por mRNA upon intravenous injection of adenovirus expressing the CRE recombinase (Adeno-Cre). FIG. 1C is a series of immunostaining photographs for Por demonstrating a gradient across the hepatic acinus with higher pericentral (cv) and lower periportal (pv) expression. Upon injection with Adeno-CrePor is barely detectable. FIG. 1D is a photograph of a Western blot showing the almost complete disappearance of Por protein.

FIG. 2A is a series of immunostaining photographs showing humanized PIRF and FRG mice for murine Por (mPor) and human nuclei (hNuc) after injection of Adeno-Cre ($2.2 \times 10^{10}$ pfu/mouse) once (1×) or twice (2×). Counterstaining in merged picture using DAPI. FIG. 2B is a schematic showing the experimental outline for murine and human transcriptomics from chimeric livers with or without Por deletion. FIG. 2C is a graph showing the murine cytochrome mRNA originating from livers of the PIRF model. FIG. 2D is a graph showing the human cytochrome mRNA originating from livers of the PIRF model. FIG. 2E is a graph showing the comparison gene expression of the main drug metabolizing human cytochromes in humanized, Por-deleted PIRF (Hu-PIRF 2×) mice with the original, isogenic human hepatocytes. Gene expression has been normalized to three murine respectively human housekeeping genes (PSMB2, PSMB4 and RAB7A resp. Rab7[25]). PIRF; Por$^{c/c}$/Il2rg$^{-/-}$/Rag2$^{-/-}$, Fah$^{-/-}$FRG; Fah$^{-/-}$/Rag2$^{-/-}$/Il2rg$^{-/-}$.

FIG. 3A is a graph showing the selection of abundant and decreased gefitinib metabolites upon murine P450 oxidoreductase (Por) deletion in non-humanized PIRF mice using mass spectrometry in the murine feces within 24 hours after intravenous injection of gefitinib. FIG. 3B is a schematic showing gefitinib metabolites and know modifications. FIG. 3C is a graph showing that murine Por-deleted, human liver chimeric PIRF (Hu-PIRF 2×) mice and control groups show the most abundant human metabolite, M4. FIG. 3D is a graph showing that murine Por-deleted, human liver chimeric PIRF (Hu-PIRF 2×) mice and control groups show the human specific metabolite M28. PIRF; Por$^{c/c}$/Il2rg$^{-/-}$/Rag2$^{-/-}$, Fah$^{-/-}$, FRG; Fah$^{-/-}$/Rag2$^{-/-}$/Il2rg$^{-/-}$. * $p<0.05$ using non-parametric Mann-Whitney test. FIG. 3E is a graph is a graph showing a mass spectrometry analysis of PIRF liver homogenates 30 min after injection with atazanavir, a retroviral therapeutic. A major human metabolite (M15) is shown. The overall abundance of metabolites from atazanavir or gefitinib was set as 100% in each sample. The data are expressed as mean. PIRF; Por$^{c/c}$/Il2rg$^{-/-}$/Rag2$^{-/-}$/Fah$^{-/-}$, FRG; Fah$^{-/-}$/Rag2$^{-/-}$/Il2rg$^{-/-}$ * $p<0.05$ using non-parametric Mann-Whitney test.

FIG. 4A-B shows a schematic of an exemplary probe of the present disclosure. FIG. 4A is a schematic showing the design of the targeting vector and modified Por locus. FIG. 4B is a photograph of Southern blotting with three probes demonstrating proper targeting of ESC.

FIG. 6A shows a scheme of Il2 rg, Rag2 and Fah genes showing the gRNA location (in color) and the primers used to genotype the mice.

FIGS. 7A and 7B show the spectrum of genomic deletions in the Il2-rg, Rag2 and Fah gene. FIG. 7A is a schematic showing CRISPR/Cas9 injected zygotes of conditional Por–/– mice sequenced to determine of deletion of DNA. FIG. 7B is a schematic showing CRISPR/Cas9 injected zygotes of conditional Por–/– mice sequenced to determine of deletion of amino acids.

FIG. 11A shows that POR can be detected in immunofluorescence with the control group where only one allele carries a floxed POR sequence the other one the wild-type POR (POR$^{c/+}$). In FIG. 11B, both POR alleles are floxed (POR$^{c/c}$), leading to an almost complete deletion of the POR gene and a barely detectable POR protein. POR (green) and nuclei (blue, DAPI).

FIG. 12 depicts the expression of P450 oxidoreductase in humanized PIRF mice.

FIG. 13 depicts Gefitinib metabolites upon murine P450 oxidoreductase (Por) deletion.

FIG. 14 depicts the deletion of murine P450 oxidoreductase by crossing Por$^{c/c}$ with an Alb-Cre transgenic mouse.

FIG. 17A shows the use of a 5' probe, FIG. 17B shows the use of a 3' probe and FIG. 17C shows the use of a neomycin probe.

FIG. 20 is an H&E stain of liver lobe four weeks after transduction with adenovirus showing macro- and microvesicular steatosis. Left picture is a higher magnification of boxed area on right FIG. 21B. Single vector design: S aureus Cas9 and sgRNA can be delivered on the same AAV vector (4.85 kb). HA, HA-epitope.

FIG. 25A. Humanized FRG mice. FIG. 25B. Humanized FRG mice after murine Por and Ugdh deletion. FIG. 25C. Non-humanized FRG mice. FIG. 25D. Non-humanized FRG mice with Por and Ugdh genes deleted. Sulfate metabolites of troglitazone in red and glucuronide conjugates in blue.

DETAILED DESCRIPTION OF THE INVENTION

Figure 1B:
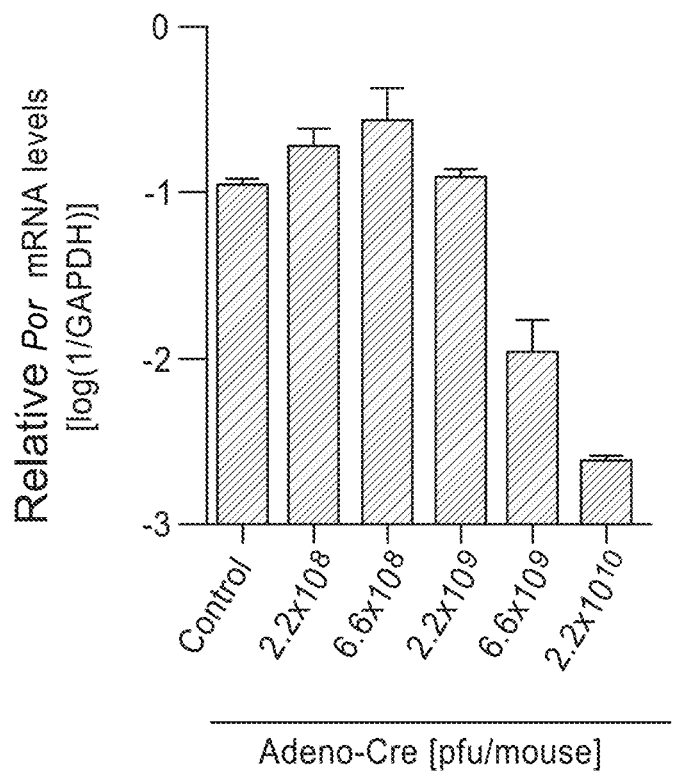

Human liver chimeric mice have been recently introduced to predict human xenobiotic metabolism and toxicity.

Despite their potential, the remaining murine liver, containing an expanded set of P450 cytochromes, makes it difficult to accurately predict human drug metabolism. Therefore, the present disclosure provides a conditional knock-out mouse of the NADPH-P450 oxidoreductase (Por) gene, which is the only electron donor for all murine cytochromes and if deleted, embryonically lethal, thereby allowing a functional inactivation of all murine cytochromes.

Any mouse comprising mutations and/or transgenes that allow its liver to be repopulated with human hepatocytes may be used in combination with the conditional knock-out allele or other genomic deletion of the NADPH-P450 oxidoreductase (Por) gene. In embodiments, the mouse comprising mutations and/or transgenes that allow its liver to be repopulated with human hepatocytes is (i) the FRG (Fah$^{-/-}$/Rag2$^{-/-}$/Il2rg$^{-/-}$) mouse, (ii) a transgenic uPA mouse, which overexpress urokinase type plasminogen activator (uPA) under an inducible promoter, preferably a liver-restricted albumin promoter, (iii) the TK-NOG mouse, which is a immunodeficient NOG mouse with transgenic expression of thymidine kinase under control of liver-restricted albumin promoter, (iv) a mouse expressing an inducible Caspase 8 in the liver, (v) a mouse expressing an inducible Caspase 9 in the liver or (vi) a mouse expressing human heparin-binding epidermal growth factor-like receptor (HB-EGF)-like receptors under the control of a liver cell-specific albumin promoter (alb-TRECK). Using such mice and an adenoviral or transgenic strategy expressing CRE, an almost complete deletion of the murine Por gene can be generated leading to an exclusive human cytochrome metabolism.

In the uPA-SCID mouse (Rhim et al 1994; Tateno et al. 2004), the genetic cause of mouse hepatocyte ablation is uroplasminogen activator (uPA); the mouse is in the SCID immune deficient background or Rag2 (or Rag1)–/– and/or Il2rg–/– all leading to the ability to transplant and engraft human hepatocytes.

In the FRG mouse (Azuma et al 2007[7], Bissig et al 2007[5]), the genetic cause of mouse hepatocyte ablation is fumarylacetoacetate hydrolase deficiency and mouse hepatocyte ablation is controlled by ±NTBC and/or ±low tyrosine diet; the mouse is in the Il2rg–/– and Rag2–/– background. The FRG mouse combines immune-deficiency-mediating mutations, in the recombination activating gene 2 (Rag2) and the gamma chain of the interleukin 2 receptor (Il2rg), with a functional knockout of the fumarylacetoacetate hydrolase (Fah) gene (Azuma et al 2007[7], Bissig et al 2007[5]). The latter gene codes for an enzyme in the tyrosine catabolic pathway and its mutation leads to an intracellular accumulation of a toxic inter-mediate in hepatocytes. Unlike the uPA/SCID model, the onset and severity of hepatocellular injury in FRG mice is controllable through the administration and withdrawal of the protective drug 2-(2-nitro-4-trifluoromethylbenzoyl)-1,3-cyclohexanedione (NTBC), which blocks an upstream enzyme in the tyrosine path-way and thereby prevents accumulation of the toxic intermediate.

In the TK-NOG mouse (Hasegawa et al 2011), the genetic cause of mouse hepatocyte ablation is the herpes simplex virus thymidine kinase and mouse hepatocyte ablation is controlled by ± ganciclovir; the mouse is in the Il2rg –/– and SCID background. Mouse hepatocyte ablation in this TK-NOG model was achieved through the liver-specific expression of the herpes simplex virus 1 thymidine kinase (HSVtk) in severely immunodeficient NOG mice and administration of ganciclovir (GCV), utilizing the fact that HSVtk converts the otherwise nontoxic GCV into a toxic intermediate.

In the AFC8 mouse (Washburn et al 2011), the genetic cause of mouse hepatocyte ablation is a FK508-capsae 8 fusion and mouse hepatocyte ablation is controlled by ±AP20187; the mouse is in the Il2rg–/– and Rag2–/– background.

In the Alb-TRECK/SCID mouse (Zhang et al 2015), the genetic cause of mouse hepatocyte ablation is the human heparin-binding EGF-like receptor and mouse hepatocyte ablation is controlled by ±Diphtheria toxin; the mouse is in the SCID immune deficient background.

Sheer and Wilson, 2015 compares major features of various different liver humanized models and process of liver reconstitution in the most frequently used models to date. This reference is incorporated by reference in its entirety.

The present disclosure also provides methods of utilizing the humanized, murine Por deficient mice to predict human drug metabolism. In an embodiment, the FRG mouse and the conditional Por–/– mouse was combined to generate the PIRF (Por–/– Il2rg–/–/Rag2–/–/Fah–/–) strain, which allows repopulation with human hepatocytes. Homozygous PIRF mice are fertile and can be repopulated with human hepatocytes generating high human chimerism (>80% human).

Human p450 cytochrome clusters contain 57 putatively functional genes and 58 pseudogenes, while the mouse cytochrome clusters are greatly expanded accounting for 102 putatively functional genes and 88 pseudogenes[2]. This makes accurate prediction of human drug metabolism in the mouse challenging. In addition hepatotoxicity together with hypersensitivity/cutaneous reactions have the poorest correlation with animal studies yet are the most common reasons for toxicity related termination of drugs in clinical development[3].

Figure 1C:
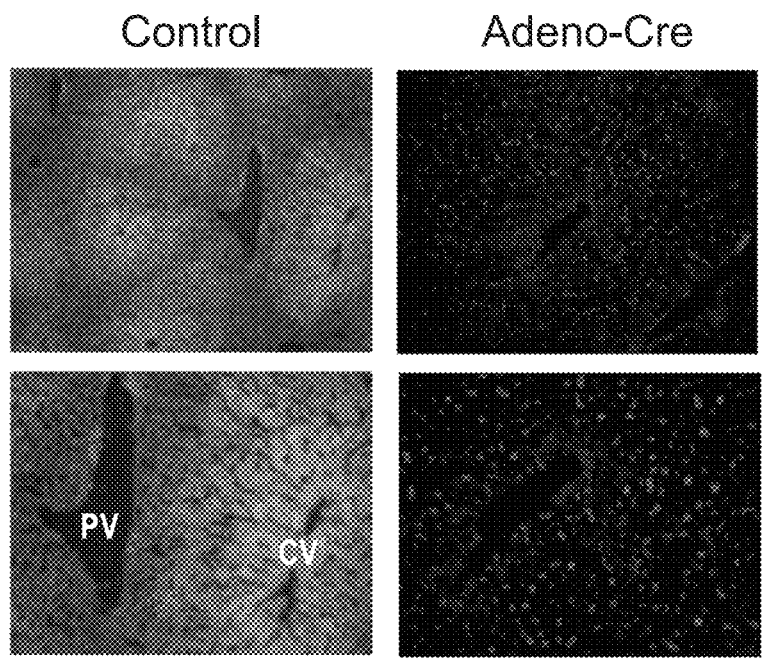
Figure 1D:
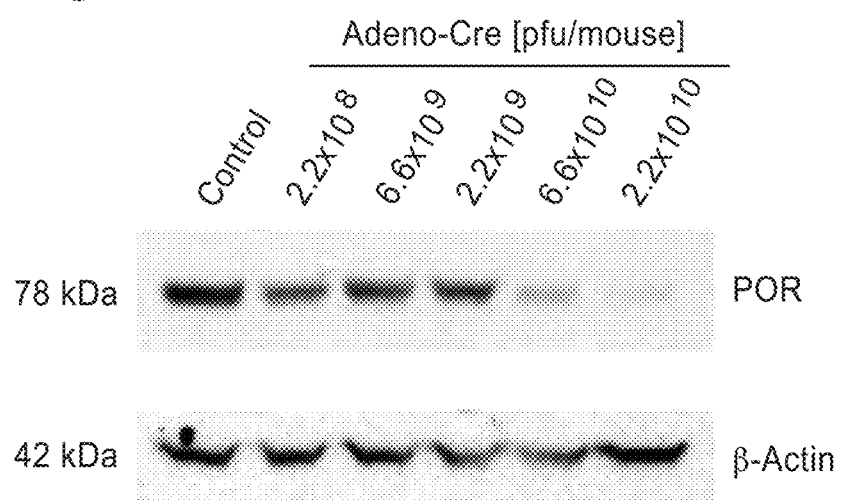
Figure 5:
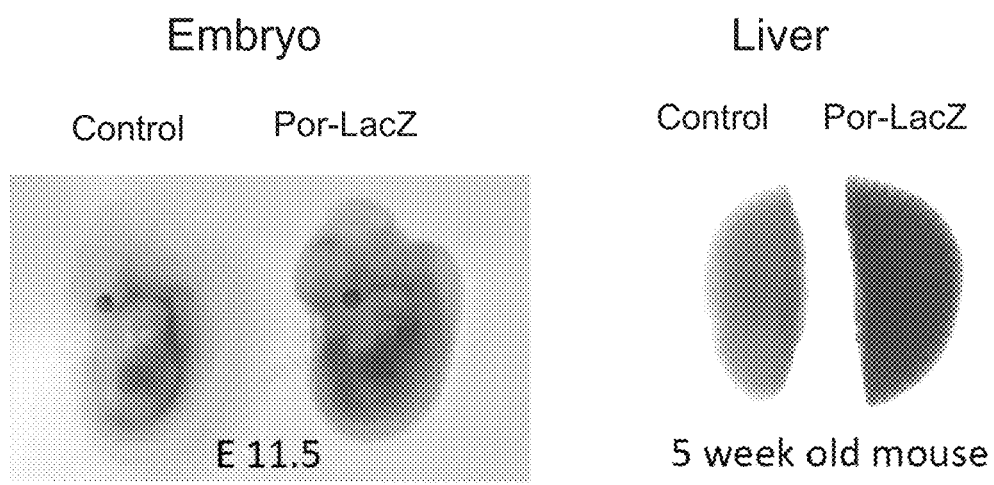
FIG. 5 shows beta galactosidase (lacZ) expression from the POR-lacZ allele. X-gal staining of heterozygous mouse embryo and liver demonstrate expression of the galactosidase from the Por-lacZ allele.
Figure 6B:
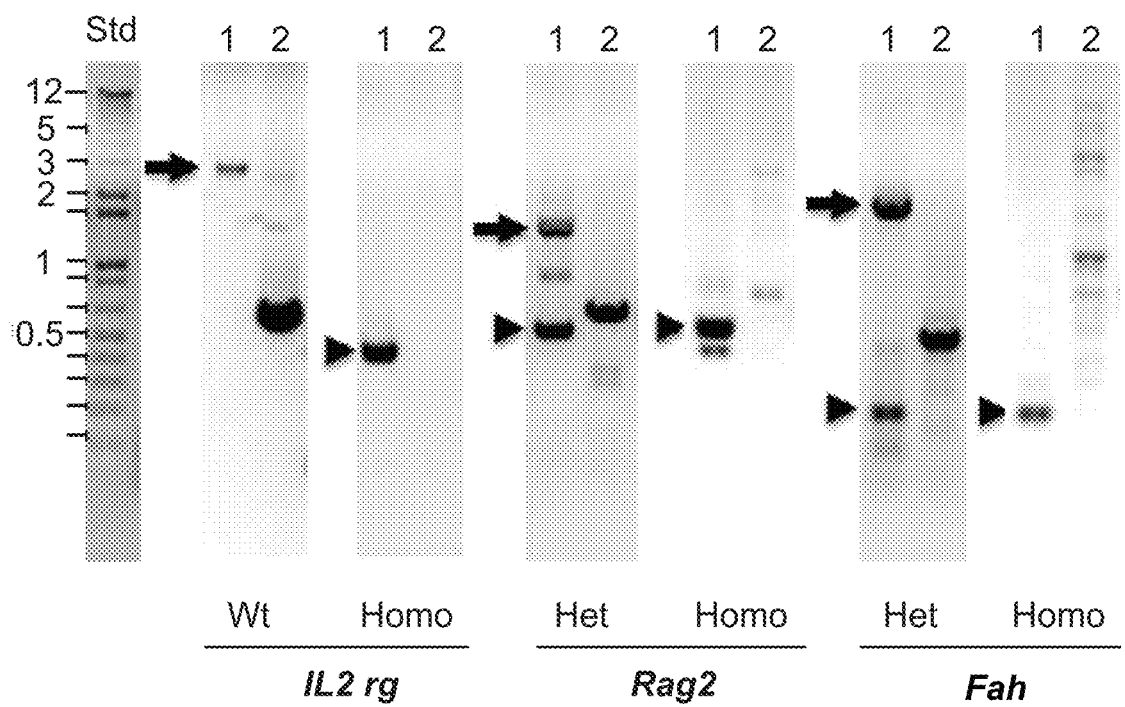
FIG. 6B shows an electrophoresis gel of the PCR products obtained from genotyping. Lane 1: PCR bands using external (Fw and Rv) primers. For Rag2 and Fah heterozygotes, a wild type (arrow) and deleted (arrowhead) allele can be detected. Il2 rg is an X-linked gene and no founder heterozygote females were generated. Homozygotes mice for Il2 rg, Rag2 and Fah show a single deleted allele's band of 460 bp, 530 bp and 200 bp, respectively. Lane 2: PCR bands using one of the external (Fw or Rev) and the internal (Int) primer located between the two gRNA sites. Only heterozygotes have a clear PCR band formed from the wild type allele. Fah and Rag2 homozygotes show multiple unspecific bands while Il2 rg homozygotes do not produce any band.
Figure 7A:
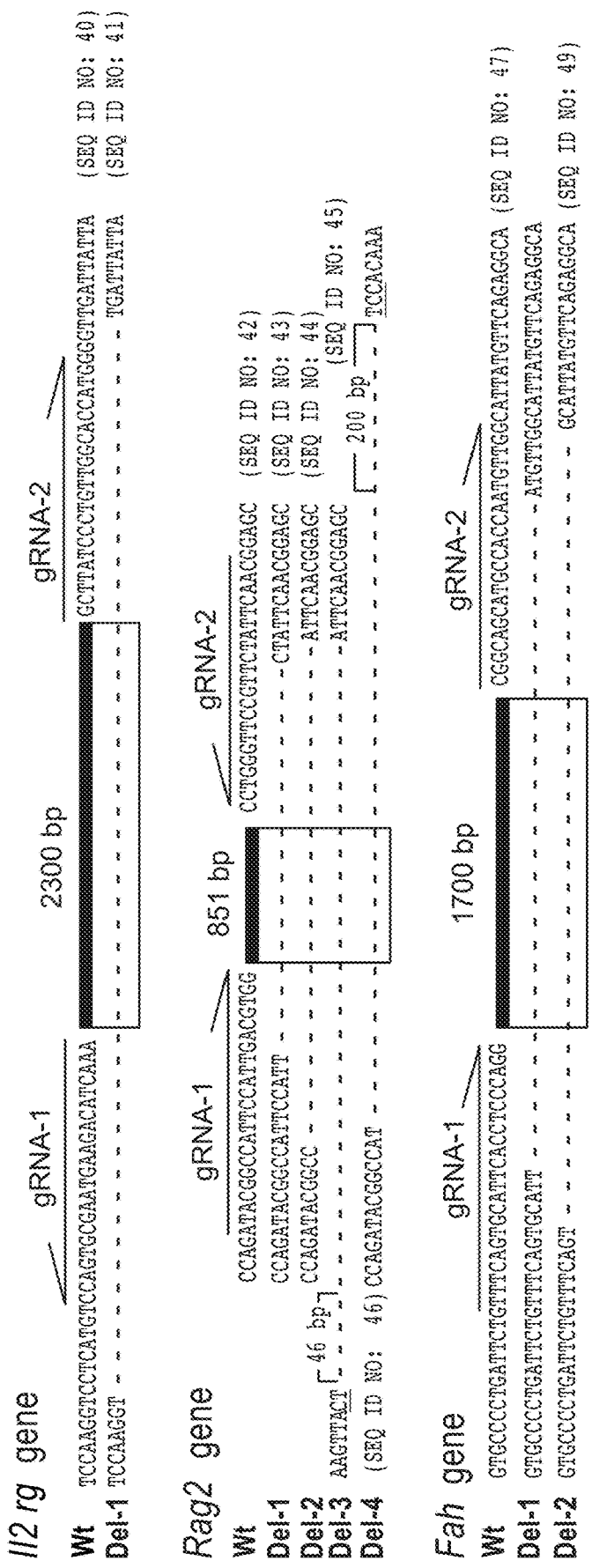

Since the liver is the main organ for drug metabolism, human liver chimeric mice are increasingly used for xenobiotic studies[4-6]. The shortcoming of humanized mice is the remaining murine liver tissue. It has been previously shown that even in mice that can achieve high human chimerism, the average humanization rate is 42%[7]. In order to functionally block the murine cytochrome metabolism, a conditional (floxed exon 3 and 4) knock-out of the NADPH-P450 oxidoreductase (Por) gene was generated by targeting mouse embryonic stem cells[8] (FIG. 4). Injected blastocysts with properly targeted embryonic stem cells generated mice with germline transmission of the Por "knock-out first" allele[9]. Expression from the targeted Por locus using the lacZ expression cassette was confirmed in the embryo and adult liver (FIG. 5). The mice were then bred with a flippase expressing strain[10] to generate a CRE recombinase conditional Por knock-out strain. Homozygous zygotes from this strain were injected with the bacterial type II Clustered Regularly-Interspaced Short Palindromic Repeats/Cas9 (CRISPR-Cas9) system[11-13] targeting simultaneous deletion of critical exons of the Il2-rg and Rag2 and Fah gene (FIG. 6) to generate the PIRF strain (FIG. 1A). Homozygous PIRF mice are immune deficient (T-, B- and NK-cell deficient), but healthy and fertile. Since adenoviral gene therapy vectors efficiently transduce hepatocytes in vivo, the Por gene was deleted using an adenovirus coding the CRE recombinase (Adeno-CRE). Increasing doses ($2.2 \times 10^{8-10}$ per mouse) of the virus were injected intravenously into PIRF mice. QuantitativeRT-PCR of the POR mRNA in liver revealed efficient deletion only at high doses (FIG. 1B). Immunostaining for POR (FIG. 1C) confirmed these findings, while a minimal residual signal could be detected by Western blotting even at the highest dose used (FIG. 1D). POR-deleted PIRF mouse livers accumulated lipids starting two weeks after adenoviral transduction (FIG. 7) similar to a previously reported liver specific Por deletion[14].

Figure 2A:
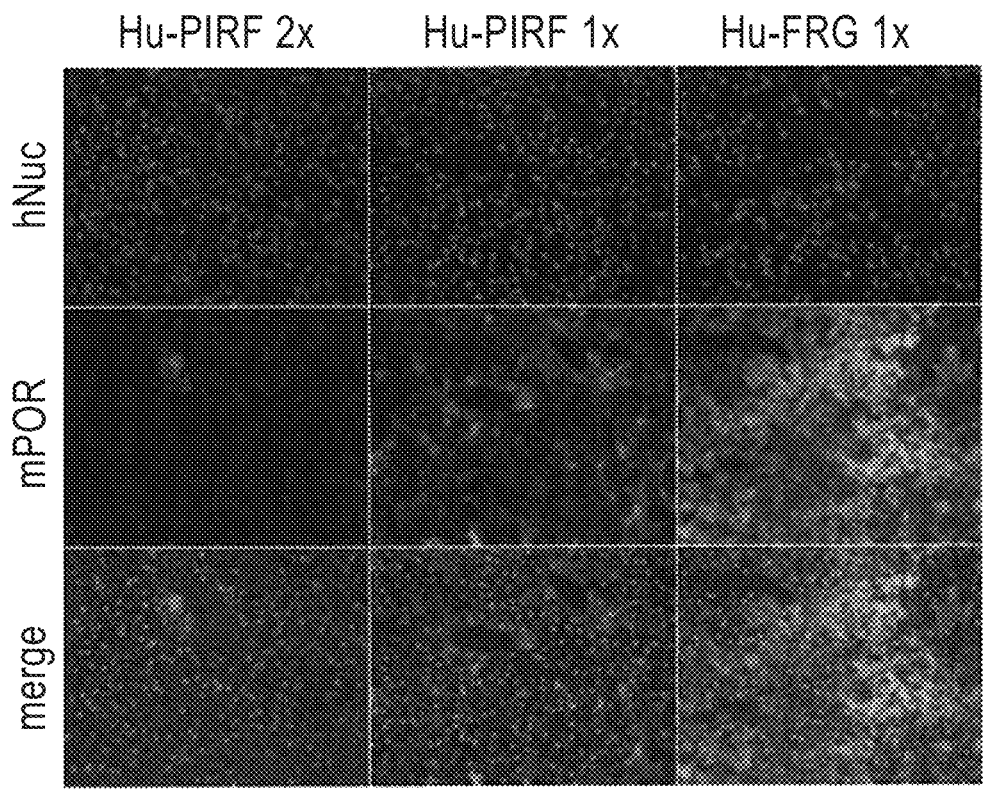
FIG. 2A-E shows the humanization of the PIRF strain and gene expression profiling upon deletion of murine P450 oxidoreductase (Por).
Figure 8:
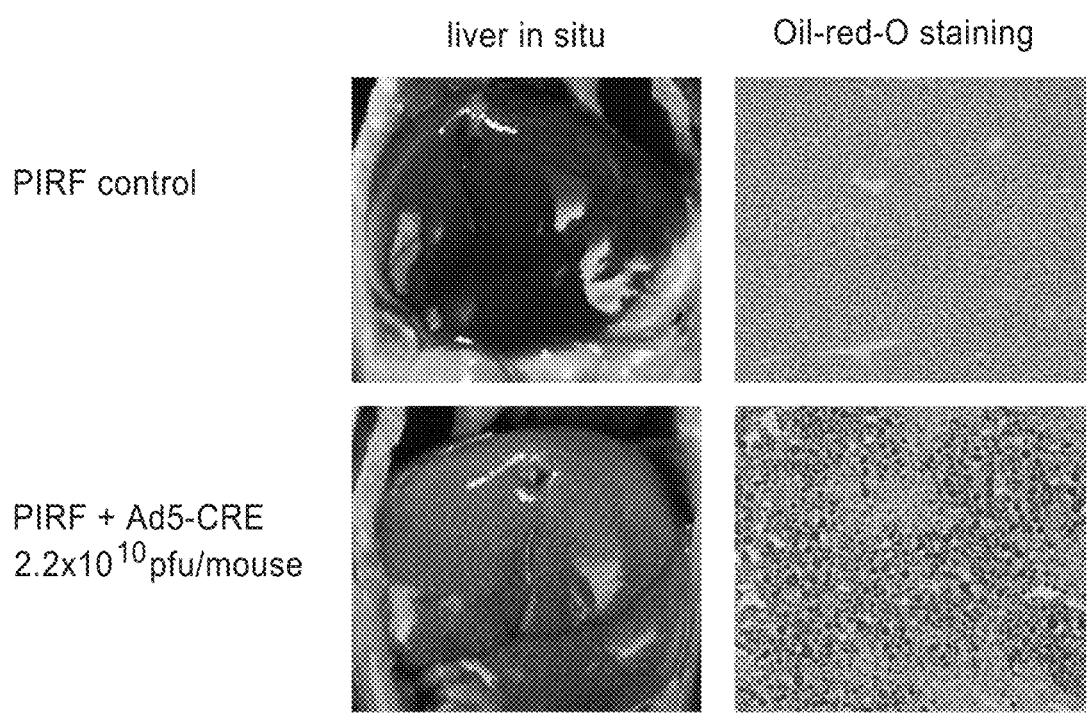
FIG. 8 shows lipid phenotype in the liver of PIRF mice upon deletion of the Por gene using an adenovirus expressing the CRE recombinase. Two weeks after injection of the adenovirus hepatocytes start to accumulated lipids. Oil-red-O stained livers have previously been validated for efficient deletion (upper panel) respectively expression (lower panel) of the Por gene (not shown).

To generate human specific P450 cytochrome metabolism, human liver chimeric mice were generated by transplanting human hepatocytes[7, 15, 16] into Por deleted PIRF mice. However, since a clonal expansion of residual Por expressing murine hepatocytes was observed in Adeno-Cre treated PIRF mice (FIG. 8), some humanized PIRF (Hu-PIRF) mice were injected with an additional dose of Adeno-Cre. Immunostaining revealed that only in double injected humanized PIRF (Hu-PIRF 2×) mice an almost complete deletion of the Por gene could be achieved (FIG. 2A).

Figure 2B:
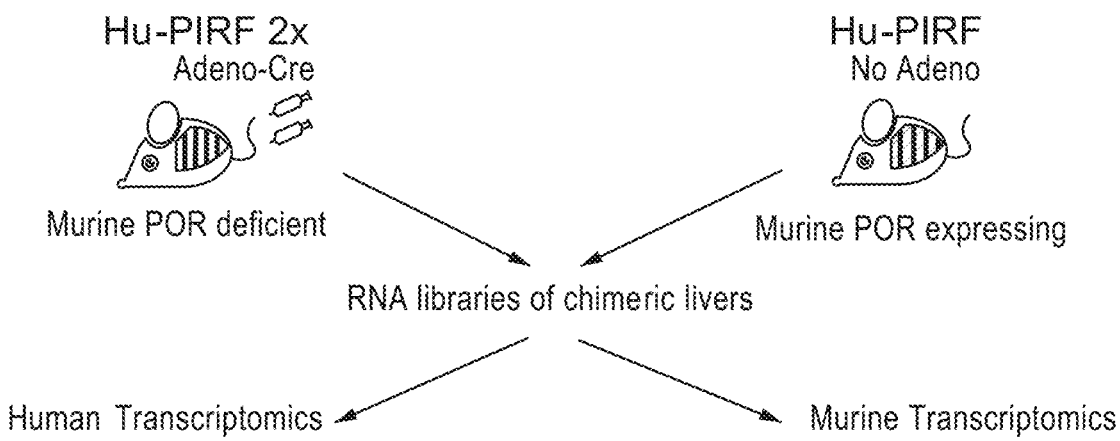
Figure 2C:
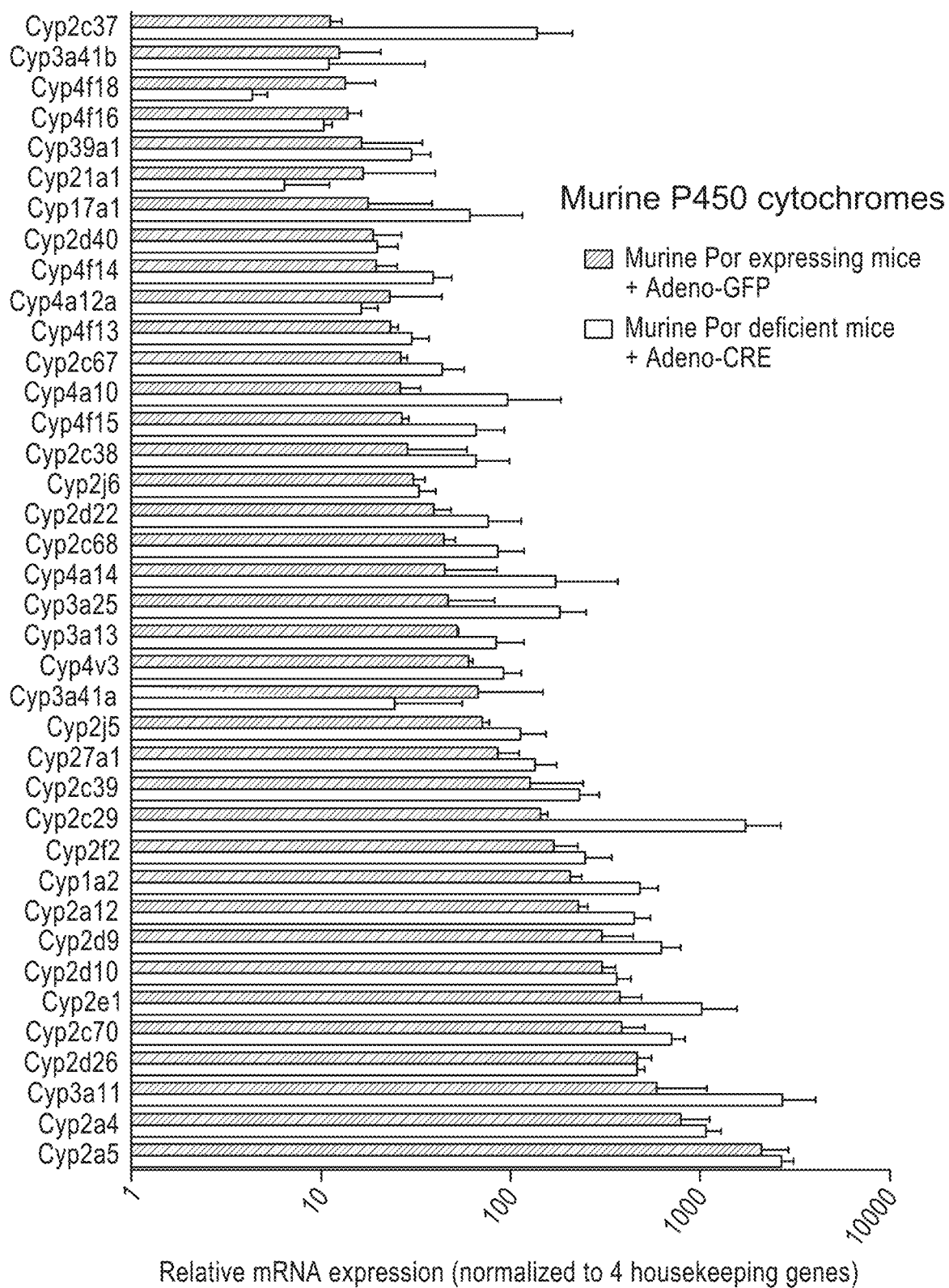

Gene expression profiling was then performed comparing Hu-PIRF mice repopulated with the identical human hepatocytes with or without deletion of the Por (FIG. 2B). Expression of the murine P450 cytochromes was clearly altered for half of the genes: 14 cytochromes were upregulated >1.5-fold and 18 cytochromes downregulated <0.5-fold (FIG. 2c). The expression profiles of these murine cytochromes were comparable to previous work in non-humanized mice (Table 1). Table 1 shows the comparison of murine gene expression profiles of chimeric livers to previously published non-humanized mice. Gene expression of conditional (Alb-Cre) Por KO mice have been quantified by microarray analysis (Weng et al. 2005 J Biol Chem 280, 31686-31698 (2005)). Here, RNA-Seq was used to compare the gene expression (FIG. 2B) in humanized livers transduced with Adeno-Cre and Adeno-GFP. Table 1 lists all previously published cytochromes with values (fold changes) compared to the herein-described data set. Multiple numbers represent multiple sets of microarray probes.

TABLE 1

Comparison of murine gene expression profiles of chimeric livers to previously published non-humanized mice.

| Murine P450 Cytochromes | Present Disclosure Change Fold (Por-deleted/Por non-deleted mice) | Weng et al. 2005 |
|---|---|---|
| Cyp2a4 | 1.4 | 4.5 |
| Cyp2a5 | 1.3 | 4.5 |
| Cyp2b10 | 12.4 | 15.8/16.3/9.1 |
| Cyp2c39 | 1.8 | 1.4 |
| Cyp2c55 | 14.6 | 17.2 |
| Cyp4a10 | 3.7 | 0.3/0.7 |
| Cyp7a1 | 4.6 | 3.1/4.9 |
| Cyp7b1 | 1.6 | 0.2/0.3 |
| Cyp26a1 | 6.7 | 3.5 |
| Cyp51 | 0.6 | 2.2 |

Figure 2D:
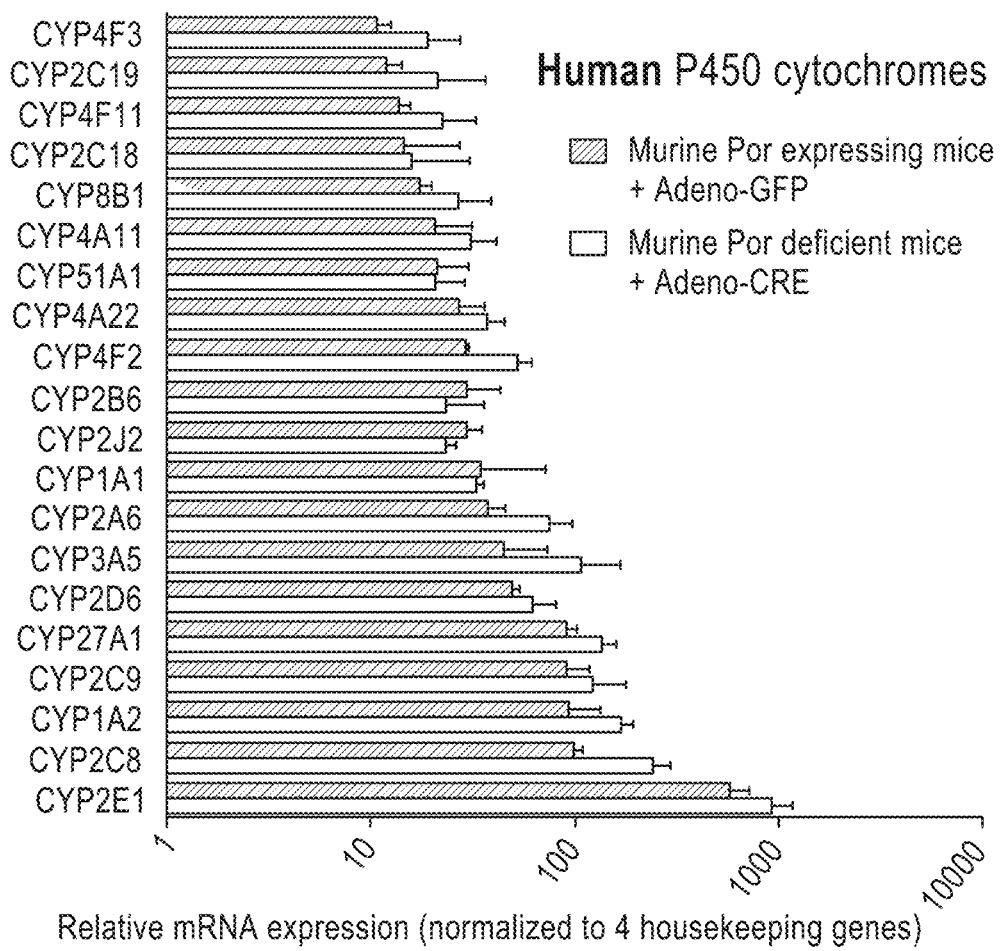

In the same chimeric liver, all human P450 cytochromes were down regulated upon deletion of murine Por with the exception of CYP2C18 (FIG. 2D). Half of the human cytochromes were only slightly (<50%) reduced, and the other half including CYP3A4 and CYP2C19, were more significantly downregulated (>1.5-fold).

Figure 3A:
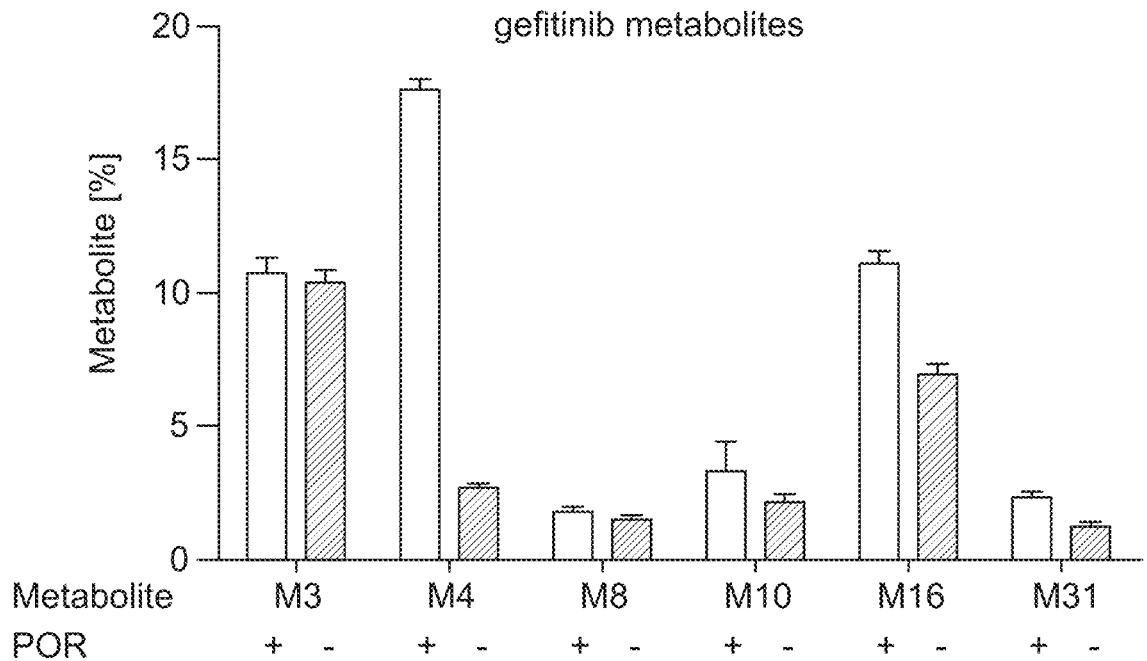
FIG. 3A-E shows xenobiotic metabolism in humanized PIRF mice.
Figure 3B:
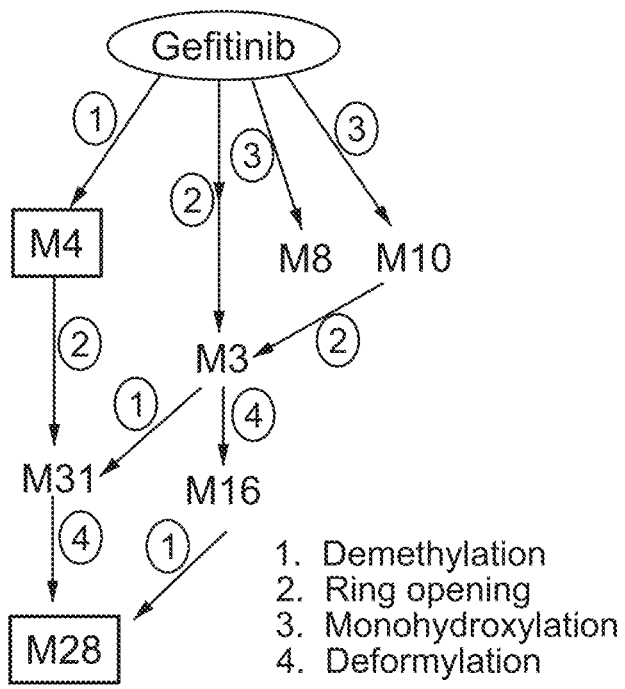
Figure 3C:
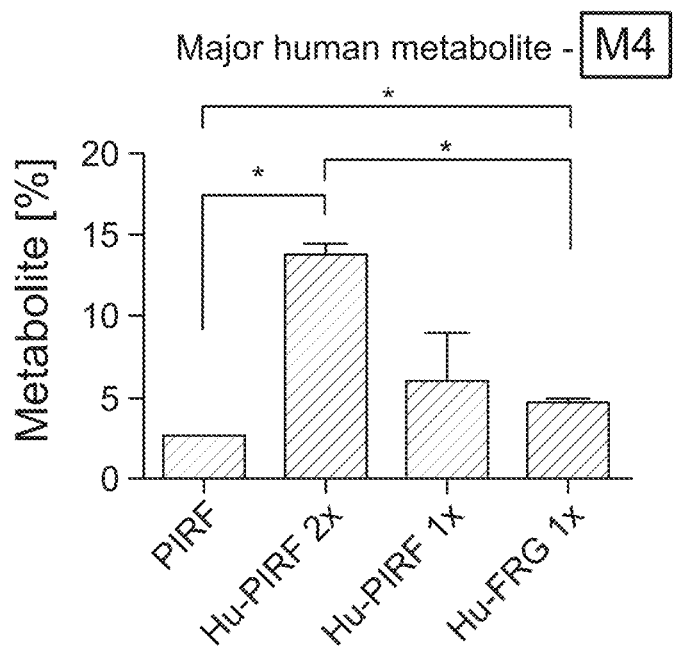
Figure 3D:
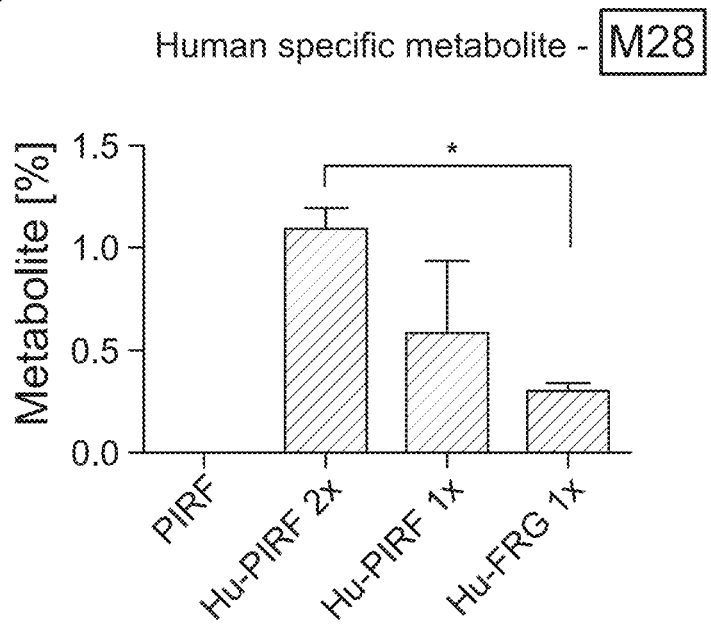

Not all human cytochromes take an important role in xenobiotic metabolism. From the 200 most transcribed drugs in the United States about three quarter are metabolized through P450 cytochromes, of which CYP3A4/5, 2C9, 2C19, 2D6 and 1A2 contribute to ~95% of 17. These human cytochrome clusters were compared from chimeric livers (Hu-PIRF 2×) with the originating, isogenic primary hepatocytes after isolation from the donor liver. Expression levels were similar for most clusters and these important cytochromes robustly expressed in chimeric livers (FIG. 3D).

Figure 3E:
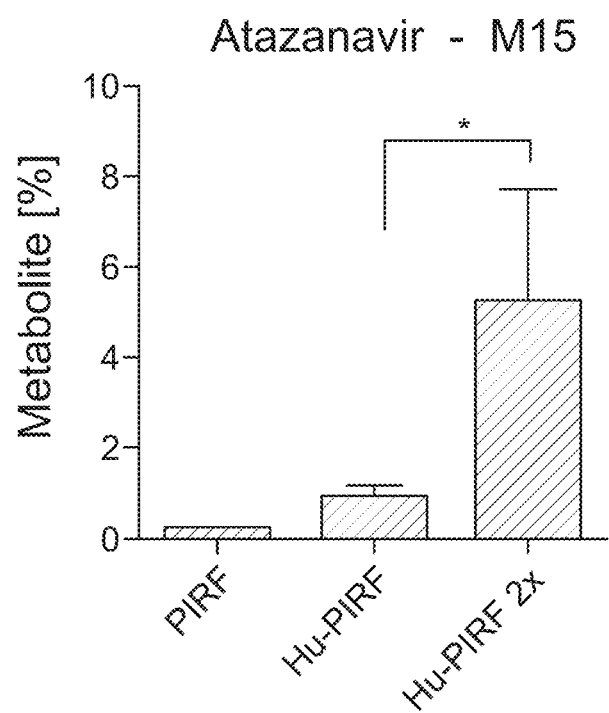
Figure 9:
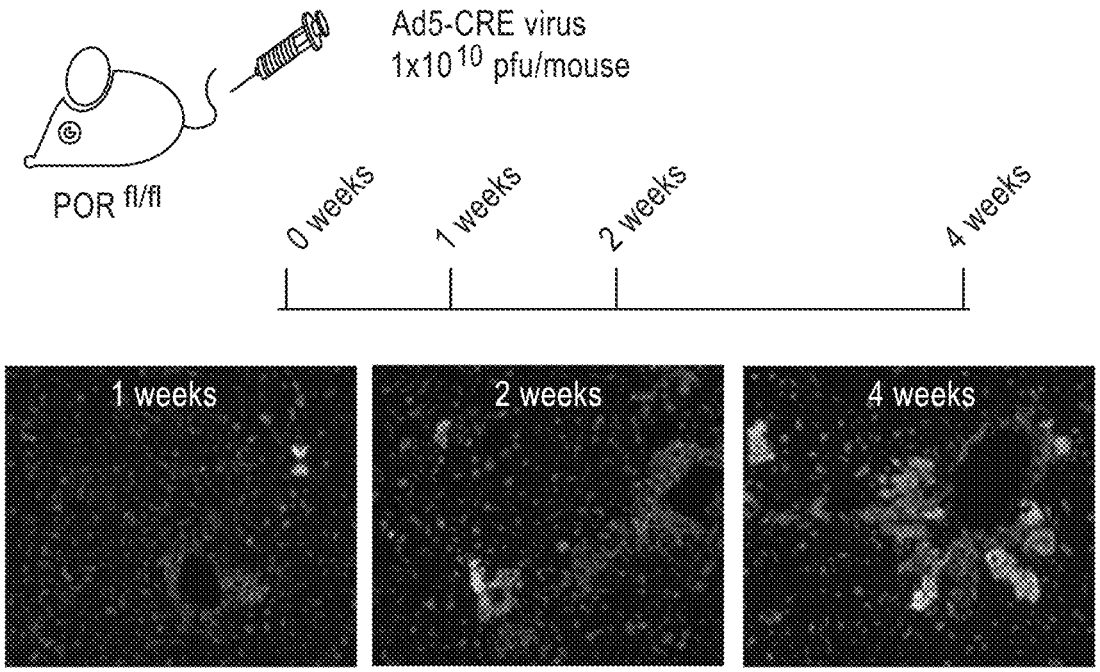
FIG. 9 shows clonal expansion of Por expressing hepatocytes in non-humanized PIRF mice. Mice were injected intravenously with adenovirus expressing CRE recombinase deleting the Por gene (POR$^{fl/fl}$).

To validate utility of Hu-PIRF mice for human drug metabolism, the xenobiotic metabolism of gefetinib[18], an inhibitor of epidermal growth factor receptor used against lung cancer and a variety of other cancers[19], was studied. Gefetinib is primarily metabolized by the P450 cytochrome system including CYP3A4 and 2D6. New gefetinib metabolites were recently identified and demonstrated considerable differences between human and mouse liver microsomes[20]. Gefetinib is excreted in the feces and less than 7% in the urine, irrespectively of dose, route or species[21, 22]. Therefore, the feces of non-humanized PIRF mice was analyzed for gefetinib metabolites during the first 24-hours after intravenous injection of gefetinib. Mass spectrometry revealed a reduction of several gefetinib metabolites upon deletion of the Por gene, implying a Por-dependent P450 cytochrome deficiency for these metabolites (FIG. 3A). The biggest and most relevant reduction was observed for O-desmethyl gefetinib (M4, M523595), which is by far the most abundant metabolite in human feces while rodents produce many different metabolites including M4[21, 22] (FIG. 3B). Therefore, the M4 metabolite was analyzed in murine Por-deleted and Por-expressing humanized and non-humanized control mice (FIG. 9). The highest level of M4 could be detected in murine Por-deficient Hu-PIRF mice, where human hepatocytes preferentially metabolize gefetinib to M4 and remaining murine hepatocytes are inhibited in their drug metabolism (FIG. 3C). Although murine hepatocytes preferentially produce other metabolites than M4, human specific metabolites were measured. M28 was the most abundant human metabolite, which could not be detected in the non-humanized control mice. Mass spectrometry again showed the highest level of this human specific metabolite in murine Por-deficient Hu-PIRF mice confirming a more human like metabolism in these mice (FIG. 3D). Human xenobiotic metabolism was also determined with another drug, however, this time using liver homogenates of PIRF mice. Using human and mouse microsomes, it was previously demonstrated that atazanavir metabolite M15 is a predominately human metabolite (See, Li, F et al., "CYP3A-mediated generation of aldehyde and hydrazine in atazanavir metabolism." Drug Metab Dispos 39, 394-401. Mice were intravenously injected with the retroviral therapeutic and livers were harvested 30 min after injection. Results showed that M15 was 5.4-times elevated in POR-deleted humanized PIRF mice compared to non-deleted mice (FIG. 3E) again confirming optimized human drug metabolism in this novel mouse model.

Identification of human metabolites using current experimental animal models is a major challenge. Nevertheless, identification of reactive metabolites is crucial since they drive human drug toxicity[23, 24]. The novel humanized mouse model of the instant disclosure inhibits murine drug metabolism without impeding on the human metabolism. Murine Por-deficient humanization can be used in combination with other repopulation models like the transgenic uPA mouse and can identify more readily human specific metabolites for a greater benefit of drug safety.

Identification of mostly human or human specific metabolites is possible with the present disclosure irrespectively of toxicity. Toxicity may be present; however this is not always the case. For instance, as shown here, gefetinib did not cause any elevation of liver enzymes, yet mainly human metabolites were identified.

The present disclosure provides a method for preparing a chimeric mouse substantially lacking murine hepatocytes and instead comprising human hepatocytes, comprising steps of: (a) providing a mouse comprising a knockout mutation in each of the Il2-rg, Rag2, and Fah genes and a floxed allele of the NADPH-P450 oxidoreductase (Por) gene with a first dose of a virus that encodes Cre recombinase, thereby producing a conditional knockout of the Por gene or the knockout of the por gene using somatic genome engineering (CRIPSR/Cas9) and gene therapy vectors in Il2-rg, Rag2, and Fah deficient mice; (b) transplanting human hepatocytes into the mouse; and (c) providing the mouse with a second dose of the virus that encodes Cre recombinase. Steps (a) and (b) can occur sequentially or simultaneously.

Figure 11A:
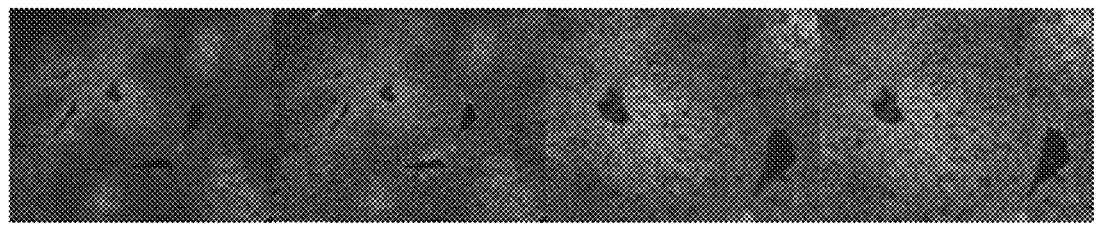
FIGS. 11A and 11B show that the conditional KO of POR can also be generated using a transgenic animal, which carries an expression cassette (albumin promoter) of the CRE recombinase.
Figure 11B:
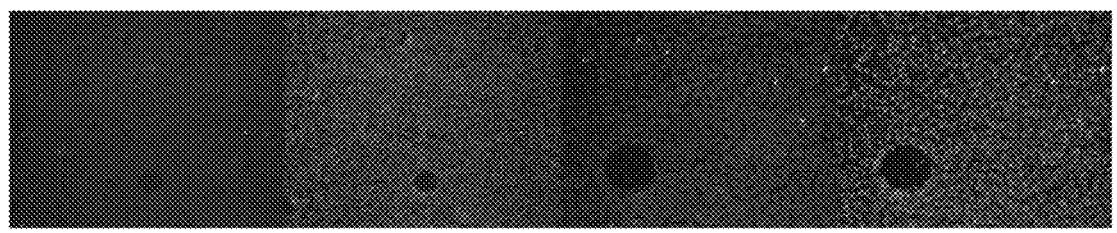

The conditional knock-out POR alleles can also be generated by delivering CRE recombinase in any way known in the art. Non-limiting examples of Cre recombinase delivery include viral or non-viral gene therapy vectors. In one embodiment, the gene therapy vector is an adenovirus. Also considered are genetic delivery of Cre recombination, e.g., under a cell-, tissue-, or developmental-specific promoter or under an inducible promoter. Indeed, Cre recombinase can be activated in the murine liver in a transgenic animal with Cre expressed under the albumin or other liver specific promoter (FIG. 11).

The present disclosure also provides a chimeric mouse, offspring thereof, or a portion thereof, which has a chimeric liver comprising human hepatocytes. Preferably, the chimeric mouse, offspring thereof or a portion thereof is prepared by the methods of the present disclosure. The chimeric mouse can be immunodeficient.

In the present disclosure, examples of the chimeric mouse include portions of the mouse. The term "a portion(s) of the mouse" refers to, mouse-derived tissues, body fluids, cells, and disrupted products thereof or extracts therefrom, for example (the examples thereof are not particularly limited to them). Examples of such tissues include, but are not particularly limited to, heart, lungs, kidney, liver, gallbladder, pancreas, spleen, intestine, muscle, blood vessel, brain, testis, ovary, uterus, placenta, marrow, thyroid gland, thymus gland, and mammary gland. Examples of body fluids include, but are not particularly limited to, blood, lymph fluids, and urine. The term "cells" refers to cells contained in the above tissues or body fluids, and examples thereof include cultured cells, sperm cells, ova, and fertilized eggs obtained by isolation or culture thereof. Examples of cultured cells include both primary cultured cells and cells of an established cell line. Examples of the portions of the mouse also include tissues, body fluids, and cells at the developmental stage (embryonic stage), as well as the disrupted products or extracts thereof. In addition, an established cell line from the mouse of the present disclosure can be established using a known method (Primary Culture Methods for Embryonic Cells (Shin Seikagaku Jikken Koza (New Biochemical Experimental Lecture Series), Vol. 18, pages 125-129, TOKYO KAGAKU DOZIN CO., LTD., and Manuals for. Mouse Embryo Manipulation, pages 262-264, Kindai Shuppan)).

The mouse of the present disclosure can be an immunodeficient mouse. The immunodeficient mouse of the present disclosure can be used as a host mouse for transplantation of human hepatocytes. Examples of the "immunodeficient mouse" may be any mouse that does not exhibit rejection against hepatocytes (in particular, human hepatocytes) from a different animal origin, and include, but are not limited to, SCID (severe combined immunodeficiency) mice exhibiting deficiency in T- and B-cell lines, mice (NUDE mice) that have lost T cell functions because of genetic deletion of the thymus gland, and mice (RAG2 knockout mice) produced by knocking out the RAG2 gene by a known gene targeting method (Science, 244: 1288-1292, 1989).

Moreover, the present disclosure provides a chimeric mouse having human hepatocytes. The chimeric mouse of the present disclosure can be immunologically deficient. The chimeric mouse of the present disclosure can be prepared by transplanting human hepatocytes into an immunodeficient mouse of the present disclosure.

As human hepatocytes to be used for transplantation, human hepatocytes isolated from normal human liver tissue by a conventional method such as a collagenase perfusion method can be used. The thus separated hepatocytes can also be used by thawing after cryopreservation. Alternatively, the chimeric mouse hepatocytes, which are defined as the human hepatocytes separated by a technique such as a collagenase perfusion method from a chimeric mouse liver, in which mouse hepatocytes have been replaced by human hepatocytes, can be used in a fresh state, and the cryopreserved chimeric mouse hepatocytes are also available after thawing.

Such human hepatocytes can be transplanted into the liver via the spleen of a mouse of the present disclosure. Such human hepatocytes can also be directly transplanted via the portal vein. The number of human hepatocytes to be transplanted may range from about 1 to 2,000,000 cells and preferably range from about 200,000 to 1,000,000 cells. The gender of the mouse of the present disclosure is not particularly limited. Also, the age on days of the mouse of the present disclosure upon transplantation is not particularly limited. When human hepatocytes are transplanted into a young mouse (early weeks of age), human hepatocytes can more actively proliferate as the mouse grows. Hence, about 0- to 40-day-old mice after birth, and particularly about 8- to 40-day-old mice after birth are preferably used.

The transplanted human hepatocytes account for any percentage of human chimerism greater than about 1%, for example at least 5%, at least 10%, at least 20%, at least 30%, at least 40%, at least 50%, at least 60%, at least 70%, at least 80%, at least 90%, at least 95% or at least 99% of all hepatocytes in the chimeric liver of the chimeric non-human animal.

The present disclosure further provides a method for screening for a substance that affects human liver functions, with the use of the chimeric mouse of the present disclosure. An example of the method is an evaluation method comprising the following steps of: (a) administering a test substance to the chimeric mouse of the present disclosure; (b) measuring one or more values in the chimeric mouse to which the test substance is administered in (a); and (c) selecting a test substance that causes an increase or an decrease in one or more values measured in (b), compared with the one or more values of the chimeric mouse to which no test substance is administered.

Preferably, the one or more values are selected from the group consisting of the human albumin concentration, the body weight curve, the liver-weight-to-body-weight ratio, the total albumin level, the total protein level, the ALT level, the AST level, and the total bilirubin level, histological assessment for toxicity in the human and non-human organs.

Examples of the "test substance" in the method of the present disclosure are not particularly limited and include natural compounds, organic compounds, inorganic compounds, proteins, antibodies, peptides, and single compounds such as an amino acid, and nucleic acids, as well as compound libraries, expression products from gene libraries, cell extracts, cell culture supernatants, products of fermenting microorganisms, extracts from marine creatures, plant extracts, extracts from prokaryotic cells, extracts from eukaryotic single cells, and extracts from animal cells. These products may be purified products or crude products such as plant, animal, or microbial extracts. Also, a method for producing a test substance is not particularly limited. A test substance to be used herein may be a substance isolated from a natural product, synthesized chemically or biochemically, or prepared by genetic engineering techniques.

The above test substance can be adequately labeled and then used as necessary. Examples of labels include radiolabels and fluorescent labels. Examples of the test substance include, in addition to the above test samples, mixtures of a plurality of types of these test samples.

Examples of test samples include and are not limited to feces, urine, blood (and any blood product, e.g., whole blood, serum, and plasma), and tissue, e.g., liver tissue. Liver tissue may be derived from a sample of a liver (e.g., a biopsy or explant) or may be derived from a whole, intact liver, e.g., that has been harvested after a mouse has been sacrificed.

Examples of a method for administering a test substance to mice are not particularly limited. Such an administration method can be adequately selected from among oral administration or parenteral administration such as subcutaneous, intravenous, local, transdermal, and enteral (intrarectal) administration, depending on the type of a test substance to be administered.

The present disclosure further provides a method for evaluating hepatotoxicity of a test substance against human hepatocytes, with the use of the chimeric mouse of the present disclosure. An example of this method is an evaluation method comprising the following steps of: (a) administering a test substance to the chimeric mouse of the present disclosure; (b) measuring one or more values in the chimeric mouse to which the test substance is administered in (a); and (c) evaluating the effect of the test substance on human hepatocytes using one or more indicators measured in (b), compared with the one or more indicators of the chimeric mouse to which no test substance is administered.

Preferably, the one or more values are selected from the group consisting of the human albumin concentration, the body weight curve, the liver-weight-to-body-weight ratio, the total albumin level, the total protein level, the ALT level, the AST level, and the total bilirubin level. Preferably, the one or more indicators are selected from the group consisting of an increase or a decrease in any one or more of the human albumin concentration, the body weight curve, the liver-weight-to-body-weight ratio, the total albumin level, the total protein level, the ALT level, the AST level, and the total bilirubin level.

A human nucleic sequence encoding an exemplary Por gene of the disclosure consist or comprises, Genbank Accession number: NM_000941.2:

(SEQ ID NO: 24)
```
   1 gaaggcggtg gtagcgcctc agtggtgtgg gcctgagccc tgcccaggtg cccgcagaga
  61 gcagccgggc tgccagcgtt tcatgatcaa catgggagac tcccacgtgg acaccagctc
 121 caccgtgtcc gaggcggtgg ccgaagaagt atctcttttc agcatgacgg acatgattct
 181 gttttcgctc atcgtgggtc tcctaaccta ctggttcctc ttcagaaaga aaaagaaga
 241 agtccccgag ttcaccaaaa ttcagacatt gacctcctct gtcagagaga gcagctttgt
 301 ggaaaagatg aagaaaacgg ggaggaacat catcgtgttc tacggctccc agacggggac
 361 tgcagaggag tttgccaacc gcctgtccaa ggacgcccac cgctacggga tgcgaggcat
 421 gtcagcggac cctgaggagt atgacctggc cgacctgagc agcctgccag agatcgacaa
 481 cgccctggtg gttttctgca tggccaccta cggtgaggga gaccccaccg acaatgccca
 541 ggacttctac gactggctgc aggagacaga cgtggatctc tctggggtca agttcgcggt
 601 gtttggtctt gggaacaaga cctacgagca cttcaatgcc atgggcaagt acgtggacaa
 661 gcggctggag cagctcggcg cccagcgcat ctttgagctg gggttgggcg acgacgatgg
 721 gaacttggag gaggacttca tcacctggcg agagcagttc tggccggccg tgtgtgaaca
 781 ctttggggtg gaagccactg gcgaggagtc cagcattcgc cagtacgagc ttgtggtcca
 841 caccgacata gatgcggcca aggtgtacat ggggagatg ggccggctga agagctacga
 901 gaaccagaag cccccctttg atgccaagaa tccgttcctg gctgcagtca ccaccaaccg
 961 gaagctgaac cagggaaccg agcgccacct catgcacctg gaattggaca tctcggactc
1021 caaaatcagg tatgaatctg gggaccacgt ggctgtgtac ccagccaacg actctgctct
1081 cgtcaaccag ctgggcaaaa tcctgggtgc cgacctggac gtcgtcatgt ccctgaacaa
1141 cctggatgag gagtccaaca agaagcaccc attcccgtgc cctacgtcct accgcacggc
1201 cctcacctac tacctggaca tcaccaaccc gccgcgtacc aacgtgctgt acgagctggc
1261 gcagtacgcc tcggagccct cggagcagga gctgctgcgc aagatggcct cctcctccgg
1321 cgagggcaag gagctgtacc tgagctgggt ggtggaggcc cggaggcaca tcctggcccat
```

-continued

```
1381 cctgcaggac tgcccgtccc tgcggccccc catcgaccac ctgtgtgagc tgctgccgcg 1441 cctgcaggcc cgctactact ccatcgcctc atcctccaag gtccacccca actctgtgca 1501 catctgtgcg gtggttgtgg agtacgagac caaggctggc cgcatcaaca agggcgtggc 1561 caccaactgg ctgcgggcca aggagcctgc cggggagaac ggcggccgtg cgctggtgcc 1621 catgttcgtg cgcaagtccc agttccgcct gcccttcaag gccaccacgc ctgtcatcat 1681 ggtgggcccc ggcaccgggg tggcacccct cataggcttc atccaggagc gggcctggct 1741 gcgacagcag ggcaaggagg tgggggagac gctgctgtac tacggctgcc gccgctcgga 1801 tgaggactac ctgtaccggg aggagctggc gcagttccac agggacggtg cgctcaccca 1861 gctcaacgtg gccttctccc gggagcagtc ccacaaggtc tacgtccagc acctgctaaa 1921 gcaagaccga gagcacctgt ggaagttgat cgaaggcggt gcccacatct acgtctgtgg 1981 ggatgcacgg aacatggcca gggatgtgca gaacaccttc tacgacatcg tggctgagct 2041 cggggccatg gagcacgcgc aggcggtgga ctacatcaag aaactgatga ccaagggccg 2101 ctactccctg gacgtgtgga gctaggggcc tgcctgcccc acccacccca cagactccgg 2161 cctgtaatca gctctcctgg ctccctcccg tagtctcctg ggtgtgtttg gcttggcctt 2221 ggcatgggcg caggcccagt gacaaagact cctctgggcc tggggtgcat cctcctcagc 2281 ccccaggcca ggtgaggtcc accggcccct ggcagcacag cccagggcct gcatgggggc 2341 accgggctcc atgcctctgg aggcctctgg ccctcggtgg ctgcacagaa gggctctttc 2401 tctctgctga gctgggccca gcccctccac gtgatttcca gtgagtgtaa ataatttttaa 2461 ataacctctg gcccttggaa taaagttctg ttttctgtaa aaaaaaaa
```

The corresponding human amino acid sequence encoding an exemplary Por gene of the disclosure consist or comprises, Genbank Accession number: NP_000932.3:

(SEQ ID NO: 25)
```
  1 minmgdshvd tsstvseava eevslfsmtd milfslivgl ltywflfrkk keevpeftki
 61 qtltssvres sfvekmkktg rniivfygsq tgtaeefanr lskdahrygm rgmsadpeey
121 dladlsslpe idnalvvfcm atygegdptd naqdfydwlq etdvdlsgvk favfglgnkt
181 yehfnamgky vdkrleqlga qrifelglgd ddgnleedfi twreqfwpav cehfgveatg
241 eessirqyel vvhtdidaak vymgemgrlk syenqkppfd aknpflaavt tnrklnqgte
301 rhlmhleldi sdskiryesg dhvavypand salvnqlgki lgadldvvms lnnldeesnk
361 khpfpcptsy rtaltyyldi tnpprtnvly elaqyaseps eqellrkmas ssgegkelyl
421 swvvearrhi lailqdcpsl rppidhlcel lprlqaryys iassskvhpn svhicavvve
481 yetkagrink gvatnwlrak epagenggra lvpmfvrksq frlpfkattp vimvgpgtgv
541 apfigfiqer awlrqqgkev getllyygcr rsdedylyre elaqfhrdga ltqlnvafsr
601 eqshkvyvqh llkqdrehlw kliegga hiy vcgdarnmar dvqntfydiv aelgamehaq
661 avdyikklmt kgrysldvws
```

A murine nucleic sequence encoding an exemplary Por gene of the disclosure consist or comprises, Genbank Accession number: NM_008898.2:

(SEQ ID NO: 26)
```
  1 gggccgtggt agcgcctcag tggtgcgggc ttgcgtccgg ccccagtgcc tcagagacct
 61 acaggaccgc gcgcggtgtg tgatctggtc ggtaccgagg agcgcaggtt gtgtcaccaa
```

-continued

```
 121 catgggggac tctcacgaag acaccagtgc cacagtgcct gaggcagtgg ctgaagaagt
 181 gtctctattc agcacaacgg acattgttct gttttctctc atcgtggggg tcctgaccta
 241 ctggttcatc tttaaaaaga agaaagaaga gataccggag ttcagcaaga tccagacaac
 301 ggccccacct gtcaaagaga gcagcttcgt ggaaaagatg aagaaaacgg aaggaacat
 361 tattgtattc tatggctccc agacgggaac cgcggaggag tttgccaacc ggctgtccaa
 421 ggatgcccac cgctatggga tgcggggcat gtctgcagac cctgaagagt atgacttggc
 481 cgacctgagc agcctgcctg agatcgacaa gtccctggta gtcttctgca tggccacata
 541 cggagaaggc gaccccaccg acaacgcgca ggacttctat gattggctgc aggagactga
 601 cgtggacctc acgggtgtca agtttgctgt gtttggtctc gggaacaaga cctatgagca
 661 cttcaacgcc atgggcaagt atgtggacca gcggctggag cagcttggcg cccagcgaat
 721 ctttgagttg ggccttggtg atgacgacgg gaacttggaa gaggatttca tcacatggag
 781 ggagcagttc tggccagctg tgtgcgagtt cttcggggtg gaagccactg gggaggagtc
 841 gagcatccgc cagtacgagc tcgtggtcca cgaagacatg gacacagcca aggtgtacac
 901 gggtgagatg ggccgtctga agagctacga gaaccagaaa ccccccttcg atgccaagaa
 961 tccattcctg gctgctgtca ccacgaaccg gaagctgaac caaggcactg agaggcatct
1021 aatgcacctg gaattggaca tctcagactc caagatcagg tatgaatctg gagatcacgt
1081 ggctgtgtac ccagccaacg actccaccct ggtcaaccag attggggaga tcctgggggc
1141 tgacctggat gtcatcatgt ctctaaacaa tctcgatgag gagtcgaata agaagcatcc
1201 gttccctgc cccaccacct accgcacggc cctcacctac tacctggaca tcactaaccc
1261 gccacgaacc aacgtgctct acgagctggc ccagtacgcc tcagagccct cggagcagga
1321 acacctgcac aagatggcgt cctcctccgg cgagggcaag gagctgtacc tgagctgggt
1381 ggtggaggcc cggaggcaca tcctagccat tctccaagac tacccgtccc tgcggccacc
1441 catcgaccac ctgtgcgagc tcctcccgag gctgcaggcc cgctactatt ccattgcctc
1501 gtcgtctaag gtccacccca actccgtgca catctgcgcc gtggctgtgg agtatgaagc
1561 gaagtctgga cgagtgaaca agggggtggc caccagctgg cttcggacca aggaaccagc
1621 aggagagaat ggccgccggg ccctggtccc catgttcgtc cgcaagtccc agttccgctt
1681 gcctttcaag cccaccacac ctgttatcat ggtgggcccc ggcactgggg ttgccccttt
1741 catgggcttc atccaggagc gggcttggct tcgagagcaa ggcaaggagg tcggagagac
1801 gctgctctac tacggctgcc ggcgctcgga tgaggactat ctgtaccgcg aggagctggc
1861 gcgcttccac aaggacggcg ccctcacgca gcttaatgtg gccttttccc gtgagcaggc
1921 ccacaaggtc tatgttcagc acctgctcaa gagggacaaa gagcacctgt ggaagctgat
1981 ccacgaaggt ggtgcccaca tctatgtctg cggggatgct cgaaatatgg ccaaagatgt
2041 gcagaacaca ttctatgaca tcgtggccga gtttgggccc atggagcaca cccaggctgt
2101 ggactatgtt aagaagctca tgaccaaggg ccgctactcg ctggatgtat ggagctagga
2161 gctgccgccc ccacccctc gctccctgta atcacgtcct taacttcctt ctgccgacct
2221 ccacctctgt tggttcctgc cctgcctgga cacagggagg cccaggact gactcctggc
2281 ctgagtgatg ccctcctggg cccttaggca gagcctggtc cattgtacca ggcagcctag
2341 cccagcccag ggcacatggc aagagggact ggacccacct ttgggtgatg ggtgccttag
2401 gtccccagca gctgtacaga aggggctctt ctctccacag agctggggtg cagccccaac
2461 atgtgatttt gaatgagtgt aaataatttt aaataacctg gcccttggaa taaagttgtt
2521 ttctgta
```

The corresponding murine amino acid sequence encoding an exemplary Por gene of the disclosure consists or comprises, Genbank Accession number: NP_032924.1:

(SEQ ID NO: 27)

```
  1 mgdshedtsa tvpeavaeev slfsttdivl fslivgvlty wfifkkkkee ipefskiqtt
 61 appvkessfv ekmkktgrni ivfygsqtgt aeefanrlsk dahrygmrgm sadpeeydla
121 dlsslpeidk slvvfcmaty gegdptdnaq dfydwlqetd vdltgvkfav fglgnktyeh
181 fnamgkyvdq rleqlgaqri felglgdddg nleedfitwr eqfwpavcef fgveatgees
241 sirqyelvvh edmdtakvyt gemgrlksye nqkppfdakn pflaavttnr klnqgterhl
301 mhleldisds kiryesgdhv avypandstl vnqigeilga dldvimslnn ldeesnkkhp
361 fpcpttyrta ltyyylditnp prtnvlyela qyasepseqe hlhkmasssg egkelylswv
421 vearrhilai lqdypslrpp idhlcellpr lqaryysias sskvhpnsvh icavaveyea
481 ksgrvnkgva tswlrtkepa gengrralvp mfvrksqfrl pfkpttpvim vgpgtgvapf
541 mgfiqerawl reqgkevget llyygcrrsd edylyreela rfhkdgaltq lnvafsreqa
601 hkvyvqhllk rdkehlwkli heggahiyvc gdarnmakdv qntfydivae fgpmehtqav
661 dyvkklmtkg rysldvws
```

25

A human nucleic sequence encoding an exemplary Il2-rg gene of the disclosure consist or comprises, Genbank Accession number: NM_000206.2:

(SEQ ID NO: 28)

```
   1 agaggaaacg tgtgggtggg gaggggtagt gggtgaggga cccaggttcc tgacacagac
  61 agactacacc cagggaatga agagcaagcg ccatgttgaa gccatcatta ccattcacat
 121 ccctcttatt cctgcagctg cccctgctgg gagtgggct gaacacgaca attctgacgc
 181 ccaatgggaa tgaagacacc acagctgatt tcttcctgac cactatgccc actgactccc
 241 tcagtgtttc cactctgccc ctcccagagg ttcagtgttt tgtgttcaat gtcgagtaca
 301 tgaattgcac ttggaacagc agctctgagc ccagcctac aacctcact ctgcattatt
 361 ggtacaagaa ctcggataat gataaagtcc agaagtgcag ccactatcta ttctctgaag
 421 aaatcacttc tggctgtcag ttgcaaaaaa aggagatcca cctctaccaa acatttgttg
 481 ttcagctcca ggacccacgg gaacccagga gacaggccac acagatgcta aaactgcaga
 541 atctggtgat cccctgggct ccagagaacc taacacttca caaactgagt gaatcccagc
 601 tagaactgaa ctggaacaac agattcttga accactgttt ggagcacttg gtgcagtacc
 661 ggactgactg ggaccacagc tggactgaac aatcagtgga ttatagacat aagttctcct
 721 tgcctagtgt ggatgggcag aaacgctaca cgtttcgtgt tcggagccgc tttaacccac
 781 tctgtggaag tgctcagcat tggagtgaat ggagccaccc aatccactgg gggagcaata
 841 cttcaaaaga gaatcctttc ctgtttgcat ggaagccgt ggttatctct gttggctcca
 901 tgggattgat tatcagcctt ctctgtgtgt atttctggct ggaacggacg atgccccgaa
 961 ttcccacct gaagaaccta gaggatcttg ttactgaata ccacgggaac ttttcggcct
1021 ggagtggtgt gtctaaggga ctggctgaga tctgcagcc agactacagt gaacgactct
1081 gcctcgtcag tgagattccc ccaaaaggag gggcccttgg ggaggggcct ggggcctccc
1141 catgcaacca gcatagcccc tactgggccc cccatgtta cccctaaag cctgaaacct
1201 gaacccccaat cctctgacag aagaacccca gggtcctgta gccctaagtg gtactaactt
1261 tccttcattc aacccacctg cgtctcatac tcacctcacc ccactgtggc tgatttggaa
```

```
1321 ttttgtgccc ccatgtaagc accccttcat ttggcattcc ccacttgaga attacccttt 1381 tgccccgaac atgttttct tctccctcag tctggccctt ccttttcgca ggattcttcc 1441 tccctccctc tttccctccc ttcctctttc catctaccct ccgattgttc ctgaaccgat 1501 gagaaataaa gtttctgttg ataatcatca aaaaaaaaa  aaaaaaaaaa aaaaaaaaaa
```

The corresponding human amino acid sequence encoding an exemplary Il2-rg gene of the disclosure consist or comprises, Genbank Accession number: NP_000197.1:

(SEQ ID NO: 29)
```
  1 mlkpslpfts llflqlpllg vglnttiltp ngnedttadf flttmptdsl svstlplpev 61 qcfvfnveym nctwnsssep qptnltlhyw yknsdndkvq kcshylfsee itsgcqlqkk 121 eihlyqtfvv qlqdpreprr qatqmlklqn lvipwapenl tlhklsesql elnwnnrfln 181 hclehlvqyr tdwdhswteq svdyrhkfsl psvdgqkryt frvrsrfnpl cgsaqhwsew 241 shpihwgsnt skenpflfal eavvisvgsm gliisllcvy fwlertmpri ptlknledlv 301 teyhgnfsaw sgvskglaes lqpdyserlc lvseippkgg algegpgasp cnqhspywap 361 pcytlkpet
```

A murine nucleic sequence encoding an exemplary Il2-rg gene of the disclosure consist or comprises, Genbank Accession number: NM_013563.4:

(SEQ ID NO: 30)
```
   1 aggaaatgta tgggtgggga gggcttgtgg gagagtggtt cagggttctg acacagacta 61 cacccagaga aagaagagca agcaccatgt tgaaactatt attgtcacct agatccttct 121 tagtccttca gctgctcctg ctgagggcag ggtggagctc caaggtcctc atgtccagtg 181 cgaatgaaga catcaaagct gatttgatcc tgacttctac agcccctgaa cacctcagtg 241 ctcctactct gccccttcca gaggttcagt gctttgtgtt caacatagag tacatgaatt 301 gcacttggaa tagcagttct gagcctcagg caaccaacct cacgctgcac tataggtaca 361 aggtatctga taataataca ttccaggagt gcagtcacta tttgttctcc aaagagatta 421 cttctggctg tcagatacaa aaagaagata ccagctcta ccagacattt gttgtccagc 481 tccaggaccc ccagaaaccc cagaggcgag ctgtacagaa gctaaaccta cagaatcttg 541 tgatcccacg ggctccagaa aatctaacac tcagcaatct gagtgaatcc cagctagagc 601 tgagatggaa aagcagacat attaaagaac gctgtttaca atacttggtg cagtaccgga 661 gcaacagaga tcgaagctgg acggaactaa tagtgaatca tgaacctaga ttctccctgc 721 ctagtgtgga tgagctgaaa cggtacacat ttcgggttcg gagccgctat aacccaatct 781 gtggaagttc tcaacagtgg agtaaatgga gccagcctgt ccactggggg agtcatactg 841 tagaggagaa tccttccttg tttgcactgg aagctgtgct tatccctgtt ggcaccatgg 901 ggttgattat taccctgatc tttgtgtact gttggttgga acgaatgcct ccaattcccc 961 ccatcaagaa tctagaggat ctggttactg aataccaagg gaacttttcg gcctggagtg 1021 gtgtgtctaa agggctgact gagagtctgc agccagacta cagtgaacgg ttctgccacg 1081 tcagcgagat tcccccaaa ggaggggccc taggagaggg gcctggaggt tctccttgca 1141 gcctgcatag cccttactgg cctccccat gttattctct gaagccggaa gcctgaacat 1201 caatcctttg atggaacctc aaagtcctat agtcctaagt gacgctaacc tcccctactc 1261 accttggcaa tctggatcca atgctcactg ccttcccttg gggctaagtt tcgatttcct
```

```
-continued
1321 gtcccatgta actgcttttc tgttccatat gccctacttg agagtgtccc ttgccctctt 1381 tccctgcaca agccctccca tgcccagcct aacacctttc cactttcttt gaagagagtc 1441 ttaccctgta gcccagggtg gctgggagct cactatgtag gccaggttgg cctccaactc 1501 acaggctatc ctcccacctc tgcctcataa gagttggggt tactggcatg caccaccaca 1561 cccagcatgg tccttctctt ttataggatt ctccctccct ttttctacct atgattcaac 1621 tgtttccaaa tcaacaagaa ataaagtttt taaccaatga tca
```

The corresponding murine amino acid sequence encoding an exemplary Il2-rg gene of the disclosure consist of Genbank Accession number: NP_038591.1:

```
                                                          (SEQ ID NO: 31)
  1 mlklllsprs flvlqllllr agwsskvlms sanedikadl iltstapehl saptlplpev 61 qcfvfnieym nctwnsssep qatnltlhyr ykvsdnntfq ecshylfske itsgcqiqke 121 diqlyqtfvv qlqdpqkpqr ravqklnlqn lviprapenl tlsnlsesql elrwksrhik 181 erclqylvqy rsnrdrswte livnheprfs lpsvdelkry tfrvrsrynp icgssqqwsk 241 wsqpvhwgsh tveenpslfa leavlipvgt mgliitlifv ycwlermppi ppiknledlv 301 teyqgnfsaw sgvskgltes lqpdyserfc hvseippkgg algegpggsp cslhspywpp 361 pcyslkpea
```

A human nucleic sequence encoding an exemplary Rag2 gene of the disclosure consist or comprises, Genbank Accession number: NM_000536.3:

```
                                                          (SEQ ID NO: 32)
   1 attagatcag tgttcataag aacatctgta ggcacacata cacactctct ttacagtcag 61 ccttctgctt gccacagtca tagtgggcag tcagtgaatc ttccccaagt gctgacaatt 121 aatacctggt ttagcggcaa agattcagag aggcgtgagc agcccctctg gccttcagac 181 aaaaatctac gtaccatcag aaactatgtc tctgcagatg gtaacagtca gtaataacat 241 agccttaatt cagccaggct ctcactgatg aattttgat ggacaagttt tcttcttttgg 301 acaaaaaggc tggcccaaaa gatcctgccc cactggagtt ttccatctgg atgtaaagca 361 taaccatgtc aaactgaagc ctacaatttt ctctaaggat tcctgctacc tccctcctct 421 tcgctacccca gccacttgca cattcaaagg cagcttggag tctgaaaagc atcaatacat 481 catccatgga gggaaaacac caaacaatga ggtttcagat aagatttatg tcatgtctat 541 tgtttgcaag aacaacaaaa aggttacttt tcgctgcaca gagaaagact tggtaggaga 601 tgttcctgaa gccagatatg gtcattccat taatgtggtg tacagccgag ggaaaagtat 661 gggtgttctc tttggaggac gctcatacat gccttctacc cacagaacca cagaaaaatg 721 gaatagtgta gctgactgcc tgccctgtgt tttcctggtg gattttgaat tgggtgtgc 781 tacatcatac attcttccag aacttcagga tgggctatct tttcatgtct ctattgccaa 841 aaatgacacc atctatattt taggaggaca ttcacttgcc aataatatcc ggcctgccaa 901 cctgtacaga ataagggttg atcttccct gggtagccca gctgtgaatt gcacagtctt 961 gccaggagga atctctgtct ccagtgcaat cctgactcaa actaacaatg atgaatttgt 1021 tattgttggt ggctatcagc ttgaaaatca aaaagaatg atctgcaaca tcatctcttt 1081 agaggacaac aagatagaaa ttcgtgagat ggagacccca gattggaccc agacattaa 1141 gcacagcaag atatggtttg gaagcaacat gggaaatgga actgttttc ttggcatacc
```

-continued

```
1201 aggagacaat aaacaagttg tttcagaagg attctatttc tatatgttga aatgtgctga 1261 agatgatact aatgaagagc agacaacatt cacaaacagt caaacatcaa cagaagatcc 1321 aggggattcc actccctttg aagactctga agaattttgt ttcagtgcag aagcaaatag 1381 ttttgatggt gatgatgaat tgacaccta taatgaagat gatgaagaag atgagtctga 1441 gacaggctac tggattacat gctgccctac ttgtgatgtg gatatcaaca cttgggtacc 1501 attctattca actgagctca acaaacccgc catgatctac tgctctcatg gggatgggca 1561 ctgggtccat gctcagtgca tggatctggc agaacgcaca ctcatccatc tgtcagcagg 1621 aagcaacaag tattactgca atgagcatgt ggagatagca agagctctac acactcccca 1681 aagagtccta cccttaaaaa agcctccaat gaaatccctc cgtaaaaaag gttctggaaa 1741 aatcttgact cctgccaaga aatcctttct tagaaggttg tttgattagt tttgcaaaag 1801 cctttcagat tcaggtgtat ggaatttttg aatctatttt taaaatcata acattgattt 1861 taaaaataca tttttgttta tttaaaatgc ctatgttttc ttttagttac atgaattaag 1921 ggccagaaaa aagtgtttat aatgcaatga taaataaagt cattctagac cctatacatt 1981 ttgaaaatat tttacccaaa tactcaattt actaatttat tcttcactga ggatttctga 2041 tctgatttt tattcaacaa accttaaaca cccagaagca gtaataatca tcgaggtatg 2101 tttatattta ttatataagt cttggtaaca aataacctat aaagtgttta tgacaaattt 2161 agccaataaa gaaattaaca cccaaaagaa ttaaattgat tattttgtgc aacataacaa 2221 ttcggcagtt ggccaaaact taaaagcaag atctactaca tcccacatta gtgttcttta 2281 tataccttca agcaacccctt tggattatgc ccatgaacaa gttagtttct catagcttta 2341 cagatgtaga tataaatata aatatatgta tacatataga tagataatgt tctccactga 2401 cacaaaagaa gaaataaata atctacatca aaaaaaaaaa aaaaaaaaaa aaaaaaa
```

The corresponding human amino acid sequence encoding an exemplary Rag2 gene of the disclosure consist or comprises, Genbank Accession number: NP_000527.2:

(SEQ ID NO: 33)
```
  1 mslqmvtvsn nialiqpgfs lmnfdgqvff fgqkgwpkrs cptgvfhldv khnhvklkpt
 61 ifskdscylp plrypatctf kgslesekhq yiihggktpn nevsdkiyvm sivcknnkkv
121 tfrctekdlv gdvpearygh sinvvysrgk smgvlfggrs ympsthrtte kwnsvadclp
181 cvflvdfefg catsyilpel qdglsfhvsi akndtiyilg ghslannirp anlyrirvdl
241 plgspavnct vlpggisvss ailtqtnnde fvivggyqle nqkrmicnii slednkieir
301 emetpdwtpd ikhskiwfgs nmgngtvflg ipgdnkqvvs egfyfymlkc aeddtneeqt
361 tftnsqtste dpgdstpfed seefcfsaea nsfdgddefd tyneddeede setgywitcc
421 ptcdvdintw vpfystelnk pamiycshgd ghwvhaqcmd laertlihls agsnkyycne
481 hveiaralht pqrvlplkkp pmkslrkkgs gkiltpakks flrrlfd
```

A murine nucleic sequence encoding an exemplary Rag2 gene of the disclosure consist or comprises, Genbank Accession number: NM_009020.3:

(SEQ ID NO: 34)
```
  1 actctaccct gcagccttca gcttggcaca aactaaacag tgactcttcc ccaagtgccg 61 agtttaattc ctggcttggc cgaaaggatt cagagaggga taagcagccc ctctggcctt 121 cagtgccaaa ataagaaaga gtatttcaca tccacaagca ggaagtacac ttcatacctc
```

-continued

```
 181 tctaagataa aagacctatt cacaatcaaa aatgtccctg cagatggtaa cagtgggtca
 241 taacatagcc ttaattcaac caggcttctc acttatgaat tttgatggcc aagtttctt
 301 ctttggccag aaaggctggc ctaagagatc ctgtcctact ggagtctttc attttgatat
 361 aaaacaaaat catctcaaac tgaagcctgc aatcttctct aaagattcct gctacctccc
 421 acctcttcgt tatccagcta cttgctcata caaaggcagc atagactctg acaagcatca
 481 atatatcatt cacggaggga aaacaccaaa caatgagctt ccgataaga tttatatcat
 541 gtctgtcgct tgcaagaata acaaaaaagt tactttccgt tgcacagaga aagacttagt
 601 aggagatgtc cctgaaccca gatacggcca ttccattgac gtggtgtata gtcgagggaa
 661 aagcatgggt gttctctttg gaggacgttc atacatgcct tctacccaga gaaccacaga
 721 aaaatggaat agtgtagctg actgcctacc ccatgttttc ttgatagatt ttgaatttgg
 781 gtgtgctaca tcatatattc tcccagaact tcaggatggg ctgtcttttc atgtttctat
 841 tgccagaaac gataccgttt atattttggg aggacactca cttgccagta atatacgccc
 901 tgctaacttg tatagaataa gagtggacct tcccctgggt accccagcag tgaattgcac
 961 agtcttgcca ggaggaatct ctgtctccag tgcaatcctc actcaaacaa acaatgatga
1021 atttgttatt gtgggtggtt atcagctgga aaatcagaaa aggatggtct gcagccttgt
1081 ctctctaggg gacaacacga ttgaaatcag tgagatggag actcctgact ggacctcaga
1141 tattaagcat agcaaaatat ggtttggaag caacatggga aacgggacta ttttccttgg
1201 cataccagga gacaataagc aggctatgtc agaagcattc tatttctata ctttgagatg
1261 ctctgaagag gatttgagtg aagatcagaa aattgtctcc aacagtcaga catcaacaga
1321 agatcctggg gactccactc cctttgaaga ctcagaggaa ttttgtttca gtgctgaagc
1381 aaccagtttt gatggtgacg atgaatttga cacctacaat gaagatgatg aagatgacga
1441 gtctgtaacc ggctactgga taacatgttg ccctacttgt gatgttgaca tcaatacctg
1501 ggttccgttc tattcaacgg agctcaataa acccgccatg atctattgtt ctcatgggga
1561 tgggcactgg gtacatgccc agtgcatgga tttggaagaa cgcacactca tccacttgtc
1621 agaaggaagc aacaagtatt attgcaatga acatgtacag atagcaagag cattgcaaac
1681 tcccaaaaga aaccccccct tacaaaaacc tccaatgaaa tccctccaca aaaaaggctc
1741 tgggaaagtc ttgactcctg ccaagaaatc cttccttaga agactgtttg attaatttag
1801 caaaagcccc tcagactcag gtatattgct ctctgaatct actttcaatc ataaacatta
1861 ttttgatttt tgtttactga aatctctatg ttatgtttta gttatgtgaa ttaagtgctg
1921 ttgtgattta ttgttaagta taactattct aatgtgtgtt ttttaacatc ttatccagga
1981 atgtcttaaa tgagaaatgt tatacagttt tccattaagg atatcagtga taaagtatag
2041 aactcttaca ttattttgta acaatctaca tattgaatag taactaaata ccaataaata
2101 aactaatgca caaaaagtta agttcttttg tgtaataagt agcctatagt tggtttaaac
2161 agttaaaacc aacagctata tcccacacta ctgctgttta taaattttaa ggtggcctct
2221 ggtttatact tatgagcaga attatatata ttggtcaata ccatgaagaa aaatttaatt
2281 ctatatcaag ccaggcatgg tgatggtgat acatgcctgt aatcctggca cttaggaagt
2341 ggaagaagga agtttgtgag tttgatgctt gttgaggtat gaccttttgc tatgtattgt
2401 agtgtatgag ccccaagacc tgcttgaccc agagacaaga gagtccacac atagatccaa
2461 gtaatgctat gtgaccttgc ccccggtta cttgtgatta ggtgaataaa gatgtcaaca
2521 gccaatagct gggcagaaga gccaaaagtg gggattgagg gtaccctggc ttgatgtagg
2581 aggagaccat gaggaaaggg gagaaaaaag tgatggagga ggagaaagat gccatgagct
```

-continued

```
2641 aggagttaag aaagcatggc catgagtgct ggccaattgg agttaagagc agcccagatg 2701 aaacatagta agtaataact cagggttatc gatagaaaat agattttagt gccgtactct 2761 ccccagccct agagctgact atggcttact gtaaatataa agtttgtatg tgtcttttat 2821 ccaggaacta aatggtcaaa ggtggagtag aaactctgga ttgggattaa attttctac 2881 aacaaatgct ggcctgggct agattttatc tcatatccga aggctgacag aacacagagc 2941 actggtaaca ttgccacctg ccatgcacaa agacctgagt ctaatactgt ggacattttc 3001 ttgaagtatc tacatgtact tctggagtga aaacatattc caacaatatg cctttgttta 3061 aatcactcac tcactttggg ccctcacatt atatcctttc aaaatcaatg gttcacccct 3121 ttgaaaatgc ttagccatag tccctcatct tccttaaaga cagttgtcat ctctggaaat 3181 agtcacatgt cattcaaggt ccaatactgt gcagctctga agtatggcat taccacttta 3241 agtgaaaagt gaaatatgaa catgagctca gacaaaggtt tgggactatc actctcaagg 3301 aggctctact gctaagtcct gaactgcttt cacatgaata cagaaattat aacaaaaaat 3361 atgtaatcaa taaaaagaaa actttcatat tcc
```

The corresponding amino acid sequence encoding an exemplary Rag2 gene of the disclosure consist or comprises of gene consist of, Genbank Accession number: NP_033046.1:

(SEQ ID NO: 35)
```
  1 mslqmvtvgh nialiqpgfs lmnfdgqvff fgqkgwpkrs cptgvfhfdi kqnhlklkpa 61 ifskdscylp plrypatcsy kgsidsdkhq yiihggktpn nelsdkiyim svacknnkkv 121 tfrctekdlv gdvpeprygh sidvvysrgk smgvlfggrs ympstqrtte kwnsvadclp 181 hvflidfefg catsyilpel qdglsfhvsi arndtvyilg ghslasnirp anlyrirvdl 241 plgtpavnct vlpggisvss ailtqtnnde fvivggyqle nqkrmvcslv slgdntieis 301 emetpdwtsd ikhskiwfgs nmgngtiflg ipgdnkqams eafyfytlrc seedlsedqk 361 ivsnsqtste dpgdstpfed seefcfsaea tsfdgddefd tyneddedde svtgywitcc 421 ptcdvdintw vpfystelnk pamiycshgd ghwvhaqcmd leertlihls egsnkyycne 481 hvqiaralqt pkrnpplqkp pmkslhkkgs gkvltpakks flrrlfd
```

A human nucleic sequence encoding an exemplary Fah gene of the disclosure consist or comprises of gene consist of, Genbank Accession number: NM_000137.2:

(SEQ ID NO: 36)
```
  1 gagaccaaaa gtcaggtagg agcctccggg gtccctgctg tgtcacccgg acaggccgtg 61 ggggcgggca gggggcggg gccgggcctg accacagcg ccgagttcag tcctgctctc 121 cgcacgccac cttaggcccg cagccgtgcc gggtgctctt cagcatgtcc ttcatcccgg 181 tggccgagga ttccgacttc cccatccaca acctgcccta cggcgtcttc tcgaccagag 241 gcgacccaag accgaggata ggtgtggcca ttggcgacca gatcctggac ctcagcatca 301 tcaagcacct ctttactggt cctgtcctct ccaaacacca ggatgtcttc aatcagccta 361 cactcaacag cttcatgggc ctgggtcagg ctgcctggaa ggaggcgaga gtgttcttgc 421 agaacttgct gtctgtgagc caagccaggc tcagagatga caccgaactt cggaagtgtg 481 cattcatctc ccaggcttct gccacgatgc accttccagc caccatagga gactacacag 541 acttctattc ctctcggcag catgctacca acgtcggaat catgttcagg gacaaggaga
```

-continued

```
 601 atgcgttgat gccaaattgg ctgcacttac cagtgggcta ccatggccgt gcctcctctg
 661 tcgtggtgtc tggcacccca atccgaaggc ccatgggaca gatgaaacct gatgactcta
 721 agcctcccgt atatggtgcc tgcaagctct tggacatgga gctggaaatg cttttttg
 781 taggccctgg aaacagattg ggagagccga tccccatttc caaggcccat gagcacattt
 841 ttggaatggt cctatgaac gactggagtg cacgagacat tcagaagtgg gagtatgtcc
 901 ctctcgggcc attccttggg aagagttttg ggaccactgt ctctccgtgg gtggtgccca
 961 tggatgctct catgcccttt gctgtgccca cccgaagca ggaccccagg cccctgccgt
1021 atctgtgcca tgacgagccc tacacatttg acatcaacct ctctgttaac ctgaaaggag
1081 aaggaatgag ccaggcggct accatatgca agtccaattt taagtacatg tactggacga
1141 tgctgcagca gctcactcac cactctgtca acggctgcaa cctgcggccg ggggacctcc
1201 tggcttctgg gaccatcagc gggccggagc cagaaaactt cggctccatg ttggaactgt
1261 cgtggaaggg aacgaagccc atagacctgg ggaatggtca gaccaggaag tttctgctgg
1321 acggggatga agtcatcata acagggtact gccaggggga tggttaccgc atcggctttg
1381 gccagtgtgc tggaaaagtg ctgcctgctc tcctgccatc atgagatttt ctctgctctt
1441 ctggaaacaa agggctcaag caccccttc aaccctgtga ctggggtcct ccctcgggct
1501 gtaggcctgg tccgccattc agtgacaaat aaagccattg tgctctgagg cctgcactgc
1561 cgcagatgca gctgtgtcca cttatgatcg tgatttgatc cagtgggtca aggtgtgtaa
1621 agcctccctg ccagatattc attaatatgt tttctcactc ttattagtga ggtcagggt
1681 ctttgtggga ttttcttatt agacatccca ggcctcctgg tattccatgg aatttgaaaa
1741 gagactggca cctgtagtag tcagggctct ccagagaaat agaaccaagg agaaagaaaa
1801 aaaaaaaaa
```

The corresponding human amino acid sequence encoding an exemplary Fah gene of the disclosure consist or comprises of gene consist of, Genbank Accession number: NP_000128.1:

```
                                                          (SEQ ID NO: 37)
  1 msfipvaeds dfpihnlpyg vfstrgdprp rigvaigdqi ldlsiikhlf tgpvlskhqd
 61 vfnqptlnsf mglgqaawke arvflqnlls vsqarlrddt elrkcafisq asatmhlpat
121 igdytdfyss rqhatnvgim frdkenalmp nwlhlpvgyh grassvvvsg tpirrpmgqm
181 kpddskppvy gacklldmel emaffvgpgn rlgepipisk ahehifgmvl mndwsardiq
241 kweyvplgpf lgksfgttvs pwvvpmdalm pfavpnpkqd prplpylchd epytfdinls
301 vnlkgegmsq aaticksnfk ymywtmlqql thhsvngcnl rpgdllasgt isgpepenfg
361 smlelswkgt kpidlgngqt rkflldgdev iitgycqgdg yrigfgqcag kvlpallps
```

```
                                                          (SEQ ID NO: 38)
  1 gggtgctaaa agaatcacta gggtggggag gcggtcccag tggggcgggt aggggtgtgt
 61 gccaggtggt accgggtatt ggctggagga agggcagccc ggggttcggg gcggtccctg
121 aatctaaagg ccctcggcta gtctgatcct tgccctaagc atagtcccgt tagccaaccc
181 cctacccgcc gtgggctctg ctgcccggtg ctcgtcagca tgtcctttat tccagtggcc
241 gaggactccg actttcccat ccaaaacctg ccctatggtg ttttctccac tcaaagcaac
301 ccaaagccac ggattggtgt agccatcggt gaccagatct tggacctgag tgtcattaaa
361 cacctctttta ccggacctgc cctttccaaa catcaacatg tcttcgatga gacaactctc
```

```
 421 aataacttca tgggtctggg tcaagctgca tggaaggagg caagagcatc cttacagaac 481 ttactgtctg ccagccaagc ccggctcaga gatgacaagg agcttcggca gcgtgcattc 541 acctcccagg cttctgcgac aatgcacctt cctgctacca taggagacta cacggacttc 601 tactcttctc ggcagcatgc caccaatgtt ggcattatgt tcagaggcaa ggagaatgcg 661 ctgttgccaa attggctcca cttacctgtg ggataccatg gccgagcttc ctccattgtg 721 gtatctggaa ccccgattcg aagacccatg gggcagatga gacctgataa ctcaaagcct 781 cctgtgtatg gtgcctgcag actcttagac atggagttgg aaatggcttt cttcgtaggc 841 cctgggaaca gattcggaga gccaatcccc atttccaaag cccatgaaca cattttcggg 901 atggtcctca tgaacgactg gagcgcacga gacatccagc aatgggagta cgtcccactt 961 gggccattcc tggggaaaag ctttggaacc acaatctccc cgtgggtggt gcctatggat 1021 gccctcatgc cctttgtggt gccaaaccca aagcaggacc ccaagcccttt gccatatctc 1081 tgccacagcc agccctacac atttgatatc aacctgtctg tctctttgaa aggagaagga 1141 atgagccagg cggctaccat ctgcaggtct aactttaagc acatgtactg gaccatgctg 1201 cagcaactca cacaccactc tgttaatgga tgcaacctga gacctgggga cctcttggct 1261 tctggaacca tcagtggatc agaccctgaa agctttggct ccatgctgga actgtcctgg 1321 aagggaacaa aggccatcga tgtggagcag gggcagacca ggaccttcct gctggacggc 1381 gatgaagtca tcataacagg tcactgccag ggggacggct accgtgttgg ctttggccag 1441 tgtgctggga aagtgctgcc tgccctttca ccagcctgaa gctccggaag tcacaagaca 1501 caccctttgcc ttatgaggat catgctacca ctgcatcagt caggaatgaa taaagctact 1561 ttgattgtgg gaaatgccac agaaaaaaaa aaaaaaa
```

The corresponding murine amino acid sequence encoding an exemplary Fah gene of the disclosure consist or comprises of gene consist of, Genbank Accession number: NP_034306.2:

(SEQ ID NO: 39)
```
  1 msfipvaeds dfpiqnlpyg vfstqsnpkp rigvaigdqi ldlsvikhlf tgpalskhqh 61 vfdettlnnf mglgqaawke araslqnlls asqarlrddk elrqraftsq asatmhlpat 121 igdytdfyss rqhatnvgim frgkenallp nwlhlpvgyh grassivvsg tpirrpmgqm 181 rpdnskppvy gacrlldmel emaffvgpgn rfgepipisk ahehifgmvl mndwsardiq 241 qweyvplgpf lgksfgttis pwvvpmdalm pfvvpnpkqd pkplpylchs qpytfdinls 301 vslkgegmsq aaticrsnfk hmywtmlqql thhsvngcnl rpgdllasgt isgsdpesfg 361 smlelswkgt kaidveqgqt rtflldgdev iitghcqgdg yrvgfgqcag kvlpalspa
```

The following examples are provided to better illustrate the claimed disclosure and are not to be interpreted as limiting the scope of the disclosure. To the extent that specific materials are mentioned, it is merely for purposes of illustration and is not intended to limit the disclosure. One skilled in the art may develop equivalent means or reactants without the exercise of inventive capacity and without departing from the scope of the disclosure.

EXAMPLES

Example 1: Generation of the Por-Floxed Mouse Strain

Figure 17:
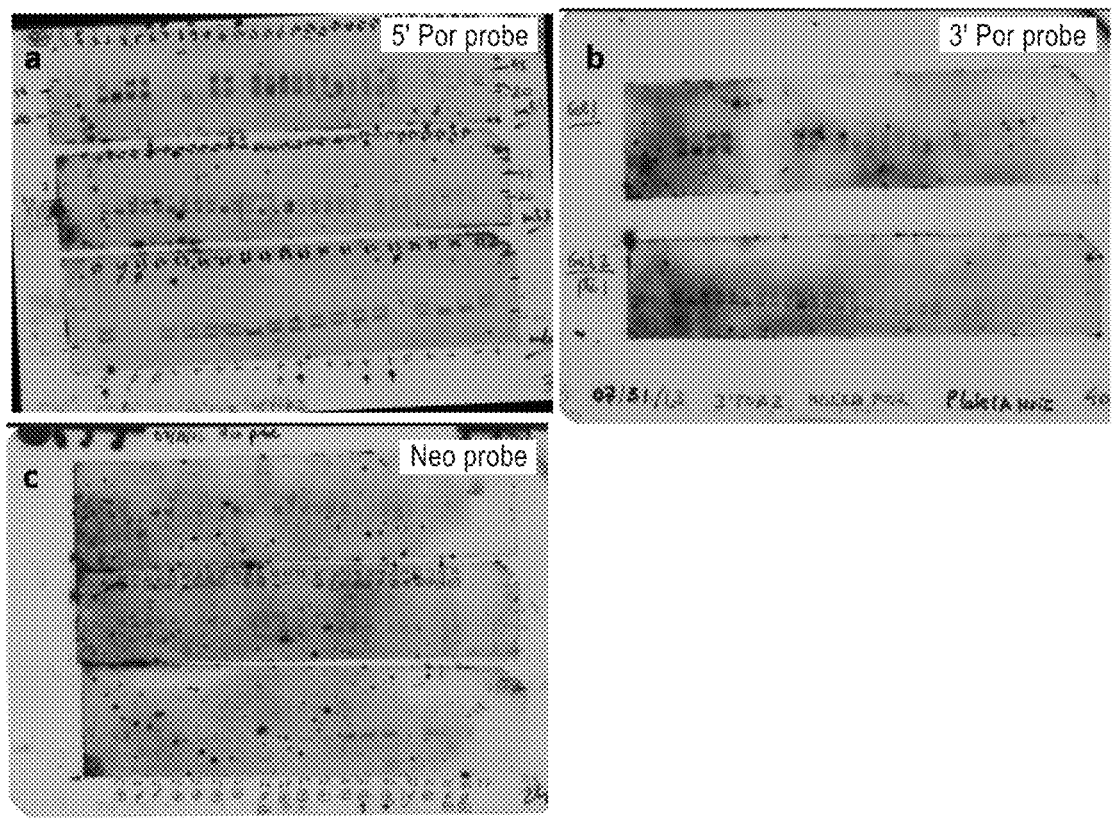
FIG. 17 is a Southern blot image of targeted ESCs.

Por knock-out first targeting vector was purchased from the National Institutes of Health (NIH) Knock-Out Mouse Program (KOMP) (FIG. 4A). The vector was linearization with the AsisI restriction enzyme, and DNA was electroporated into Jm8A3 mouse embryonic stem cells (ESC) (Pettitt, S. J. et al. "Agouti C57BL/6N embryonic stem cells for mouse genetic resources." Nat Methods 6, 493-495 (2009)) by the Mouse Embryonic Stem Cell Core at Baylor College of Medicine. Integrated clones were selected using neomycin resistance. DNA of ESC clones was digested with NSiI restriction enzyme and screened for site specific integration by Southern blotting using DIG nonisotopic detection system (Roche Applied Biosciences) following the manufacturer's instructions (full blots in FIG. 17). The 500 bp-size 5' and 3' probes that bind outside the vector's homology arms were synthesized using the following set of primers.

```
5' POR Fw2   GGCCTCAGAGAGGACATAGTGCCC      (SEQ ID NO: 1)

5' POR Rev2  GCCCTCTGGTGTCAGGTCC           (SEQ ID NO: 2)

3' POR Fw2   CCTCACGCAGCTTAATGTGGCC        (SEQ ID NO: 3)

3' POR Rev2  GGAAGTTAAGGACGTGATTACAGGGAGC  (SEQ ID NO: 4)
```

Correctly targeted ESCs cells were injected into C57/BL blastocysts by the Genetically Engineered Mouse Core at Baylor College of Medicine. The male chimeras were bred with C57/BL albino females (Taconic) to access germline transmission of targeted ESC. To remove the FRT-flanked LacZ and the neomycin cassette and generate a conditional POR knock-out strain, the mice were crossed with a Rosa26-FLPe strain (Farley, F. W., Soriano, P., Steffen, L. S. & Dymecki, S. M. "Widespread recombinase expression using FLPeR (flipper) mice." Genesis 28, 106-110 (2000)). Genotyping was performed by Transnetyx (Cordova, Tenn.).

Example 2: X-Gal Staining

Embryos and fresh liver sections were fixed in 4% PFA for 1 hour at 4° C. and washed 2×30 min in X-Gal rinse buffer (PBS 1× with 0.02% Igepal and 0.01% deoxycholate) followed by overnight incubation with X-Gal staining solution (PBS 1× with 5 mM $K_3Fe(CN)_6$, 5 mM $K_4Fe(CN)_6$, 0.02% Igepal, 0.01% deoxycholate, 2 mM $MgCl_2$, 5 mM EGTA and 1 mg/ml of fresh X-Gal). Samples were post-fixed overnight in 4% PFA at 4° C.

Example 3: Generating of the PIRF ($Por^{c/c}$-/Il2rg-/-/Rag2-/-/Fah-/-) Mouse Strain Six gRNA sequences targeting critical exons of the Rag2, 112-rg or Fah gene were selected (FIG. 1A, FIG. 6 and FIG. 7) using two different online tools (crispr.mit.edu and COSMID) (Cradick, T. J., Qiu, P., Lee, C. M., Fine, E. J. & Bao, G. "COSMID: A Web-based Tool for Identifying and Validating CRISPR/Cas Off-target Sites." Molecular therapy. Nucleic acids 3, e214 (2014)). Complementary oligonucleotides were annealed and ligated into the DR274 vector (Addgene plasmid #42250) (Hwang, W. Y. et al. "Efficient genome editing in zebrafish using a CRISPR-Cas system." Nat Biotechnol 31, 227-229 (2013)) using standard molecular cloning techniques with the restriction enzyme BsaI (NEB) and T4 DNA Ligase (NEB). A T7 bacterial promoter sequence was inserted into the pX330-U6-Chimeric_BB-CBh-hSpCas9vector (Addgene plasmid #42230) (Cong, L. et al. "Multiplex genome engineering using CRISPR/Cas systems." Science 339, 819-823 (2013)) upstream of the Cas9 transcription start site using standard molecular cloning techniques. DR274 vectors were cut using DraI (NEB) and gel purified using the Zymoclean Gel DNA Recovery Kit (Zymo, Cat #11-301). In vitro transcription of sgRNA was performed using the MEGAshortscript T7 Transcription Kit (Life Technologies, AM1354), according to manufacturer's instructions. The resulting RNA was purified using the RNA Clean & Concentrator-5 (Zymo, R1015) and eluted in RNAse-free water. Synthesis was verified by polyacrylamide gel electrophoresis. pX330 (with T7 promoter) was digested with NcoI and NotI, and gel purified. Cas9 mRNA was synthesized from the digested pX330-T7 vector using the mMessage mMachine T7 ULTRA Kit (life tech AM1345), according to the manufacturer's protocol. Polyadenylation was verified by denaturing agarose gel electrophoresis (1% agarose and 6.6% formaldehyde in MOPS buffer).

Zygotes from Por c/c mice were injected with S. pyogenes Cas9 mRNA (60 ng/ul) and the six gRNA (15 ng/uL each). All viable zygotes were implanted into 3 pseudopregnant females. To detect the deleted regions all twenty-three pups were genotyped after weaning using the following primers:

```
Fah Fw       CTGGGTTGCATACTGGTGGG     (SEQ ID NO: 5)

Fah Rev      AAACAGGGTCTTTGCTGCTG     (SEQ ID NO: 6)

Fah Int Fw   ACAAAGGTGTGGCAAGGGTT     (SEQ ID NO: 7)

Il2 Fw       CCACCGGAAGCTACGACAAA     (SEQ ID NO: 8)

Il2 Rev      GGGGGAATTGGAGGCATTCT     (SEQ ID NO: 9)

Il2 Int Rev  CTTCTTCCCGTGCTACCCTC     (SEQ ID NO: 10)

Rag2 Fw      CCTCCCACCTCTTCGTTATCC    (SEQ ID NO: 11)

Rag2 Rev     AGTCTGAGGGGCTTTTGCTA     (SEQ ID NO: 12)

Rag2 Int Fw  AGTCTGAGGGGCTTTTGCTA     (SEQ ID NO: 13)
```

Further offspring genotyping was performed by Transnetyx (Cordova, Tenn.).

Example 4: Humanization of PIRF Mice

Hepatocytes ($3\times10^6$/mouse) were transplanted into the murine liver of PIRF mice by splenic injections as originally described for mouse hepatocytes (Ponder, K. P. et al. "Mouse hepatocytes migrate to liver parenchyma and function indefinitely after intrasplenic transplantation." Proc Natl Acad Sci USA 88, 1217-1221 (1991)). In brief, the abdominal cavity was opened by a midabdominal incision, and $3\times10^6$ human hepatocytes in a volume of 100 µl PBS were injected into the spleen. Immediately after transplantation, selection pressure towards transplanted human hepatocytes was applied by withdrawing the drug nitisinone (NTBC) from the drinking water in the following steps: 2 days at 25%, then 2 days at 12% and eventually 2 days at 6% of the colony maintenance dose (100%=7.5 mg/l) prior to discontinuing the drug completely (Bissig, K. D. et al. "Human liver chimeric mice provide a model for hepatitis B and C virus infection and treatment." The Journal of clinical investigation 120, 924-930 (2010)). Mice with clinical symptoms (hunched posture, lethargy, weight loss, etc) were put back on 100% nitisinone for a few days before once again being weaned off the drug as described above. In order to determine the extent of human chimerism, human albumin (ELISA, Bethyl laboratories) in the murine blood, having previously shown that human albumin levels correlate with the level of human chimerism assessed by immunostaining of human hepatocytes was measured (Bissig, K. D. et al. (2010)). Only mice with a human chimerism >70% were further used. Where indicated, some PIRF mice were injected intravenously with 100 µl Adenovirus coding CRE recombinase under the CMV promoter (Ad5 CMV-Cre, 2.3×10$^{11}$ pfu/ml, provided by the Vector Development Laboratory at Baylor College of Medicine) either 24-hours before hepatocyte transplantation and/or when reaching high human chimerism (>70%). Available hepatocyte donor information is given in Table 2. All animal experiments were approved by the Baylor College of Medicine Institutional Animal Care and Use Committee (IACUC). All animals used for humanization (including controls) were female, due to fewer postsurgical complications.

Example 5: qPCR

Total mRNA was isolated from fresh frozen tissue samples using Purelink RNA mini kit (Invitrogen). 2 µg of total mRNA was reverse transcribed using the qScript cDNA supermix (Quanta Biosciences) and 20 ng of cDNA was used for the qPCR reactions, performed with Perfecta SYBR Green Fast Mix (Quanta Biosciences) and analyzed on ABI Prism 7900HT Sequence Detection System (Applied Biosciences). The following primers were used for Por mRNA amplification of PIRF mouse samples:

```
                                    (SEQ ID NO: 14)
mPor Fw2 GGCCCCACCTGTCAAAGAGAGCAGC (SEQ ID NO: 15)
mPor Rev1: CAAACTTGACACCCGTGAGGTCC
```

For humanized PIRF mouse liver samples, mouse Por and human POR were amplified using the following set of primers:

```
                                    (SEQ ID NO: 16)
mPor Fw1: TCTATGGCTCCCAGACGGGAACC (SEQ ID NO: 17)
mPor Rev2: CCAATCATAGAAGTCCTGCGCG (SEQ ID NO: 18)
hPOR Fw1: CCAATCATAGAAGTCCTGCGCG (SEQ ID NO: 19)
hPOR Rev5: ACCTTGGCCGCATCTATGTCGG
```

Each sample was normalized to Gapdh/GADPH as an internal control gene using the following primers:

```
                                    (SEQ ID NO: 20)
mGapdh Fw AGAACATCATCCCTGCATCCA (SEQ ID NO: 21)
mGapdh Rev CAGATCCACGACGGACACATT (SEQ ID NO: 22)
hGAPDH Fw: CAGAACATCATCCCTGCCTCTAC (SEQ ID NO: 23)
hGAPDH Rev: TTGAAGTCAGAGGAGACCACCTG
```

Example 6: RNA-Seq Libraries

Whole-transcriptome RNA sequencing (RNA-Seq) was performed using total RNA extracted from fresh-frozen liver tissue sampled from all seven liver lobes. Total RNA was isolated using the Purelink RNA mini kit (Invitrogen). Libraries were generated from total RNA according to the manufacturer's recommendation using the TrueSeq Stranded mRNA LT kit (Illumina). The libraries were sequenced on a NextSeq 500 sequencer. The average read per sample was 17 millions. RNA-Seq TPM expression values were calculated with RSEM[52] (version 1.2.17) using the read aligner Bowtie2[53] applied to the combined human and mouse NCBI Refseq (3/21/16) transcriptomes. RNA sequencing data is available from European Nucleotide Archive, ENA accession PRJEB 14714. Low-abundance cytochromes (human <20 TPM and mouse <20 TPM) were only compared if one of the experimental groups reached >20 TPM. Gene expression has been normalized to three human housekeeping genes and their murine counterparts (PSMB2, PSMB4, RAB7A and VPS2929; Psmb2, Psmb4, Rab7 and Vps29)[54]. RNA-Seq data is available from European Nucleotide Archive, ENA accession code PRJEB 14714

Example 7: Western Blot

Figure 18:
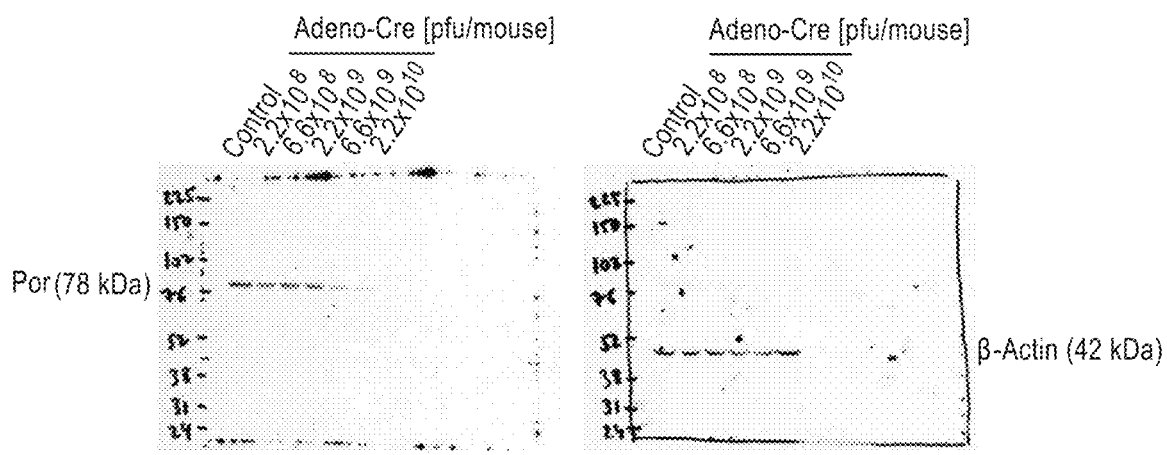
FIG. 18 is a Western blot image showing murine Por and Gadph from PIRF mice injected with Adeno-CRE.
Figure 19A:
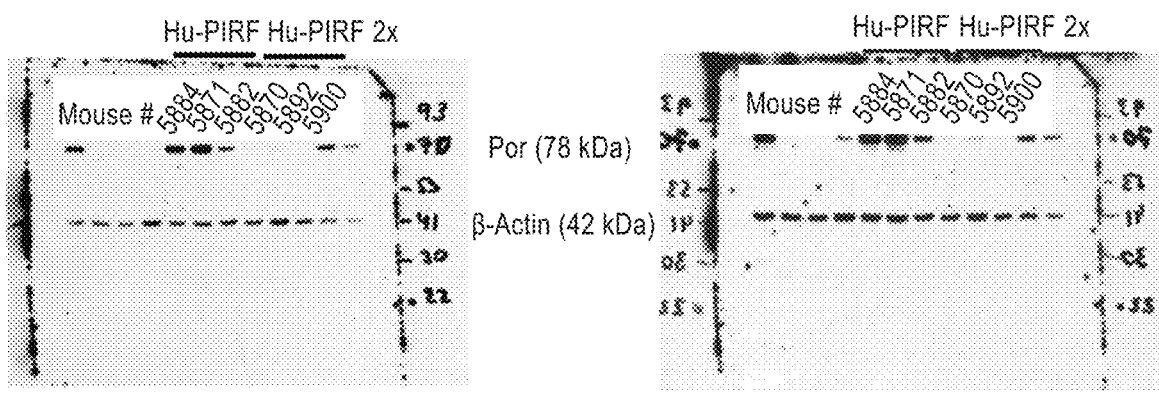
FIG. 19A-B is a Western blot image showing murine Por and Gadph from Humanized PIRF mice (a) and Por$^{c/c}$ and (b) Por$^{c/c}$/Alb-CRE mice.
Figure 19B:
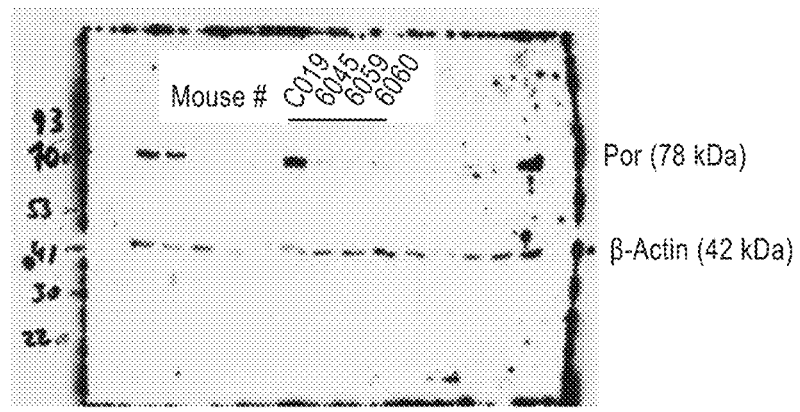

Western blotting was performed as described previously (Bissig-Choisat, B. et al. "Development and rescue of human familial hypercholesterolaemia in a xenograft mouse model." Nature communications 6, 7339 (2015)). Tissue from snap frozen liver was homogenized in RIPA buffer (Sigma, cat #R0278-50 ml) containing proteases inhibitors (Roche, cat #04693159001). 30 µg of total protein was electrophoresed in a NuPAGE 4-12% Bis Tris Gel (Invitrogen, cat #NP0336BOX) and transferred to a PVDF membrane (Millipore, cat #IPVH00010). The blot was then blocked in 5% milk, followed by primary antibody incubation. Rabbit anti-Por (Abcam cat #ab13513) or mouse anti-β-actin (Sigma cat #A1978) were diluted 1:1,000 and 1:3,000, respectively (full blots in FIG. 18 and FIG. 19). Secondary antibodies were donkey anti-rabbit IgG/HRP and donkey anti-mouse IgG/HRP (Jackson Immunoresearch Labs, cat #711-035-152 and 711-035-150) used at 1:10,000 and 1:50,000, respectively. The membrane was imaged using Amersham ECL Western Blotting Detection Reagent (General Electric Healthcare Life Sciences, cat #RPN2106).

Example 8: Immunohistochemistry

10 µm sections from cryopreserved tissue blocks were fixed with 3% PFA for 15 minutes and incubated overnight at 4° C. with the following primary antibodies: anti-Por (Abcam, cat #ab13513) diluted 1:500, anti-human Nuclei (EMD Millipore, cat #MAB 1281) diluted 1:250 in PBS containing 0.2% TritonX-100 and 0.5% BSA. Secondary antibodies (1:1,000 Alexa-fluor conjugated, Molecular Probes) were incubated for 60 min at room temperature in the same buffer. Sections were mounted with Vectashield plus DAPI (Vector Labs).

Example 9: Mouse Husbandry

All mice (6-10 months old, humanized or non-humanized) were maintained under a standard 12-h dark/light cycle with water and chow provided ad libitum. All animal experiments were approved by the Baylor College of Medicine Institutional Animal Care and Use Committee (IACUC).

Example 10: Sample Preparation for Mass Spectrometry

One group of mice was treated (i.v.) with gefitinib (10 mg/kg) and housed separately in metabolic cages for 16 h feces collection. Feces samples were weighted and homogenized in water (100 mg feces in 1,000 µl of H$_2$O). Subsequently, 300 μl of methanol was added to 100 μl of the resulting mixture, followed by centrifugation at 15,000 g for 20 min. The supernatant was transferred to a new Eppendorf vial for a second centrifugation (15,000 g for 20 min). The final concentration of agomelatine is 2 μM. Each supernatant was transferred to an auto sampler vial for analysis (described below).

For atazanavir metabolism in liver, liver samples were harvested 30 min after the treatment of atazanavir (i.v., 30 mg/kg). Briefly, livers were weighted and homogenized in water/MeOH with the internal standard agomelatine [100 mg liver in 300 ul of $H_2O$/MeOH (v/v 3:1)]. Subsequently, 300 μl of methanol was added to 100 μl of the resulting mixture, followed by centrifugation at 15,000 g for 20 min. The supernatant was transferred to a new Eppendorf vial for a second centrifugation (15,000 g for 20 min). The final concentration of agomelatine is 2 μM in samples. Each supernatant was transferred to an auto sampler vial. Five μl of each prepared sample was injected to a system combining ultra-high performance liquid chromatography (UHPLC) and quadruple time-of-flight mass spectrometry (QTOFMS) for analysis.

Example 11: Mass Spectrometry (UHPLC-QTOFMS Analyses)

Metabolites from gefitinib and atazanavir were separated using a 1260 Infinity Binary LC System (Agilent Technologies, Santa Clara, Calif.) equipped with 100 mm×2.7 mm (Agilent XDB C18) column. The column temperature was maintained at 40° C. The flow rate of was 0.3 mL/min with a gradient ranging from 2% to 98% aqueous acetonitrile containing 0.1% formic acid in a 15-min run. Quadrupole time of flight mass spectrometry (QTOFMS) was operated in positive mode with electrospray ionization. Ultra-highly pure nitrogen was applied as the drying gas (12 L/min) and the collision gas. The drying gas temperature was set at 325° C. and nebulizer pressure was kept at 35 psi. The capillary voltages were set at 3.5 kV. During mass spectrometry, real time mass correction and accurate mass were achieved by continuously measuring standard reference ions at m/z 121.0508, 922.0098 in the positive mode. Mass chromatograms and mass spectra were acquired by MassHunter Workstation data Acquisition software (Agilent, Santa Clara, Calif.) in centroid and profile formats from m/z 50 to 1000. The acquisition rate was set as 1.5 spectra per second. The method used in this study has been validated by the previous study of gefitinib metabolism in human liver microsomes[39]. Meanwhile, the quality control samples were performed every 10 samples in the process of the sample running. Due to the authentic compounds of metabolites not available, the metabolite identification was based on their exact mass and MS/MS fragments. The chromatograms and relative abundance of metabolite were performed on Qualitative Analysis software (Agilent, Santa Clara, Calif.). The relative abundance was evaluated based on integrated peak area of each metabolite.

Example 12: Statistics

Sample sizes for experiments were determined by estimated differences between groups and availability of highly humanized mice. No randomization of animals before allocation to experimental groups nor blinding of experimental groups was done. Statistical analysis was performed using PRISM version 6.0 software (Graph Pad software) using Mann-Whitney test, or ANOVA. Statistical significance was assumed with a p-value <0.05 (*). Bars in graphs represent mean±SEM unless noted otherwise. Group size (N) represents biological sample size.

Example 13: Generation of Novel Mouse Model for Hepatocyte Repopulation

In order to functionally block murine cytochrome metabolism, conditional (floxed exon 3 and 4) knock-out of the NADPH-P450 oxidoreductase (Por) gene by targeting mouse embryonic stem cells[28] was generated (FIG. 4). Injected blastocysts with properly targeted embryonic stem cells produced chimeras with germline transmission of the Por "knock-out first" allele[29]. Expression from the targeted Por locus using the lacZ expression cassette in the embryo and adult liver was confirmed (FIG. 5). Next mice were bred with a flippase-expressing strain[30] to generate a CRE recombinase conditional Por knock-out strain ($Por^e$/c). Homozygous zygotes from this strain were injected with the bacterial type II Clustered Regularly-Interspaced Short Palindromic Repeats/Cas9 (CRISPR-Cas9) system[31, 32, 33] targeting simultaneous deletion of critical exons of the Il2-rg, Rag2, and Fah genes (FIG. 6 and FIG. 7) to generate the PIRF strain (FIG. 1A). Homozygous PIRF mice are thus immunedeficient, lacking T, B and NK cells, but are healthy and fertile. Since adenoviral gene therapy vectors efficiently transduce hepatocytes in vivo, the Por gene was deleted using an adenovirus coding the CRE recombinase (Adeno-CRE). Increasing doses ($2.2\times10^{8-10}$ per mouse) of the virus were injected intravenously into PIRF mice. Quantitative RT-PCR of the Por mRNA in liver revealed efficient deletion only at high doses of adenovirus (FIG. 1B). Immunostaining for Por (FIG. 1C) confirmed these findings, although a minimal residual signal could be detected by Western blotting even at the highest dose used (FIG. 1D). Por-deleted PIRF mouse livers accumulated lipids starting about two weeks after adenoviral transduction (FIG. 2), but in contrast to the immune competent Alb-Cre/$Por^{c/c}$ strain[25, 27], without infiltration and lacking necrosis (FIG. 20). Nevertheless, residual Por expressing hepatocytes had a growth advantage over the lipid-rich Por-deleted hepatocytes, and clonal expansion of a few Por expressing cells could be detected four weeks after adenoviral transduction by immunostaining (FIG. 9).

Example 14: Characterization of Humanized PIRF Mice

Figure 12A:
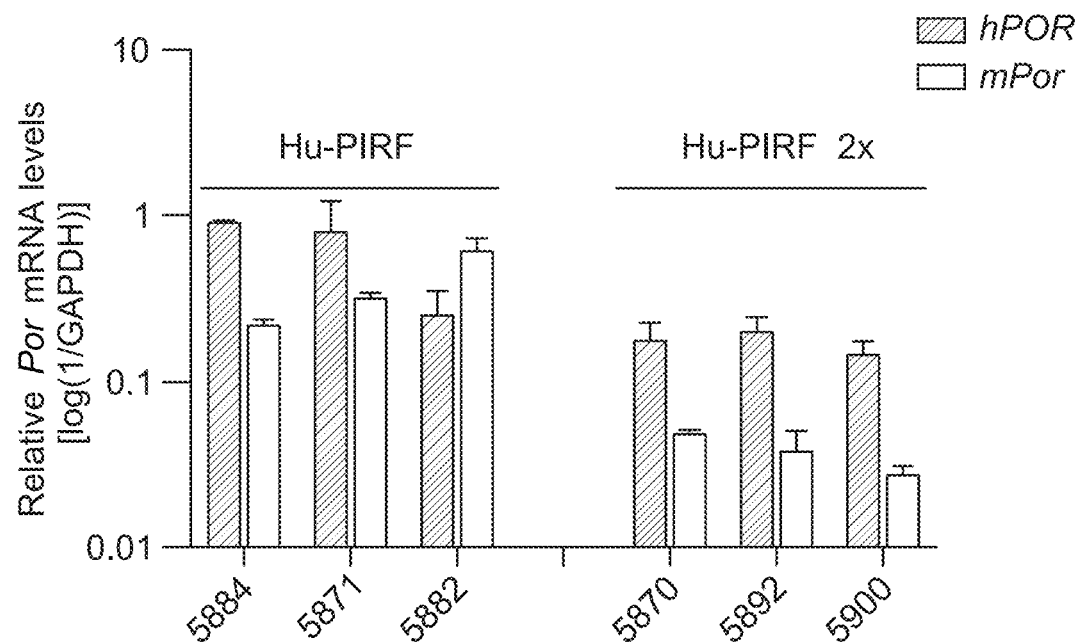
FIG. 12A is a bar graph showing qPCR of human and murine specific Por normalized to human and murine Gapdh, respectively.
Figure 12B:
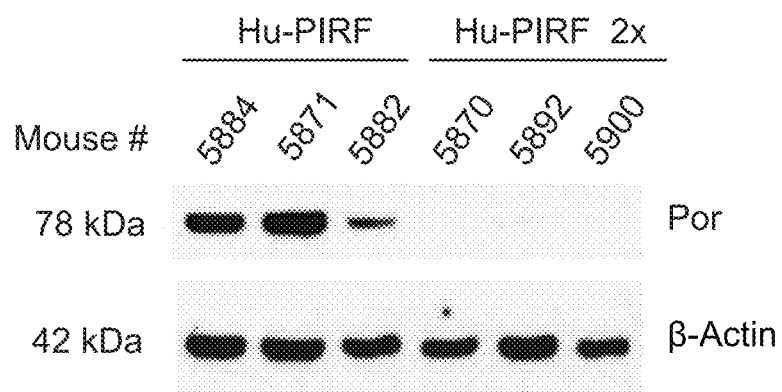
FIG. 12B is a western blot image showing murine Por and β-actin of liver samples from the same humanized mice.

Human liver chimeric mice using the PIRF strain were generated[5, 20, 34]. To ensure cytochrome P450 metabolism would be human-specific, we injected Adeno-Cre ($2.3\times10^{10}$ pfu/mouse) before human hepatocyte transplantation and an additional dose of Adeno-Cre in some highly humanized PIRF (Hu-PIRF) mice. Immunostaining revealed that an almost complete deletion of the Por gene could be achieved only in double-injected humanized PIRF (Hu-PIRF 2×) mice (FIG. 2A). Quantitative PCR and Western blotting corroborated the massive reduction of murine Por upon adenoviral delivery of CRE (FIG. 12). Gene expression profiling was performed to compare PIRF mice repopulated with human hepatocytes (Hu-PIRF) that were injected with either Adeno-CRE (Hu-PIRF 2×) or Adeno-GFP (FIG. 2B). Both groups were repopulated with human hepatocytes from the same hepatocyte donors (Table 2) to avoid inter-individual variations.

TABLE 2

Characteristics of human hepatocyte donors used in the present disclosure.

| Hepatocyte | Age* | Gender | Race | BMI | Cause of death | Usage in present study |
|---|---|---|---|---|---|---|
| #1 | 24 | Male | African American | 20.3 | Anoxia | RNAseq (chimeric mice, hepatocytes) |
| #2 | 2 | Female | African American | 19.6 | Head trauma | RNAseq (chimeric mice, hepatocytes) |
| #3 | 45 | Female | Caucasian | 20.8 | Anoxia | RNAseq (Chimeric mice) |
| #4 | 1.2 | Female | Caucasian | 20.8 | Head trauma | Gefitinib metabolites |
| #5 | 18 | Male | Caucasian | 24.3 | Cardiovascular | ATV metabolites |

*in years

Expression of the murine P450 cytochromes was clearly altered for 27 out 38 genes analyzed after Por deletion (FIG. 2C): 24 cytochromes were significantly upregulated (1.5-12.5-fold) and 3 cytochromes significantly downregulated (0.5-0.3-fold). The expression profiles of these murine cytochromes were by in large comparable to those from previous work in non-humanized, Por-deficient mice (Table 1)[35]. In the human part of the same chimeric liver, human P450 cytochromes were less altered upon deletion of murine Por (FIG. 2D). Half of the human cytochromes were only slightly altered (0.5-1.5-fold change), while the other half were moderately upregulated (1.5-2.4-fold).

Figure 2E:
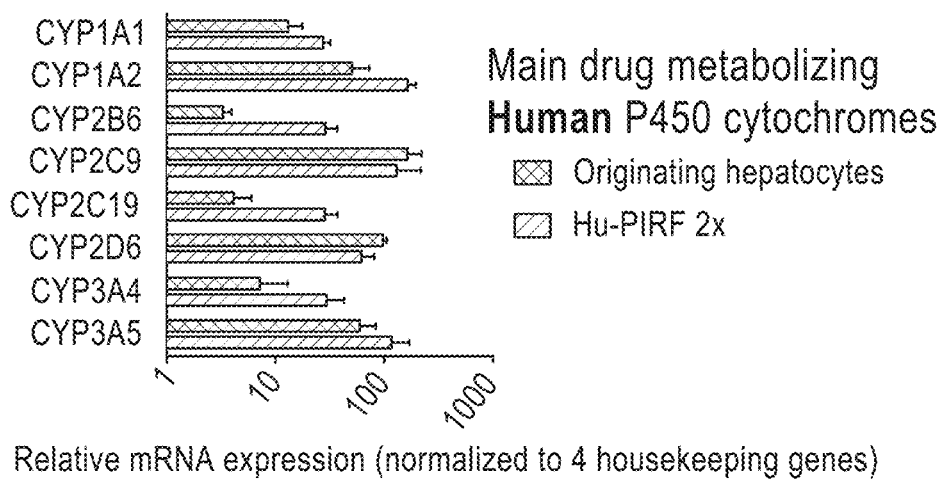

Not all human cytochromes serve an important role in xenobiotic metabolism. From the 200 most-prescribed drugs in the United States, about three-quarter are metabolized through P450 cytochromes, of which CYP3A4/5, 2C9, 2C19, 2D6 and 1A2 contribute to ~95%[36]. Comparing these human cytochrome clusters from chimeric livers (Hu-PIRF 2×) with the originating, isogenic primary hepatocytes. For this comparison, two donor hepatocytes (Table 2) and the corresponding human (isogenic) liver chimeric mice (N=6). Expression levels were similar for most clusters, and these important cytochromes were all robustly expressed in chimeric livers (FIG. 2E). Interestingly, some human clusters (CYP1A2, CYP2B6, CYP2C19 and CYP3A4) were expressed at even higher levels in the chimeric liver than in primary human hepatocytes.

Example 15: Xenobiotic Metabolism of Humanized PIRF Mice

To validate Hu-PIRF mice for human drug metabolism, xenobiotic metabolism of gefitinib[37], an inhibitor of epidermal growth factor receptor used against lung cancer and a variety of other neoplasia was used[38]. Gefitinib is metabolized primarily by the P450 cytochrome system, including CYP3A4 and 2D6. Gefitinib metabolites demonstrate considerable differences between human and mouse liver microsomes[39], but regardless of dose, route or species, gefitinib is excreted primarily in the feces (less than 7% in the urine)[40, 41]. The feces of non-humanized PIRF mice for gefitinib metabolites during the first 24 hours after intravenous injection of gefitinib was then analyzed.

Figure 13A:
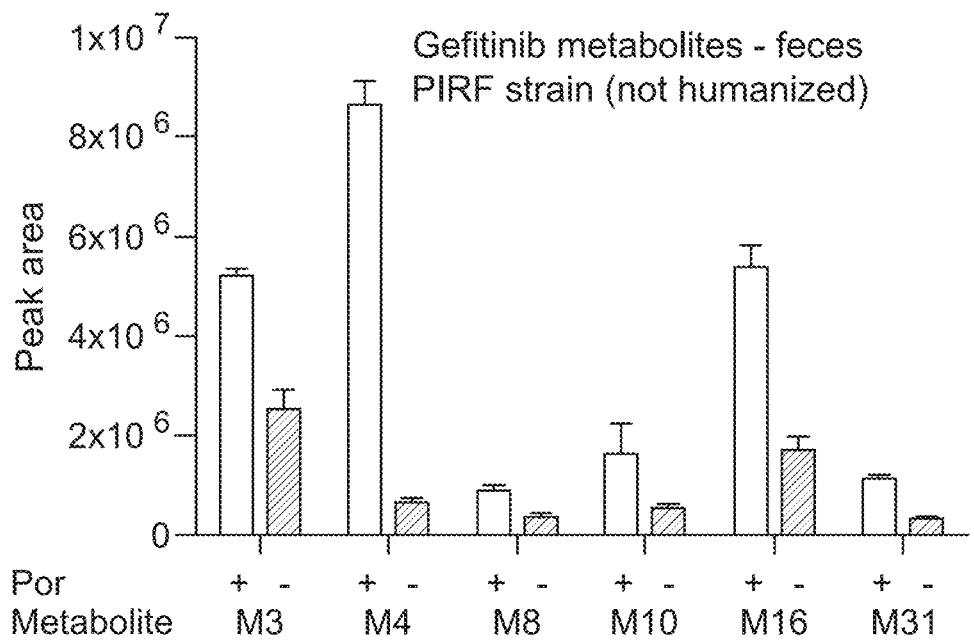
FIG. 13A is a bar graph showing deletion by adenoviral delivery of CRE.
Figure 13B:
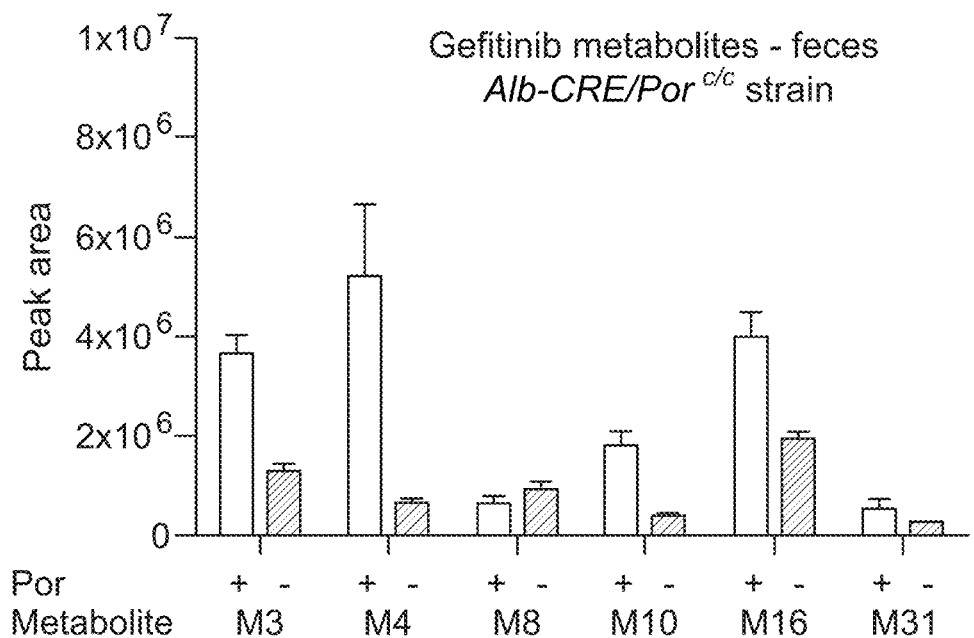
FIG. 13B is a bar graph showing by crossing of Por$^{c/c}$ with Alb-Cre mice, generating an Alb-Cre/Por$^{c/c}$ strain.
Figure 14A:
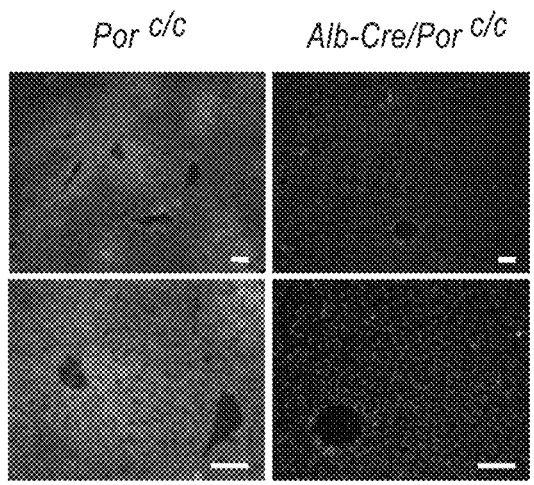
FIG. 14A is a confocal immunostaining image showing complete Por deletion.
Figure 14B:
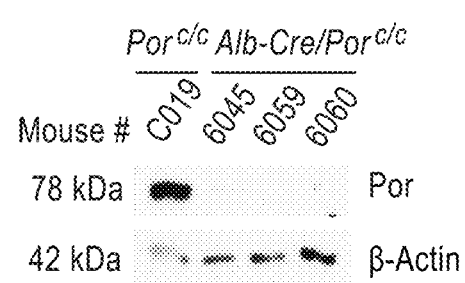
FIG. 14b is a western blot image showing Por protein liver samples from a control Porc/c mouse and three different Alb-Cre/Porc/c mice.
Figure 14C:
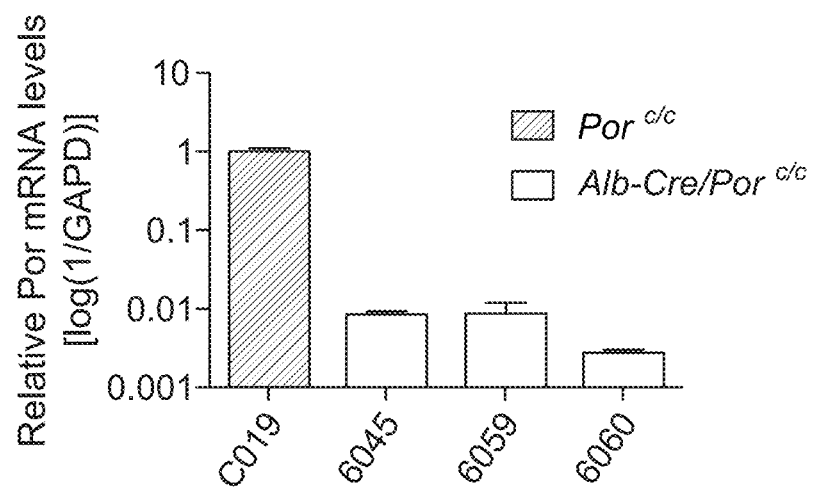
FIG. 14C is a bar graph showing qPCR of murine Por mRNA levels.

Mass spectrometry revealed a reduction of several gefitinib metabolites upon deletion of the Por gene, implying a Por-dependent P450 cytochrome deficiency for these metabolites (FIG. 3A and FIG. 13A). Since some metabolites were not significantly altered, the possibility that residual Por activity was responsible for persistent murine P450 cytochrome metabolism system was tested. The Por$^{c/c}$ strain was crossed with a transgenic mouse that expresses CRE under the Albumin promoter. Por protein in the liver of Alb-CRE/Por$^{c/c}$ animals was efficiently deleted (FIG. 14); nevertheless, the metabolite profile formed after gefitinib injection was comparable to that of PIRF mice with adenoviral deletion of Por (FIG. 13). This result similarity indicates that gefitinib has both P450-dependent and -independent drug metabolism.

Figure 10:
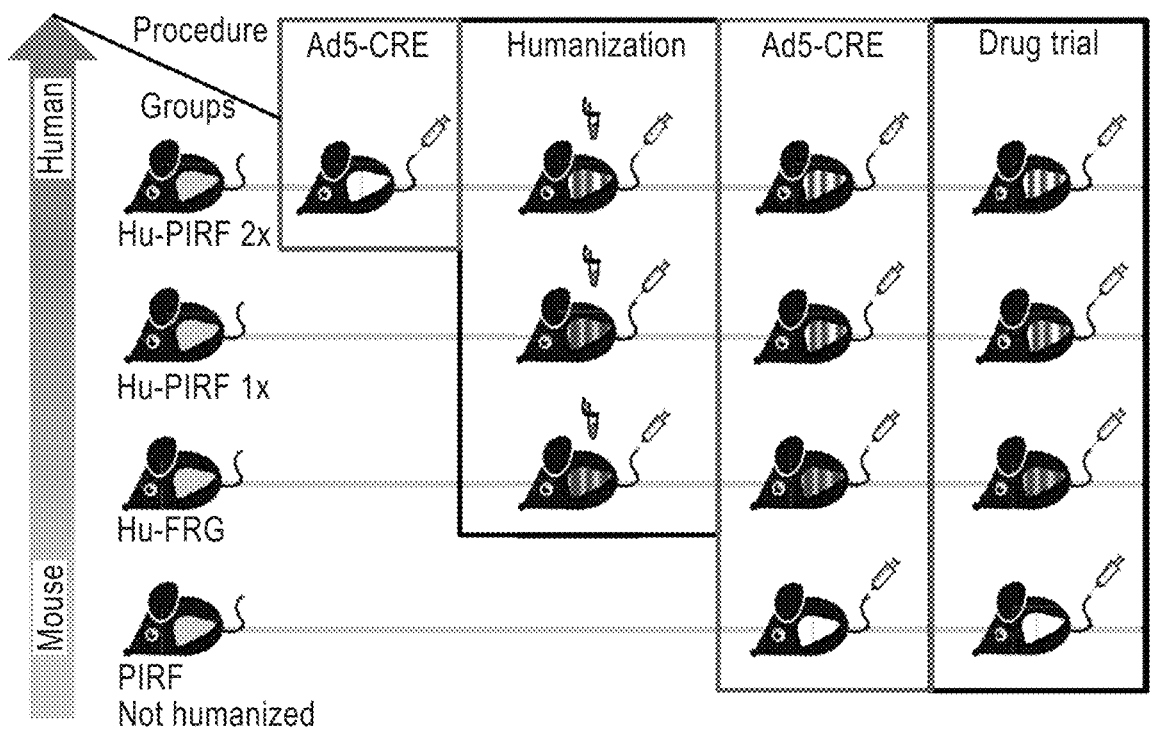
FIG. 10 shows the experimental setup for drug studies in humanized and non-humanized control mice. Humanized (Hu) and not-humanized PIRF and FRG ice were injected once (1×, before transplantation of human hepatocytes) or twice (2×, before and after reaching high human chimerism) before doing drug studies. Injected adenovirus expresses the CRE-recombinase, which leads to deletion of the Por gene in the PIRF, but not in the FRG strain (control). Orange; murine drug metabolism, white; inhibited murine drug metabolism, blue; human drug metabolism.
Figure 15:
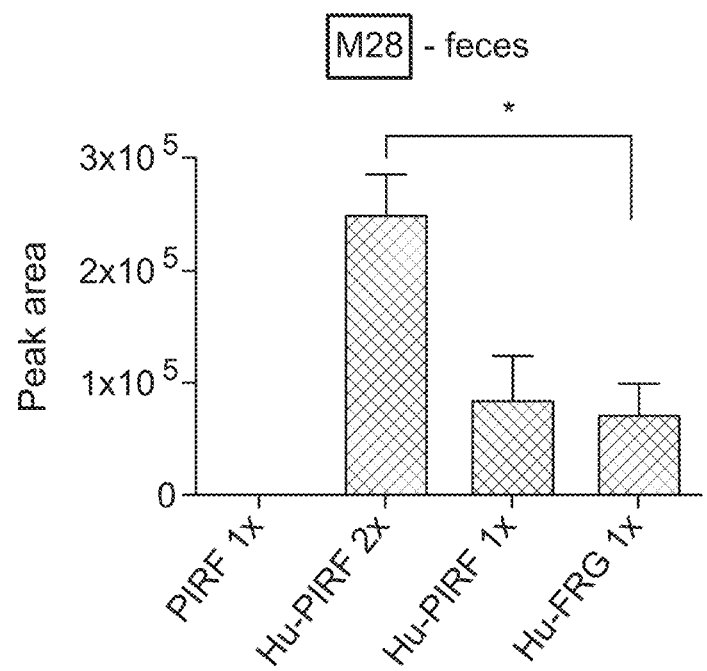
FIG. 15 is a bar graph showing Gefitinib metabolite M28 in feces.

The biggest and most relevant reduction was observed for O-desmethyl gefitinib (M4, M523595), which is by far the most abundant metabolite in human feces. Rodents produce many different metabolites in addition to M4[40, 41] (FIG. 3B), so the M4 metabolite in murine Por-deleted and Por-expressing humanized and non-humanized control mice was analyzed (FIG. 10). The highest levels of M4 were detected in murine Por-deficient Hu-PIRF mice, where human hepatocytes preferentially metabolize gefitinib to M4 and the remaining murine hepatocytes are inhibited in their drug metabolism were used (FIG. 3C). Next, to measure other human-specific metabolites. The most abundant human metabolite was M28, which could not be detected at all in non-humanized control mice. Mass spectrometry again showed the highest level of this human-specific metabolite in murine Por-deficient Hu-PIRF mice (FIG. 3D and FIG. 15), confirming that these mice showed liver metabolism more similar to humans.

Figure 16A:
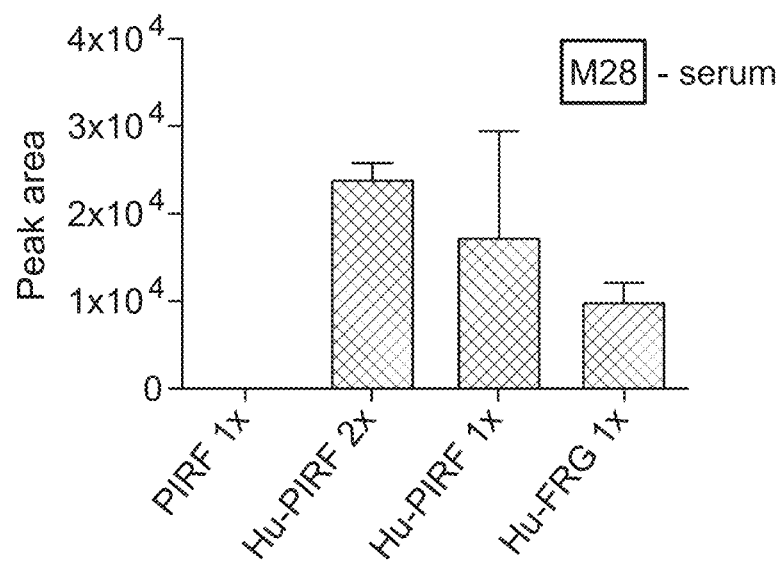
FIG. 16 is a pair of bars graphs showing Gefitinib metabolite M28 in the (A) serum and (B) urine of hu-PIRF-2× mice and control groups.
Figure 16B:
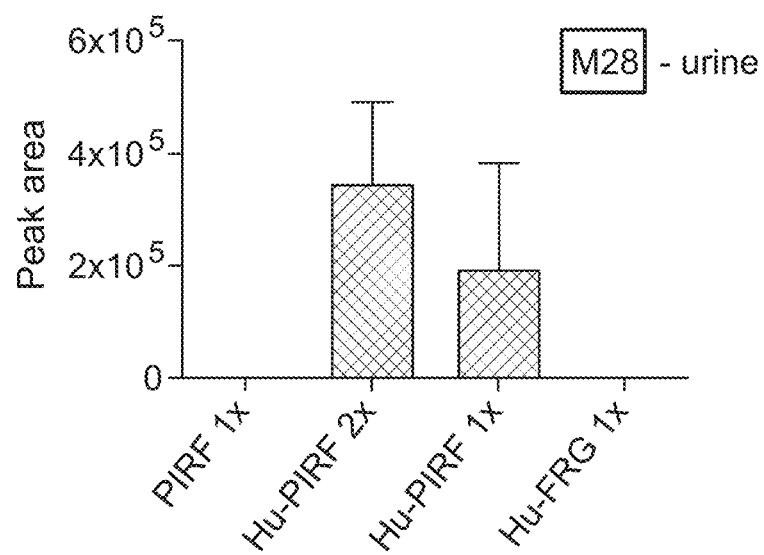

The Por-deficient Hu-PIRF mouse is a novel model system for drug metabolism studies, and therefore was used to analyze different body compartments, e.g. the serum (one hour after injection) and the urine for these key gefitinib metabolites. M4 could not be detected in the urine and was massively reduced (23-fold in Hu-PIRF mice) in the serum, while M28 was detectable at lower concentrations in both the urine and the serum of Hu-PIRF mice (FIG. 16A and FIG. 16B). Although present at lower levels in both compartments, M28 mirrored relative abundance observed in feces (FIG. 3C). These findings confirm that gefitinib metabolites are primarily excreted trough the feces[40, 41].

To confirm human xenobiotic metabolism using liver homogenates of PIRF mice. Atazanavir, an antiretroviral drug (protease inhibitor) for treatment of human immunodeficiency virus was tested. Previous studies in human and mouse microsomes demonstrated that atazanavir metabolite M15 is a predominant human metabolite[42]. To determine levels of M15 in humanized PIRF mice, PIRF mice were intravenously injected with atazanavir and their livers harvested, 30 min after injection. M15 levels in Por-deleted humanized PIRF mice were 5.4 times greater than those observed in non-deleted mice (FIG. 3E), again indicating that these mice metabolize drugs as humans do.

Example 16: Deletion of the UDP-Glucose 6-Dehydrogenase (UGDH)

Deletion of the UDP-glucose 6-dehydrogenase (UGDH) leads to depletion of UDP-glucuronate, which is the substrate of all UDP-glucuronosyl transferases (UGT). UGTs glucuronidate lipophilic drugs in the liver (phase II) and thereby contribute to biotransformation of drugs in the liver; glucuronidated drugs are more polar (hydrophilic) and more easily excreted. Deletion of UGDH is embryonically lethal and therefore needs to be deleted conditionally or by somatic genome engineering, similar to POR. Troglitazone was developed as an antidiabetic drug but withdrawn from the market due to hepatotoxicity. Interestingly, mice and humans metabolize the drug differently, meaning that humans mainly generate sulfate metabolites (main circulating metabolites) while glucuronide conjugates of troglitazone are less prevalent in humans. In contrast to mice, which generate mostly glucuronide conjugates. Hence troglitazone offers an opportunity to validate effectiveness of the approach to inhibit UDP-glucuronosyl transferases (UGT) by deletion of UDP-glucose 6-dehydrogenase (UGDH) in human liver chimeric mice in addition to the Por deletion and humanization.

Glutathione synthetase (GSS) catalyzes the second step of glutathione biosynthesis. Glutathione is the substrate of Gluthatione S-transferases (GST), which conjugates the molecule to lipophilic drugs (phase II) and thereby contribute to biotransformation of drugs in the liver.

Figure 21A:
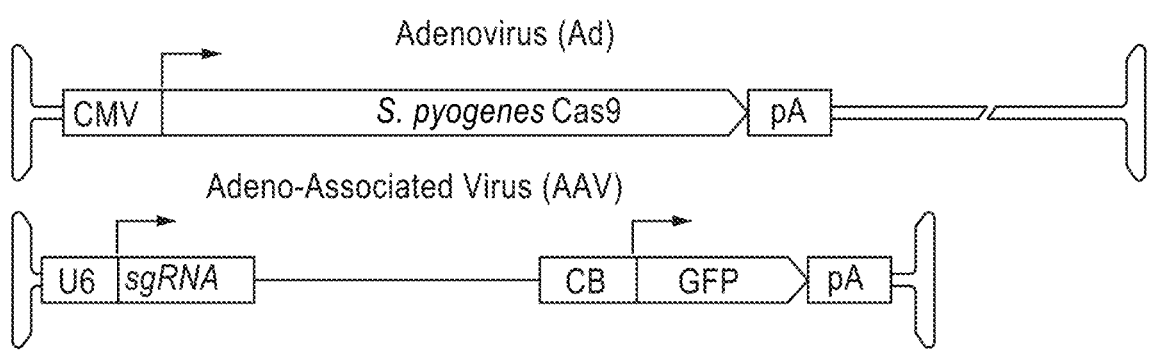
FIG. 21A-B shows gene therapy vector design for liver-specific deletion by genome engineering of drug metabolizing enzymes in humanized mice. A. Two vector design: S.pyogenes Cas9 under the control of CMV promoter in an adenoviral vector (Ad), and Adeno-Associated Virus (AAV) expressing a sgRNA targeting a drug metabolizing enzyme and co-expression of GFP on the same construct.
Figure 21B:
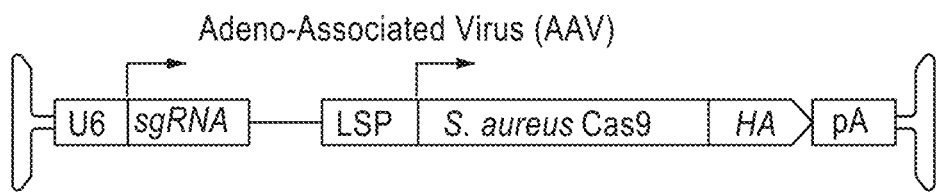
Figure 22:
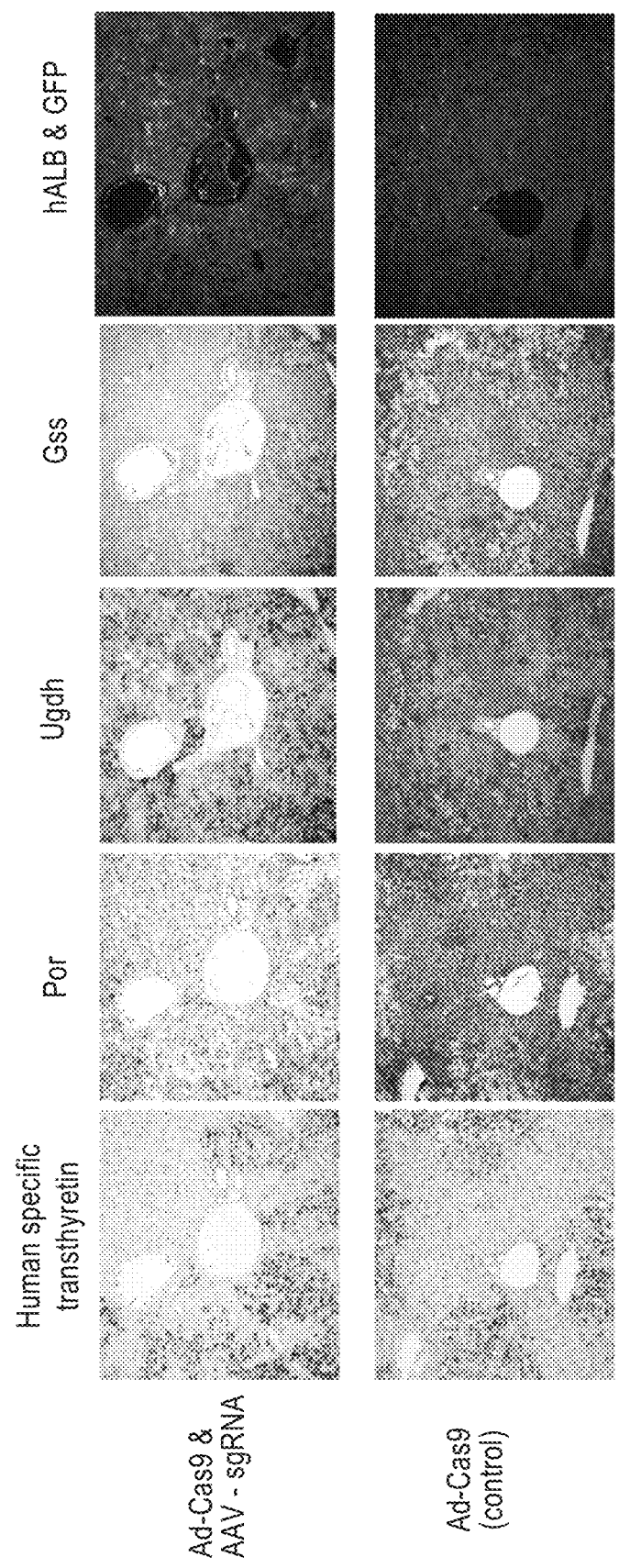
FIG. 22 shows simultaneous deletion of murine P450 oxidoreductase (Por) and other murine enzymes involved in drug metabolism in humanized mice by somatic genome engineering. Humanized FRG mice (human albumin in murine serum >2 mg/ml) have been injected with Adeno-Associated Virus (AAV, serotype 8) expressing sgRNA targeting an early exon of murine Por, UDP-glucose 6-dehydrogenase (Ugdh) or the glutathione synthetase (Gss) gene (see gene therapy vector design, FIG. 21). AAVs have been injected (2×10$^{11}$ GC/AAV/mouse) 1 week before injection of Adenovirus expressing Cas9 (7×10$^9$ pfu/Ad/mouse). Control mice have been injected with adenoviral vector only (lower row). Shown are serial sections of a representative humanized area with immunostaining for human specific Pre-ALB (transthyretin), Por, Ugdh, Gss, hALB and GFP, the latter being expressed from the AAV gene therapy vector (see gene therapy vector design, FIG. 21). Bar represents 50 m. ALB, Albumin.

Somatic genome engineering is used to simultaneously delete murine P450 oxidoreductase (Por) and other murine enzymes involved in drug metabolism in humanized mice. Humanized FRG mice (human albumin in murine serum >2 mg/ml) are injected with Adeno-Associated Virus (AAV, serotype 8) expressing sgRNA targeting an early exon of murine Por, UDP-glucose 6-dehydrogenase (Ugdh) or the glutathione synthetase (Gss) gene (see gene therapy vector design, FIG. 21). AAVs are injected ($2 \times 10^{11}$ GC/AAV/mouse) 1 week before injection of Adenovirus expressing Cas9 ($7 \times 10^9$ pfu/Ad/mouse). Control mice are injected with adenoviral vector only (Figure. 22, lower row). Results show a deletion of murine por, as well as ugdh and gss genes. The knockdown by CRISPR/Cas9 of the murine por in humanized mice is substantial but not quite as efficient as the knockdown observed with the loxP/CRE system when looking at the DNA (Figure. 23) and protein levels (Figure. 22). Also, the por deletion particularly in FRG mice is independent of the deletion of the other two genes (ugdh and gss), since their sgRNA (targeting molecule) are all on different AAV vectors. However, immunostaining (Figure. 22) demonstrated that substantial amounts of cells had deletion of por and gss (FIG. 22), while the deletion of ugdh was less efficient.

Figure 23:
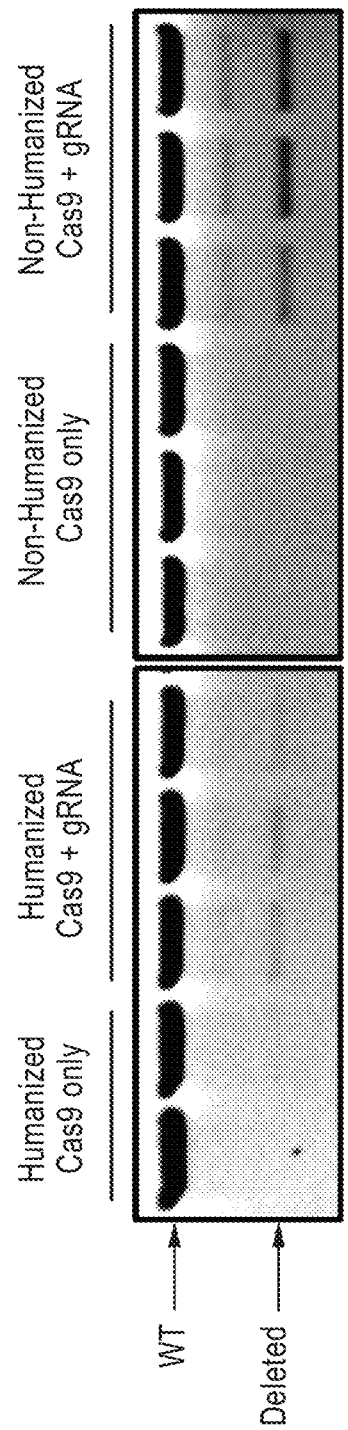
FIG. 23 shows genomic deletion of por by CRISPR/Cas9: Wild type and humanized FRG mice (human albumin in murine serum >2 mg/ml) are injected with two Adeno-Associated Virus (AAV, serotype 8) expressing sgRNA targeting consecutive early exons of murine Por as well as S. aureus Cas9 (see gene therapy vector design, FIG. 21). AAVs are injected (2×10$^{11}$ GC/AAV/mouse). Control mice are injected with adenoviral vector expressing Cas9 only (7×10$^9$ pfu/Ad/mouse). Shown are PCR amplifications of the region spanning the two nearby targeting sites. Upon CRISPR/Cas9 mediated cutting of DNA on both target sites results in a deletion of the por gene leading to a smaller PCR amplicon.
Figure 24:
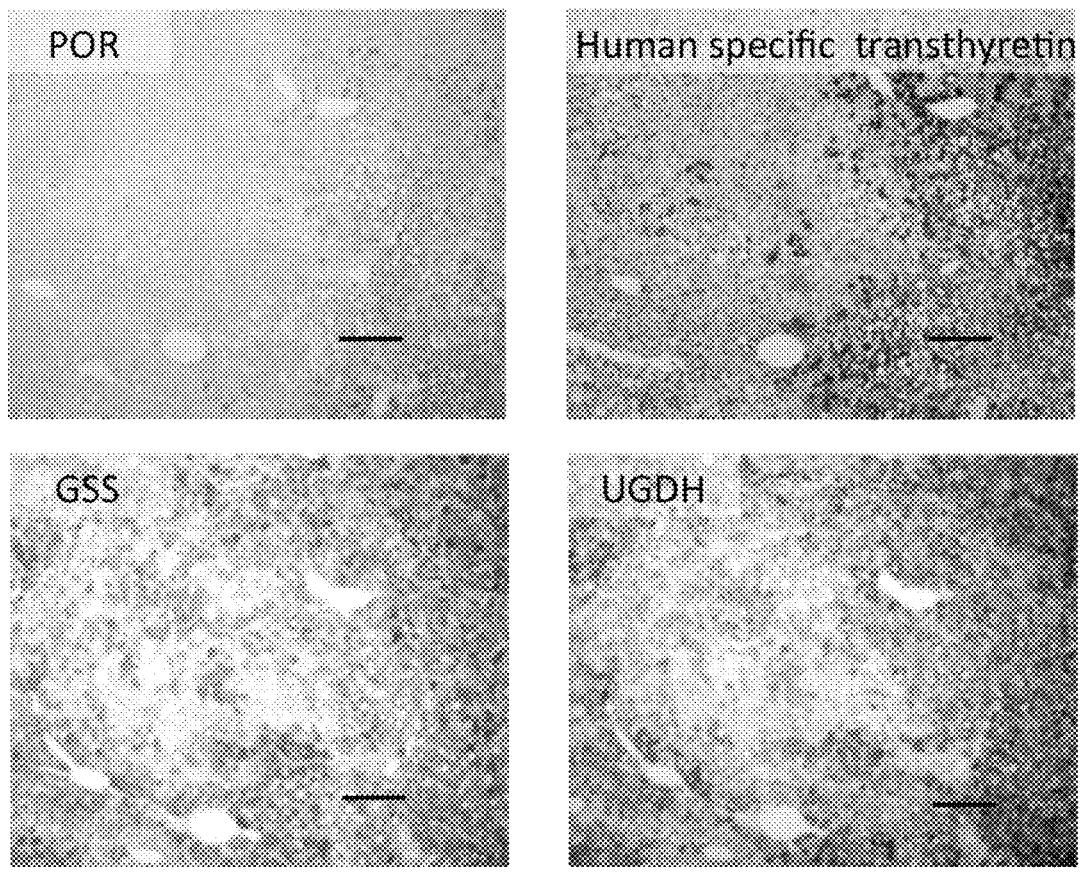
FIG. 24 shows humanized PIRF mouse with transgenic Alb-CRE and deletion of other murine enzymes involved in drug metabolism. Por was deleted by expression of CRE, but instead of adenoviral CRE, this PIRF mouse carries an Alb-CRE sequence within the murine genome. After humanization, mice were injected with Adeno-Associated Virus (AAV, serotype 8) expressing sgRNA targeting an early exon UDP-glucose 6-dehydrogenase (Ugdh) or the glutathione synthetase (Gss) gene (see gene therapy vector design, FIG. 21). AAVs are injected (2×10$^{11}$ GE/AAV/mouse) 1 week before injection of Adenovirus expressing Cas9 (7×10$^9$ GE/Ad/mouse). Shown are serial sections of a representative humanized area with immunostaining for human specific Pre-ALB (transthyretin), Por, Ugdh or Gss. Bar represents 50 μm. ALB, Albumin.
Figure 25A:
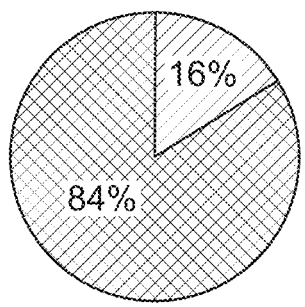
FIG. 25A-D shows troglitazone Phase II metabolites detected in liver of humanized and non-humanized FRG mice with and without Por and Ugdh deletion. Percentage of liver glucuronidated and sulfated metabolites detected in humanized livers 2 hours after i.p injection of troglitazone (600 mg/kg).
Figure 25B:
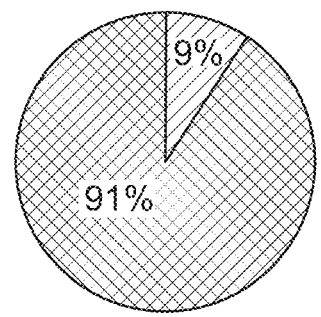
Figure 25C:
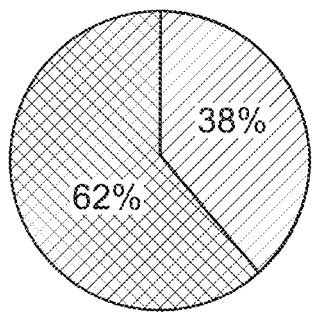
Figure 25D:
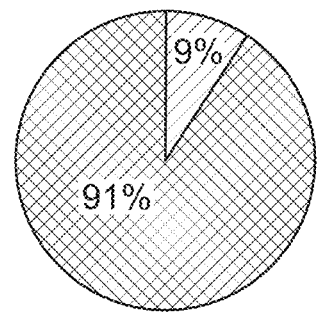

Humanized PIRF mouse with transgenic Alb-CRE and deletion of other murine enzymes involved in drug metabolism are used. Por is deleted by expression of CRE, but instead of adenoviral CRE, this PIRF mouse carries an Alb-CRE sequence within the murine genome. These mice efficiently repopulate with human hepatocytes as evidenced by human specific albumin >2 mg/ml in the murine blood and transthyretin (prealbumin) staining in the chimeric liver (Figure. 24). Murine por is efficiently deleted in the liver of these chimeric mice since the albumin promoter is expressed already in late embryonic stages in the liver. Also in these humanized PIRF mice, in addition to the por, gss and ugdh can also be deleted (Figure. 23).

Example 17: Analysis of Troglitazone Metabolites

Troglitazone metabolites (two hours after i.p. injection of 600 mg/kg troglitazone) in the livers of humanized and non-humanized FRG mice with and without Por and Ugdh deletion was analyzed. Non-humanized livers of control mice had much higher amounts of glucuronide conjugates than humans or humanized PIRF mice (Figure. 24). Furthermore, glucuronide conjugates reduced significantly upon deletion of ugdh and por in non-humanized and humanized PIRF mice. This data confirms that deletion of ugdh leads also to a functional impairment or abolishment of UGTs in the human liver chimeric liver.

The present disclosure provides a next generation of humanized mouse model amenable to human drug metabolism with minimal interference from the murine P450 cytochromes. The production of human metabolites for two different drugs between humanized PIRF mice and "normal" humanized FRG mice were compared. Analyses revealed higher concentrations of human metabolites in murine feces and liver homogenate in humanized PIRF mice than in FRG mice and demonstrate that these mice have humanized drug metabolism. The PIRF and FRG strains used in this study are in a mixed (C57B and 129S) genetic background. Aside from potential differences in the background to the two previously published FRG mouse strains[5, 7], our CRISPR/Cas9 generated knockout strains do not express any transgenes, e.g. the neomycin phosphotransferase that inactivates a wide range of aminoglycoside antibiotics. This model system is useful for early detection of reactive metabolites and is an elegant way to block a large and confounding cluster of drug metabolizing murine enzymes. In addition to the novel mouse model provided herein, the disclosure provides (a) knocking out Por in a combination of multiple organs like the gut and the liver or the lung and the liver would be desirable, (b) additional deletions in other drug-metabolizing enzymes and/or achieving a Por deletion more efficiently. Using transgenic mice expressing Cre recombinase would require yet another crossing step into a quadruple transgenic (PIRF) mouse, however, and an early organ-specific deletion might not generate a robust strain amenable to xenotransplantation.

In summary, the present disclosure provides a novel mouse model combining human chimerism with functional deletion of all murine cytochromes by Por deletion. Such a murine Por-deficient humanization can be used in combination with other repopulation models such as the transgenic uPA mouse[11, 21]. Studies with two different drugs in two different body compartments demonstrate that studies in humanized PIRF mice efficiently identify human metabolites.

REFERENCES

1. Olson H, et al. Concordance of the toxicity of pharmaceuticals in humans and in animals. *Regulatory toxicology and pharmacology: RTP* 32, 56-67 (2000).
2. Nelson D R, Zeldin D C, Hoffman S M, Maltais L J, Wain H M, Nebert D W. Comparison of cytochrome P450 (CYP) genes from the mouse and human genomes, including nomenclature recommendations for genes, pseudogenes and alternative-splice variants. *Pharmacogenetics* 14, 1-18 (2004).
3. Guengerich F P, Cheng Q. Orphans in the human cytochrome P450 superfamily: approaches to discovering functions and relevance in pharmacology. *Pharmacological reviews* 63, 684-699 (2011).
4. Mercer D F, et al. Hepatitis C virus replication in mice with chimeric human livers. *Nat Med* 7, 927-933 (2001).
5. Bissig K D, Le T T, Woods N B, Verma I M. Repopulation of adult and neonatal mice with human hepatocytes: a chimeric animal model. *Proc Natl Acad Sci USA* 104, 20507-20511 (2007).

6. Dandri M, et al. Repopulation of mouse liver with human hepatocytes and in vivo infection with hepatitis B virus. *Hepatology* 33, 981-988 (2001).
7. Azuma H, et al. Robust expansion of human hepatocytes in Fah(−/−)/Rag2(−/−)/Il2rg(−/−) mice. *Nat Biotechnol* 25, 903-910 (2007).
8. Hasegawa M, et al. The reconstituted 'humanized liver' in TK-NOG mice is mature and functional. *Biochemical and biophysical research communications* 405, 405-410 (2011).
9. Washburn M L, et al. A humanized mouse model to study hepatitis C virus infection, immune response, and liver disease. *Gastroenterology* 140, 1334-1344 (2011).
10. Suemizu H, et al. Establishment of a humanized model of liver using NOD/Shi-scid IL2Rgnull mice. *Biochem Biophys Res Commun* 377, 248-252 (2008).
11. Heckel J L, Sandgren E P, Degen J L, Palmiter R D, Brinster R L. Neonatal bleeding in transgenic mice expressing urokinase-type plasminogen activator. *Cell* 62, 447-456 (1990).
12. Tateno C, et al. Near completely humanized liver in mice shows human-type metabolic responses to drugs. *Am J Pathol* 165, 901-912 (2004).
13. Samuelsson K, et al. Troglitazone metabolism and transporter effects in chimeric mice: a comparison between chimeric humanized and chimeric murinized FRG mice. *Xenobiotica; the fate of foreign compounds in biological systems* 44, 186-195 (2014).
14. Lootens L, et al. Steroid metabolism in chimeric mice with humanized liver. *Drug testing and analysis* 1, 531-537 (2009).
15. Foster J R, et al. Differential effect of troglitazone on the human bile acid transporters, MRP2 and BSEP, in the PXB hepatic chimeric mouse. *Toxicologic pathology* 40, 1106-1116 (2012).
16. Xu D, et al. Fialuridine induces acute liver failure in chimeric T K-NOG mice: a model for detecting hepatic drug toxicity prior to human testing. *PLoS medicine* 11, e1001628 (2014).
17. Bateman T J, Reddy V G, Kakuni M, Morikawa Y, Kumar S. Application of chimeric mice with humanized liver for study of human-specific drug metabolism. *Drug Metab Dispos* 42, 1055-1065 (2014).
18. Nishimura T, et al. Using chimeric mice with humanized livers to predict human drug metabolism and a drug-drug interaction. *J Pharmacol Exp Ther* 344, 388-396 (2013).
19. Tanoue C, et al. Prediction of human metabolism of the sedative-hypnotic zaleplon using chimeric mice transplanted with human hepatocytes. *Xenobiotica; the fate of foreign compounds in biological systems* 43, 956-962 (2013).
20. Bissig K D, et al. Human liver chimeric mice provide a model for hepatitis B and C virus infection and treatment. *The Journal of clinical investigation* 120, 924-930 (2010).
21. Meuleman P, et al. Morphological and biochemical characterization of a human liver in a uPA-SCID mouse chimera. *Hepatology* 41, 847-856 (2005).
22. Kato K, et al. Development of Murine Cyp3a Knockout Chimeric Mice with Humanized Liver. *Drug Metab Dispos* 43, 1208-1217 (2015).
23. Nakada N, et al. Murine Cyp3a knockout chimeric mice with humanized liver: prediction of the metabolic profile of nefazodone in humans. *Biopharmaceutics & drug disposition*, (2015).
24. Shen A L, O'Leary K A, Kasper C B. Association of multiple developmental defects and embryonic lethality with loss of microsomal NADPH-cytochrome P450 oxidoreductase. *J Biol Chem* 277, 6536-6541 (2002).
25. Wu L, et al. Conditional knockout of the mouse NADPH-cytochrome p450 reductase gene. *Genesis* 36, 177-181 (2003).
26. Henderson C J, et al. Inactivation of the hepatic cytochrome P450 system by conditional deletion of hepatic cytochrome P450 reductase. *J Biol Chem* 278, 13480-13486 (2003).
27. Gu J, et al. Liver-specific deletion of the NADPH-cytochrome P450 reductase gene: impact on plasma cholesterol homeostasis and the function and regulation of microsomal cytochrome P450 and heme oxygenase. *J Biol Chem* 278, 25895-25901 (2003).
28. Thomas K R, Capecchi M R. Site-directed mutagenesis by gene targeting in mouse embryo-derived stem cells. *Cell* 51, 503-512 (1987).
29. Skarnes W C, et al. A conditional knockout resource for the genome-wide study of mouse gene function. *Nature* 474, 337-342 (2011).
30. Farley F W, Soriano P, Steffen L S, Dymecki S M. Widespread recombinase expression using FLPeR (flipper) mice. *Genesis* 28, 106-110 (2000).
31. Haft D H, Selengut J, Mongodin E F, Nelson K E. A guild of 45 CRISPR-associated (Cas) protein families and multiple CRISPR/Cas subtypes exist in prokaryotic genomes. *PLoS computational biology* 1, e60 (2005).
32. Jinek M, Chylinski K, Fonfara I, Hauer M, Doudna J A, Charpentier E. A programmable dual-RNA-guided DNA endonuclease in adaptive bacterial immunity. *Science* 337, 816-821 (2012).
33. Jansen R, Embden J D, Gaastra W, Schouls L M. Identification of genes that are associated with DNA repeats in prokaryotes. *Molecular microbiology* 43, 1565-1575 (2002).
34. Bissig-Choisat B, et al. Development and rescue of human familial hypercholesterolaemia in a xenograft mouse model. *Nature communications* 6, 7339 (2015).
35. Weng Y, DiRusso C C, Reilly A A, Black P N, Ding X. Hepatic gene expression changes in mouse models with liver-specific deletion or global suppression of the NADPH-cytochrome P450 reductase gene. Mechanistic implications for the regulation of microsomal cytochrome P450 and the fatty liver phenotype. *J Biol Chem* 280, 31686-31698 (2005).
36. Williams J A, et al. Drug-drug interactions for UDP-glucuronosyltransferase substrates: a pharmacokinetic explanation for typically observed low exposure (AUCi/AUC) ratios. *Drug Metab Dispos* 32, 1201-1208 (2004).
37. Barker A J, et al. Studies leading to the identification of ZD1839 (IRESSA): an orally active, selective epidermal growth factor receptor tyrosine kinase inhibitor targeted to the treatment of cancer. *Bioorganic & medicinal chemistry letters* 11, 1911-1914 (2001).
38. Herbst R S, Fukuoka M, Baselga J. Gefitinib—a novel targeted approach to treating cancer. *Nat Rev Cancer* 4, 956-965 (2004).
39. Liu X, et al. Metabolomics reveals the formation of aldehydes and iminium in gefitinib metabolism. *Biochem Pharmacol* 97, 111-121 (2015).
40. McKillop D, et al. Metabolic disposition of gefitinib, an epidermal growth factor receptor tyrosine kinase inhibitor, in rat, dog and man. *Xenobiotica; the fate of foreign compounds in biological systems* 34, 917-934 (2004).

41. Scheffler M, Di Gion P, Doroshyenko O, Wolf J, Fuhr U. Clinical pharmacokinetics of tyrosine kinase inhibitors: focus on 4-anilinoquinazolines. *Clinical pharmacokinetics* 50, 371-403 (2011).
42. Li F, Lu J, Wang L, Ma X. CYP3A-mediated generation of aldehyde and hydrazine in atazanavir metabolism. *Drug Metab Dispos* 39, 394-401 (2011).
43. Baillie T A. Future of toxicology-metabolic activation and drug design: challenges and opportunities in chemical toxicology. *Chemical research in toxicology* 19, 889-893 (2006).
44. Guengerich F P, MacDonald J S. Applying mechanisms of chemical toxicity to predict drug safety. *Chemical research in toxicology* 20, 344-369 (2007).
45. Dalvie D, et al. Assessment of three human in vitro systems in the generation of major human excretory and circulating metabolites. *Chemical research in toxicology* 22, 357-368 (2009).
46. Anderson S, Luffer-Atlas D, Knadler M P. Predicting circulating human metabolites: how good are we? *Chemical research in toxicology* 22, 243-256 (2009).
47. Pettitt S J, et al. Agouti C57BL/6N embryonic stem cells for mouse genetic resources. *Nat Methods* 6, 493-495 (2009).
48. Cradick T J, Qiu P, Lee C M, Fine E J, Bao G. COSMID: A Web-based Tool for Identifying and Validating CRISPR/Cas Off-target Sites. *Molecular therapy Nucleic acids* 3, e214 (2014).
49. Hwang W Y, et al. Efficient genome editing in zebrafish using a CRISPR-Cas system. *Nat Biotechnol* 31, 227-229 (2013).
50. Cong L, et al. Multiplex genome engineering using CRISPR/Cas systems. *Science* 339, 819-823 (2013).
51. Ponder K P, et al. Mouse hepatocytes migrate to liver parenchyma and function indefinitely after intrasplenic transplantation. *Proc Natl Acad Sci USA* 88, 1217-1221 (1991).
52. Li B, Dewey C N. RSEM: accurate transcript quantification from RNA-Seq data with or without a reference genome. *BMC Bioinformatics* 12, 323 (2011).
53. Langmead B, Salzberg S L. Fast gapped-read alignment with Bowtie 2. *Nat Methods* 9, 357-359 (2012).
54. Eisenberg E, Levanon E Y. Human housekeeping genes, revisited. *Trends in genetics: TIG* 29, 569-574 (2013).

What is claimed is:

1. A method for preparing a chimeric mouse comprising human hepatocytes, the method comprising:
   (a) providing a transgenic mouse whose genome comprises:
      (i) a liver specific homozygous deletion of endogenous NADPH-P450 oxidoreductase (Por) gene, wherein the deleted Por gene is a conditional knockout of the endogenous Por gene such that no functional endogenous Por protein is produced; and
      (ii) a homozygous deletion of endogenous Rag2, IL-2Rg and Fah genes (Fah-/- Rag2-/-IL-2rg-/-), wherein the mouse is immune-deficient, lacking T, B and NK cells,
   wherein the transgenic mouse having a liver specific homozygous deletion of endogenous Por gene of (i) is generated by:
      1) providing a mouse comprising a floxed allele of the endogenous Por gene with at least one dose of an adenoviral vector encoding Cre recombinase (Ade-Cre), wherein the at least a first dose is sufficient such that no functional endogenous Por protein is produced; or
      2) crossing a first transgenic mouse comprising a foxed allele of the endogenous Por gene with a second transgenic mouse strain that expresses CRE recombinase under the liver-specific promoter,
   and wherein the liver of the transgenic mouse accumulated lipid as compared to a wild type mouse; and
   (b) transplanting human hepatocytes into the transgenic mouse of step (a) to produce a chimeric Rag-/-Il-2Rg-/- Fah-/- Por-/- mouse, wherein the human hepatocytes account for at least 70% of all hepatocytes in the liver of the chimeric Rag-/-Il-2Rg-/- Fah-/- Por-/- mouse.

* * * * *